United States Patent
Choi et al.

(10) Patent No.: US 12,365,697 B2
(45) Date of Patent: Jul. 22, 2025

(54) COMPOUND AND PHOTOELECTRIC DEVICE, IMAGE SENSOR, AND ELECTRONIC DEVICE INCLUDING THE SAME

(71) Applicant: Samsung Electronics Co., Ltd., Suwon-si (KR)

(72) Inventors: Taejin Choi, Suwon-si (KR); Hyeong-Ju Kim, Changwon-si (KR); Kyung Bae Park, Hwaseong-si (KR); Jisoo Shin, Suwon-si (KR); Sung Young Yun, Suwon-si (KR); Seon-Jeong Lim, Yongin-si (KR); Youn Hee Lim, Suwon-si (KR); Hye Rim Hong, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 680 days.

(21) Appl. No.: 17/559,069

(22) Filed: Dec. 22, 2021

(65) Prior Publication Data

US 2022/0216418 A1 Jul. 7, 2022

(30) Foreign Application Priority Data

Dec. 24, 2020 (KR) .................. 10-2020-0183036

(51) Int. Cl.
*C07D 517/16* (2006.01)
*C07D 421/06* (2006.01)
(Continued)

(52) U.S. Cl.
CPC ......... *C07D 517/16* (2013.01); *C07D 421/06* (2013.01); *C07F 7/0816* (2013.01);
(Continued)

(58) Field of Classification Search
CPC .... H10K 85/636; H10K 85/40; H10K 85/654; H10K 85/657; H10K 30/30; H10K 39/32;
(Continued)

(56) References Cited

U.S. PATENT DOCUMENTS 8,525,577 B2  9/2013  Yofu et al.
8,642,660 B2  2/2014  Goldfarb
(Continued)

FOREIGN PATENT DOCUMENTS

KR  10-2019-0044555 A  4/2019
KR  10-2020-0110628  *  8/2020
(Continued)

OTHER PUBLICATIONS

Hokuto Seo et al., "Color Sensors with Three Vertically Stacked Organic Photodetectors", Japanese Journal of Applied Physics, vol. 46, No. 49, pp. L1240-L1242, 2007.
(Continued)

*Primary Examiner* — Joseph K McKane
*Assistant Examiner* — Ashli Ariana Chicks
(74) *Attorney, Agent, or Firm* — Harness, Dickey & Pierce, P.L.C.

(57) ABSTRACT

A compound of Chemical Formula 1, and an organic photoelectric device, an image sensor, and an electronic device including the same are disclosed:

[Chemical Formula 1]

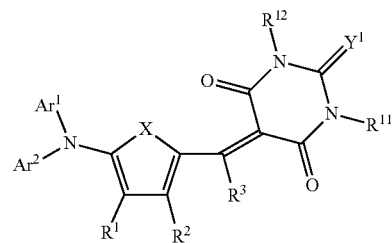

In Chemical Formula 1, each substituent is the same as defined in the detailed description.

19 Claims, 10 Drawing Sheets

(51) Int. Cl.
*C07F 7/08* (2006.01)
*H10K 30/00* (2023.01)
*H10K 30/30* (2023.01)
*H10K 39/32* (2023.01)
*H10K 85/40* (2023.01)
*H10K 85/60* (2023.01)

(52) U.S. Cl.
CPC .......... *H10K 30/451* (2023.02); *H10K 85/40* (2023.02); *H10K 85/636* (2023.02); *H10K 85/654* (2023.02); *H10K 85/657* (2023.02); *H10K 30/30* (2023.02); *H10K 39/32* (2023.02); *H10K 85/649* (2023.02)

(58) Field of Classification Search
CPC .. H10K 85/649; C07D 421/06; C07D 517/16; C07F 7/0816
See application file for complete search history.

(56) References Cited

U.S. PATENT DOCUMENTS

| | | | | |
|---|---|---|---|---|
| 9,941,477 | B2 * | 4/2018 | Choi | H10K 85/633 |
| 9,960,362 | B2 * | 5/2018 | Bulliard | C07D 405/06 |
| 10,096,781 | B2 | 10/2018 | Tadao et al. | |
| 10,236,461 | B2 * | 3/2019 | Ro | H10K 85/654 |
| 10,290,812 | B2 * | 5/2019 | Lim | H10K 85/636 |
| 10,381,412 | B2 * | 8/2019 | Leem | H10K 85/636 |
| 10,505,146 | B2 * | 12/2019 | Heo | H10K 50/844 |
| 11,145,822 | B2 | 10/2021 | Shin et al. | |
| 11,532,671 | B2 * | 12/2022 | Leem | H10K 71/30 |
| 11,737,360 | B2 * | 8/2023 | Minami | H10K 85/6572 |
| 11,793,007 | B2 * | 10/2023 | Shin | H10K 85/6576 257/40 |
| 2009/0163545 | A1 | 6/2009 | Goldfarb | |
| 2016/0211465 | A1 | 7/2016 | Tadao et al. | |
| 2017/0148994 | A1 * | 5/2017 | Choi | H10K 50/8428 |
| 2017/0346016 | A1 | 11/2017 | Bulliard et al. | |
| 2019/0172872 | A1 * | 6/2019 | Tsutsumi | H10K 85/615 |
| 2020/0350500 | A1 | 11/2020 | Choi et al. | |
| 2022/0073542 | A1 * | 3/2022 | Kim | H10K 85/657 |
| 2023/0113862 | A1 * | 4/2023 | Kim | H10K 85/6576 257/40 |

FOREIGN PATENT DOCUMENTS

| | | | |
|---|---|---|---|
| KR | 10-2020-0127530 A | | 11/2020 |
| KR | 2021-100798 | * | 7/2021 |

OTHER PUBLICATIONS

Satoshi Aihara et al., "Stacked Image Sensor With Green- and Red-Sensitive Organic Photoconductive Films Applying Zinc Oxide Thin-Film Transistors to a Signal Readout Circuit", IEE Transactions on Electron Devices, vol. 56, No. 11, Nov. 2009, pp. 2570-2576.

Mikio Ihama et al., "CMOS Image Sensor with a Thin Overlaid Panchromatic Organic Photoconductive Layer for Sensors with Reduced Pixel Size", IDW '09, pp. 2123-2126.

Seon-Jeong Lim et al., "Organic-on-silicon complementary metal-oxide-semiconductor colour image sensors", Scientific Reports, 5:7708, DOI: 10.1038/srep07708, Jan. 12, 2015, pp. 1-7.

Juha Alakarhu, 'Image Sensors and Image Quality in Mobile Phones' *International Image Sensor Workshop*, 2007, p. 1-4.

* cited by examiner

COMPOUND AND PHOTOELECTRIC DEVICE, IMAGE SENSOR, AND ELECTRONIC DEVICE INCLUDING THE SAME

CROSS-REFERENCE TO RELATED APPLICATION

This application claims priority to and the benefit of Korean Patent Application No. 10-2020-0183036 filed in the Korean Intellectual Property Office on Dec. 24, 2020, the entire contents of which are incorporated herein by reference.

BACKGROUND

1. Field

Example embodiments provide a compound and a photoelectric device, an image sensor, and an electronic device including the same.

2. Description of the Related Art

A photoelectric device converts light into an electrical signal using photoelectric effects. The photoelectric device may include a photodiode, a phototransistor, and the like, and it may be applied to an image sensor, an organic light emitting diode, and the like.

An image sensor including a photodiode requires high resolution and thus a small pixel. At present, a silicon photodiode is widely used, but it has a problem of deteriorated sensitivity since silicon photodiode has a smaller absorption area due to small pixels. Accordingly, an organic material that is capable of replacing silicon has been researched.

SUMMARY

Some example embodiments provide a compound that is selectively configured to absorb light in a green wavelength region and has improved light absorption characteristics. Such a compound may be or may be included in an organic material of a photoelectric device that may have a high extinction coefficient and may selectively absorb light in a particular wavelength region depending on a molecular structure, and thus may simultaneously replace a photodiode and a color filter and resultantly improve sensitivity and contribute to high integration.

Some example embodiments also provide a photoelectric device (e.g., organic photoelectric device) that is selectively configured to absorb light in the green wavelength region and has improved light absorption characteristics.

Some example embodiments also provide an image sensor including the photoelectric device (e.g., organic photoelectric device).

Some example embodiments also provide an electronic device including the image sensor.

According to some example embodiments, a compound is represented by Chemical Formula 1.

[Chemical Formula 1]

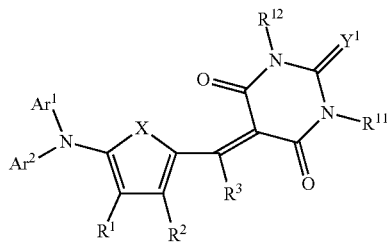

In Chemical Formula 1,
Ar$^1$ and Ar$^2$ are each independently a substituted or unsubstituted 5-membered aromatic ring, a substituted or unsubstituted 6-membered aromatic ring, or a condensed ring of two or more, wherein Ar$^1$ and Ar$^2$ are each independently present or linked with each other to provide a condensed ring,
X is S, Se, Te, O, S(=O), S(=O)$_2$, NR$^a$, Or SiR$^b$R$^c$, wherein R$^a$, R$^b$, and R$^c$ are each independently hydrogen or a substituted or unsubstituted C1 to C10 alkyl group,
R$^1$ to R$^3$ are each independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, wherein R$^1$ and R$^2$ are each independently present or linked with each other to provide a ring,
Y$^1$ is O, S, Se, Te, or C(R$^e$)(CN), wherein R$^e$ is hydrogen, a cyano group (—CN), or a C1 to C10 alkyl group, and
R$^{11}$ and R$^{12}$ are each independently hydrogen, deuterium, a C1 to C10 alkyl group, or a C6 to C10 aryl group, wherein one of R$^{11}$ or R$^{12}$ is hydrogen or deuterium.

Chemical Formula 1 may include a cyclic group represented by Chemical Formula 2. The cyclic group represented by Chemical Formula 2 in Chemical Formula 1 may be a cyclic group represented by Chemical Formula 2-1, Chemical Formula 2-2, or Chemical Formula 2-3.

[Chemical Formula 2]

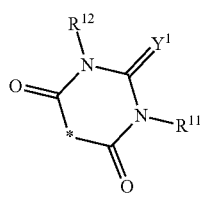

In Chemical Formula 2,
Y$^1$, R$^{11}$, and R$^{12}$ are the same as Y$^1$, R$^{11}$, and R$^{12}$, respectively, in Chemical Formula 1,

[Chemical Formula 2-1]

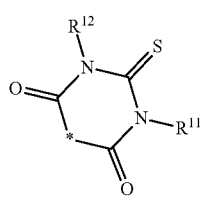

[Chemical Formula 2-2]

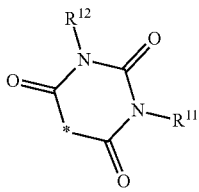

[Chemical Formula 2-3]

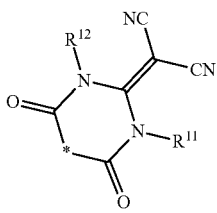

In Chemical Formula 2-1, Chemical Formula 2-2, and Chemical Formula 2-3, $R^{11}$ and $R^{12}$ are the same as $R^{11}$ and $R^{12}$, respectively, in Chemical Formula 1.

In Chemical Formula 1, when $R^1$ and $R^2$ are linked to each other via a linker to provide a ring, and the linker may be represented by Chemical Formula 3-1 or Chemical Formula 3-2.

[Chemical Formula 3-1]

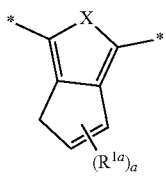

[Chemical Formula 3-2]

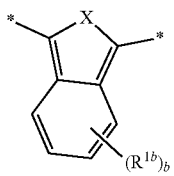

In Chemical Formula 3-1 and Chemical Formula 3-2, $R^{1a}$ and $R^{1b}$ is hydrogen, a C1 to C10 alkyl group, a C6 to C10 aryl group, a C2 to C10 heteroaryl group, or a halogen, and a and b are each independently an integer of 1 to 4.

In Chemical Formula 1, at least one of $Ar^1$ or $Ar^2$ may include a heteroatom selected from nitrogen (N), sulfur (S), and selenium (Se) at a $1^{st}$ position of Chemical Formula 1.

*—$N(Ar^1)(Ar^2)$ of Chemical Formula 1 may be represented by Chemical Formula 4-1.

[Chemical Formula 4-1]

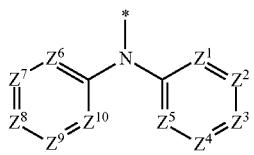

In Chemical Formula 4-1, $Z^1$ to $Z^{10}$ are each independently N or $CR^a$, wherein $R^a$ is hydrogen, a C1 to C6 alkyl group, a C1 to C10 haloalkyl group, —$SiH_3$, a C1 to C10 alkylsilyl group, —$NH_2$, a C1 to C10 alkylamine group, a C6 to C12 aryl group, a C3 to C12 heteroaryl group, a halogen, a cyano group, or a combination thereof, when $Z^1$ to $Z^{10}$ are $CR^a$, $R^a$'s may be present independently or two adjacent ones of $Z^1$ to $Z^{10}$ may be linked to each other to provide a 5-membered aromatic ring or a 6-membered aromatic ring, and is a linking point with Chemical Formula 1.

*—$N(Ar^1)(Ar^2)$ of Chemical Formula 1 may be represented by Chemical Formula 4-2.

[Chemical Formula 4-2]

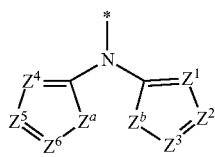

In Chemical Formula 4-2, $X^a$ and $X^b$ are each independently —O—, —S—, —Se—, —Te—, —$NR^a$—, —$SiR^bR^c$—, or —$GeR^dR^e$—, wherein $R^a$, $R^b$, $R^e$, $R^d$, and $R^e$ are each independently hydrogen, a halogen, a substituted or unsubstituted C1 to C10 alkyl group, or a substituted or unsubstituted C6 to C10 aryl group, $Z^1$ to $Z^6$ are each independently N or $CR^x$, wherein $R^x$ is hydrogen, a C1 to C6 alkyl group, a C1 to C10 haloalkyl group, —$SiH_3$, a C1 to C10 alkylsilyl group, —$NH_2$, a C1 to C10 alkylamine group, a C6 to C12 aryl group, a C3 to C12 heteroaryl group, a halogen, a cyano group, or a combination thereof, when $Z^1$ to $Z^6$ are $CR^x$, $R^x$'s may be present independently or two adjacent ones of $Z^1$ to $Z^6$ may be linked to each other to provide a 5-membered aromatic ring or a 6-membered aromatic ring, and

* is a linking point with Chemical Formula 1.

When $Ar^1$ and $Ar^2$ of Chemical Formula 1 are linked to each other to provide a condensed ring, *—$N(Ar^1)(Ar^2)$ may be represented by Chemical Formula 4-3.

[Chemical Formula 4-3]

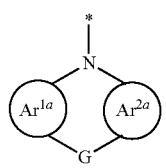

In Chemical Formula 4-3, $Ar^{1a}$ and $Ar^{2a}$ are each independently a substituted or unsubstituted 5-membered aromatic ring, a substituted or unsubstituted 6-membered aromatic ring, or a condensed ring of two or more, and G is $-(CR^dR^e)_n-$, $-O-$, $-S-$, $-Se-$, $-Te-$, $-N=$, $-NR^f-$, $-SiR^{gg}R^{hh}-$, $-GeR^iR^j-$, $-GeR^{ii}R^{jj}-$, $-(C(R^m)=C(R^n))-$, $-(C(R^{mm})=C(R^{nn}))-$, or a single bond, wherein $R^d$, $R^e$, $R^f$, $R^g$, $R^h$, $R^i$, $R^j$, $R^m$, and $R^n$ are each independently hydrogen, a halogen, a substituted or unsubstituted C1 to C10 alkyl group, or a substituted or unsubstituted C6 to C10 aryl group, at least one pair of $R^{gg}$ and $R^{hh}$, $R^{ii}$ and $R^{jj}$, or $R^{mm}$ and $R^{nn}$ is linked to each other to provide a ring structure, and n of $-(CR^dR^e)_n-$ is 1 or 2.

Chemical Formula 4-3 may be represented by Chemical Formula 4-3a, Chemical Formula 4-3b or Chemical Formula 4-3c.

[Chemical Formula 4-3a]

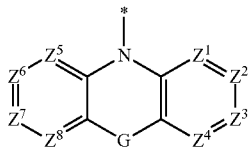

In Chemical Formula 4-3a,

G is the same as G in Chemical Formula 4-3, $Z^1$ to $Z^8$ are each independently N or $CR^x$, wherein $R^x$ is hydrogen, a C1 to C6 alkyl group, a C1 to C10 haloalkyl group, $-SiH_3$, a C1 to C10 alkylsilyl group, $-NH_2$, a C1 to C10 alkylamine group, a C6 to C12 aryl group, a C3 to C12 heteroaryl group, a halogen, a cyano group, or a combination thereof, when $Z^1$ to $Z^8$ are $CR^x$, $R^x$'s may be present independently or two adjacent ones of $Z^1$ to $Z^8$ may be linked to each other to provide a 5-membered aromatic ring or a 6-membered aromatic ring, and

* is a linking point with Chemical Formula 1.

[Chemical Formula 4-3b]

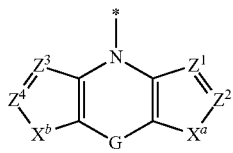

[Chemical Formula 4-3c]

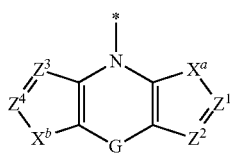

In Chemical Formula 4-3b and Chemical Formula 4-3c,

G is the same as G in Chemical Formula 4-3, $X^a$ and $X^b$ are each independently $-O-$, $-S-$, $-Se-$, $-Te-$, $-NR^p-$, $-SiR^qR^r-$, or $-GeR^sR^t-$, wherein $R^p$, $R^q$, $R^r$, $R^s$, and $R^t$ are each independently hydrogen, a halogen, a substituted or unsubstituted C1 to C10 alkyl group, or a substituted or unsubstituted C6 to C10 aryl group, $Z^1$ to $Z^4$ are each independently N or $CR^x$, wherein $R^x$ is hydrogen, a C1 to C6 alkyl group, a C1 to C10 haloalkyl group, $-SiH_3$, a C1 to C10 alkylsilyl group, $-NH_2$, a C1 to C10 alkylamine group, a C6 to C12 aryl group, a C3 to C12 heteroaryl group, a halogen, a cyano group, or a combination thereof, and when $Z^1$ to $Z^4$ are $CR^x$, $R^x$'s may be present independently or two adjacent ones of $Z^1$ to $Z^4$ may be linked to each other to provide a 5-membered aromatic ring or a 6-membered aromatic ring.

Chemical Formula 4-3a may be represented by one of Chemical Formula 4-3aa to Chemical Formula 4-3al.

[Chemical Formula 4-3aa to Chemical Formula 4-3al]

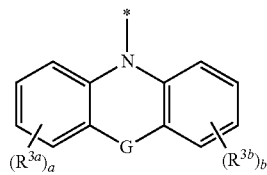
(4-3aa)

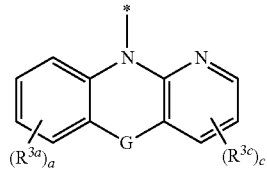
(4-3ab)

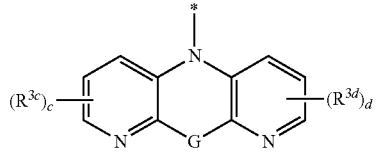
(4-3ac)

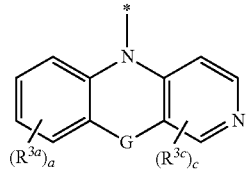
(4-3ad)

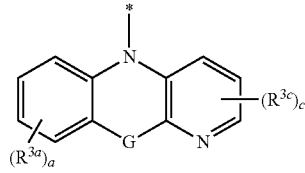
(4-3ae)

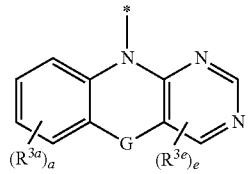
(4-3af)

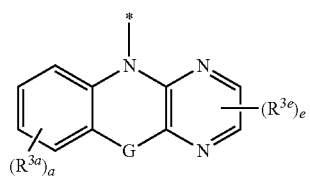
(4-3ag)

-continued

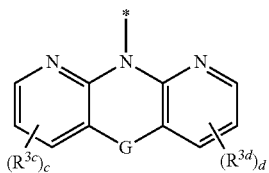
(4-3ah)

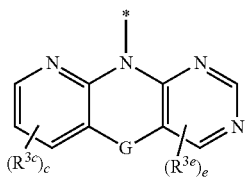
(4-3ai)

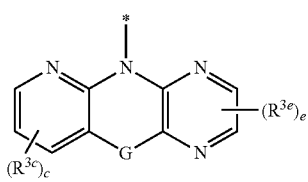
(4-3aj)

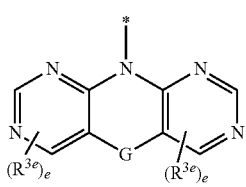
(4-3ak)

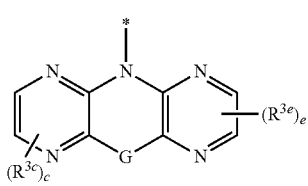
(4-3al)

In Chemical Formula 4-3aa to Chemical Formula 4-3al,
a and b are each independently an integer of 1 to 4,
c and d are each independently an integer of 1 to 3,
e is an integer of 1 or 2,
G is a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, and R$^i$ are each independently hydrogen, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or are linked to each other to provide a ring, and n of —(CR$^f$R$^g$)$_n$— is an integer of 1 or 2, and
R$^{1a}$ to Rae are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally when a, b, c, d, or e are 2 or more, two adjacent to each other among a plurality of R$^{3a}$'s, two adjacent to each other among a plurality of R$^{3b}$'s, a plurality of R$^{3d}$'s, two adjacent to each other among a plurality of R$^{3d}$'s, or two adjacent to each other among a plurality of R$^{3e}$'s may be linked to provide a 5-membered aromatic ring or a 6-membered aromatic ring or optionally two adjacent to each other among a R$^{5a}$ to R$^{5d}$ may be linked to provide a 5-membered aromatic ring or a 6-membered aromatic ring.

Ar$^1$ and Ar$^2$ of Chemical Formula 1 may be linked to each other to provide a condensed ring, and Ar$^2$ and R$^1$ of Chemical Formula 1 may be linked to each other to provide a condensed ring. In this case, Chemical Formula 1 may be represented by Chemical Formula 5.

[Chemical Formula 5]

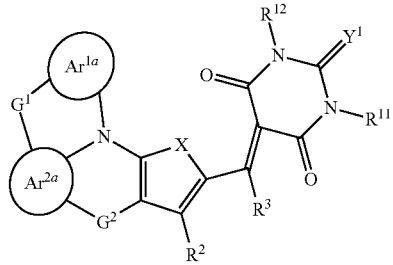

In Chemical Formula 5,
X, R$^2$, R$^3$, Y$^1$, R$^{11}$, and R$^{12}$ are the same as X, R$^2$, R$^3$, Y$^1$, R$^{11}$, and R$^{12}$, respectively, in Chemical Formula 1,
Ar$^{1a}$ and Ar$^{2a}$ are each independently a substituted or unsubstituted 5-membered aromatic ring, a substituted or unsubstituted 6-membered aromatic ring, or a condensed ring of two or more, and
G$^1$ and G$^2$ are each independently —(CR$^d$R$^e$)$_n$—, —O—, —S—, —Se—, —Te—, —N=, —NR$^f$—, —SiR$^g$R$^h$—, —SiR$^{gg}$R$^{hh}$—, —GeR$^i$R$^j$—, —GeR$^{ii}$R$^{jj}$—, —(C(R$^m$)=C(R$^n$))—, —(C(R$^{mm}$)=C(R$^{nn}$))—, or a single bond, wherein R$^d$, R$^e$, R$^f$, R$^g$, R$^h$, R$^i$, R$^j$, R$^m$, and R$^n$ are each independently hydrogen, a halogen, a substituted or unsubstituted C1 to C10 alkyl group, or a substituted or unsubstituted C6 to C10 aryl group, at least one pair of R$^{gg}$ and R$^{hh}$, R$^{ii}$ and R$^{jj}$, or R$^{mm}$ and R$^{nn}$ is linked to each other to provide a ring structure, and n of —(CR$^d$R$^e$)$_n$— is 1 or 2.

The compound may have a maximum absorption wavelength ($\lambda_{max}$) in a wavelength region of greater than or equal to about 500 nm and less than about 600 nm, in a thin film state.

The compound may exhibit a light absorption curve having a full width at half maximum (FWHM) of about 50 nm to about 120 nm, in a thin film state.

The compound may have an absorption coefficient of greater than or equal to about $5 \times 10^4$ cm$^{-1}$.

According to some example embodiments, a photoelectric device (e.g., organic photoelectric device) includes a first electrode and a second electrode facing each other and an active layer interposed between the first electrode and the second electrode and including the compound represented by Chemical Formula 1.

According to some example embodiments, an image sensor includes the photoelectric device.

The image sensor may include a semiconductor substrate integrated with a plurality of first photo-sensing devices configured to sense light in a blue wavelength region and a plurality of second photo-sensing devices configured to sense light in a red wavelength region, and the photoelectric device is on the semiconductor substrate and configured to selectively sense light in a green wavelength region.

The first photo-sensing devices and the second photo-sensing devices may be stacked in a vertical direction in the semiconductor substrate. Each first photo-sensing device may be stacked in the vertical direction with a separate second photo-sensing device.

The image sensor may further include a color filter layer including a blue filter configured to selectively transmit light in a blue wavelength region and a red filter configured to selectively transmit light in a red wavelength region.

The image sensor may include a green photoelectric device, configured to selectively absorb light in a green wavelength region, which is the photoelectric device, a blue photoelectric device configured to selectively absorb light in a blue wavelength region, and a red photoelectric device configured to selectively absorb light in a red wavelength region that are stacked.

According to some example embodiments, an electronic device includes the image sensor.

The compound may selectively absorb light in a green wavelength region and may have improved light absorption characteristics. The compound improves efficiency of a photoelectric device, an image sensor, and an electronic device based on increasing wavelength selectivity of the green wavelength region and absorption coefficient.

DETAILED DESCRIPTION

Figure 1:
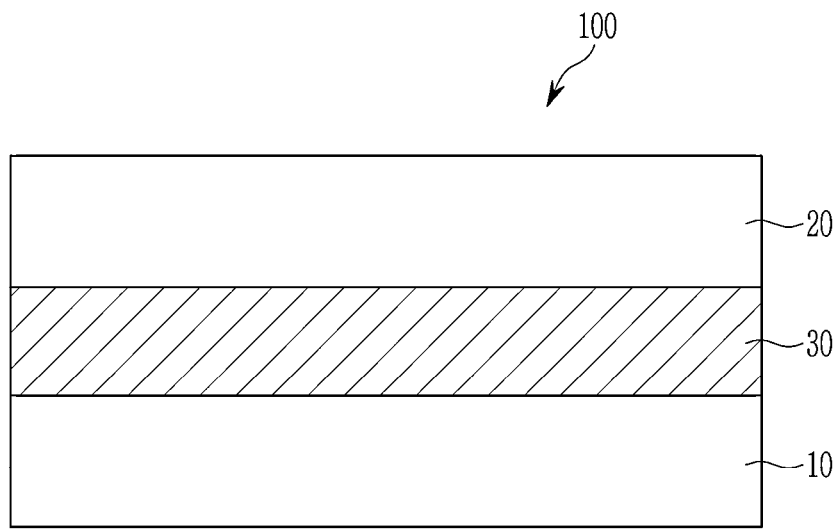
FIG. 1 is a cross-sectional view showing a photoelectric device according to some example embodiments.

Hereinafter, some example embodiments are described in detail so that those of ordinary skill in the art can easily implement them. However, a structure that is actually applied may be implemented in various different forms, and is not limited to the example embodiments described herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of some example embodiments, and the same or similar constituent elements are indicated by the same reference numeral throughout the specification.

As used herein, "at least one of A, B, or C," "one of A, B, C, or a combination thereof" and "one of A, B, C, and a combination thereof" refer to each constituent element, and a combination thereof (e.g., A; B; C; A and B; A and C; B and C; or A, B and C).

As used herein, when specific definition is not otherwise provided, "substituted" refers to replacement of a hydrogen of a compound or a functional group by a halogen atom (F, Br, Cl, or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C1 to C20 alkoxy group, a C2 to C20 alkenyl group, a C2 to C20 alkynyl group, a C6 to C30 aryl group, a C7 to C30 arylalkyl group, a C2 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, =S, or a combination thereof.

As used herein, when specific definition is not otherwise provided, "hetero" refers to one including 1 to 3 heteroatoms selected from N, O, S, Se, Te, P, and S.

As used herein, "alkyl group" refers to a monovalent linear or branched saturated hydrocarbon group, for example a methyl group, an ethyl group, a propyl group, an isopropyl group, an n-butyl group, an isobutyl group, a t-butyl group, a pentyl group, a hexyl group, and the like.

As used herein, "aryl group" refers to a substituent including all element of the functional group having p-orbitals which form conjugation, and may be a monocyclic, polycyclic or fused-ring polycyclic (e.g., rings sharing adjacent pairs of carbon atoms) functional group.

As used herein, "cycloalkyl group" refers to a monovalent hydrocarbon cyclic group in which the atoms of the cycle are carbon, for example a cyclopropyl group, a cyclobutyl group, a cyclopentyl group, or a cyclohexyl group.

As used herein, when a definition is not otherwise provided, "cyano-containing group" refers to a monovalent group such as a C1 to C30 alkyl group, a C2 to C30 alkenyl group, or a C2 to C30 alkynyl group where at least one hydrogen is substituted with a cyano group. As used herein, when a definition is not otherwise provided, the cyano-containing group also refers to a divalent group such as $=CR^{x'}-(CR^{x}R^{y})_p-CR^{y'}(CN)_2$ wherein $R^x$, $R^y$, $R^{x'}$, and $R^{y'}$ are independently hydrogen or a C1 to C10 alkyl group and p is an integer of 0 to 10 (or 1 to 10). Specific examples of the cyano-containing group may be a dicyanomethyl group, a dicyanovinyl group, a cyanoethynyl group, and the like. As used herein, the cyano-containing group does not include a functional group including a cyano group (—CN) alone.

As used herein, when a definition is not otherwise provided, "combination thereof" refers to at least two substituents bound to each other by a single bond or a C1 to C10 alkylene group, or at least two fused substituents.

As used herein, "hydrocarbon cyclic group" refers to a fused ring of an aromatic ring (arene ring) and a nonaromatic ring (alicyclic ring) and may include, for example a fused ring which is formed by linking at least one aromatic ring (arene ring) such as a C6 to C30 aryl group, a C6 to C20 aryl group, or a C6 to C10 aryl group with at least one nonaromatic ring (alicyclic ring) such as a C3 to C30 cycloalkyl group, a C3 to C20 cycloalkyl group, or a C3 to C10 cycloalkyl group.

As used herein, "heterocyclic group" refers to a cyclic group including a heteroatom selected from N, O, S, Se, Te, P, and Si instead of 1 to 3 carbon atoms in a cyclic group selected from an arene group (e.g., a C6 to C30 aryl group, a C6 to C20 aryl group, or a C6 to C10 aryl group), an alicyclic hydrocarbon group (e.g., a C3 to C30 cycloalkyl group, a C3 to C20 cycloalkyl group, or a C3 to C10 cycloalkyl group), or a fused ring thereof. At least one carbon atom of the heterocyclic group may also be substituted with a thiocarbonyl group (C=S).

As used herein, "arene group" refers to a hydrocarbon group having an aromatic ring, and includes monocyclic and polycyclic hydrocarbon groups, and the additional ring of the polycyclic hydrocarbon group may be an aromatic ring or a nonaromatic ring. "Heteroarene group" refers to an arene group including 1 to 3 heteroatoms selected from N, O, S, Se, Te, P, and Si in a cyclic group.

As used herein, "C6 to C30 aromatic hydrocarbon group" includes a C6 to C30 aryl group such as a phenyl group, a naphthyl group, a C6 to C30 arylene group, and the like, but is not limited thereto.

As used herein, "aliphatic hydrocarbon group" may include, for example, a C1 to C15 alkyl group such as a methyl group, an ethyl group, a propyl group, and the like, a C1 to C15 alkylene group, a C2 to C15 alkenyl group such as an ethenyl group or a propenyl group, a C2 to C15 alkynyl group such as an ethynyl group or a propynyl group, but is not limited thereto.

As used herein, "5-membered aromatic ring" refers to a 5-membered cyclic group (e.g., C5 aryl group) providing a conjugated structure or a 5-membered heterocyclic group (e.g., C2 to C4 heteroaryl group) providing a conjugated structure) but is not limited thereto. As used herein, "6-membered aromatic ring" refers to a 6-membered cyclic group (e.g., a C6 aryl group) providing a conjugated structure or a 6-membered heterocyclic group (e.g., a C2 to C5 heteroaryl group) providing a conjugated structure), but is not limited thereto. In addition, the aromatic ring may include the 5-membered aromatic ring or the 6-membered aromatic ring, but is not limited thereto.

Hereinafter, a compound according to some example embodiments is described. The compound is represented by Chemical Formula 1.

[Chemical Formula 1]

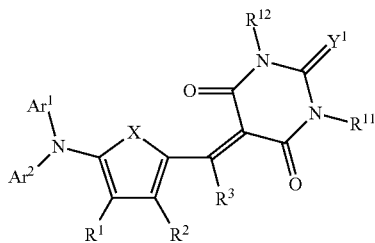

In Chemical Formula 1, $Ar^1$ and $Ar^2$ are each independently a substituted or unsubstituted 5-membered aromatic ring, a substituted or unsubstituted 6-membered aromatic ring, or a condensed ring of two or more, wherein $Ar^1$ and $Ar^2$ are each independently present or linked with each other to provide a condensed ring, X is S, Se, Te, O, S(=O), S(=O)$_2$, NR$^a$, or SiR$^b$R$^c$, wherein R$^a$, R$^b$, and R$^c$ are each independently hydrogen or a substituted or unsubstituted C1 to C10 alkyl group, $R^1$ to $R^3$ are each independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, wherein $R^1$ and $R^2$ are each independently present or linked with each other to provide a ring, $Y^1$ is O, S, Se, Te, or C(R$^e$)(CN), wherein R$^e$ is hydrogen, a cyano group (—CN), or a C1 to C10 alkyl group, and $R^{11}$ and $R^{12}$ are each independently hydrogen, deuterium, a C1 to C10 alkyl group (e.g., C1 to C6 alkyl group), or a C6 to C10 aryl group, wherein one of $R^{11}$ or $R^{12}$ is independently hydrogen or deuterium.

The compound represented by Chemical Formula 1 includes an electron donor moiety of an N-containing heteroaromatic ring, a linker including an X-containing 5-membered ring, and an electron acceptor moiety.

In Chemical Formula 1, the electron acceptor moiety is a cyclic group (e.g., a cyclic group of Chemical Formula 1) that is represented by Chemical Formula 2 including two carbonyl groups, and one of $R^{11}$ or $R^{12}$ is hydrogen or deuterium.

[Chemical Formula 2]

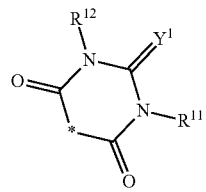

In Chemical Formula 2, $Y^1$, $R^{11}$, and $R^{12}$ are the same as $Y^1$, $R^{11}$, and $R^{12}$, respectively, in Chemical Formula 1.

In Chemical Formula 1, when either one of $R^{11}$ or $R^{12}$ is hydrogen or deuterium, compared with when two substituents of $R^{11}$ and $R^{12}$ are all hydrogen or deuterium or when two substituents of $R^{11}$ and $R^{12}$ are not hydrogen or deuterium, an absorption coefficient (absorption intensity) may be improved without changing an absorption wavelength.

Without being bound by a particular theory, when the two substituents of $R^{11}$ and $R^{12}$ are all hydrogen or deuterium, molecules may be extremely packed and thus agglomerated during formation of a film, and when either one of the two substituents of $R^{11}$ or $R^{12}$ is hydrogen or deuterium, the absorption intensity may be improved, while packing density is appropriately controlled.

In addition, in Chemical Formula 1, X of a linker including an X-containing 5-membered ring and oxygen (O) of a carbonyl group in an electron acceptor moiety (Chemical Formula 2) may increase an intramolecular interaction and thus improve the absorption intensity at a particular wavelength.

The cyclic group represented by Chemical Formula 2 may be, for example, a cyclic group represented by Chemical Formula 2-1, Chemical Formula 2-2, or Chemical Formula 2-3.

[Chemical Formula 2-1]

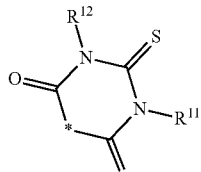

[Chemical Formula 2-2]

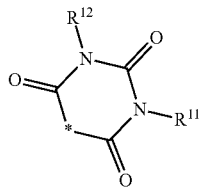

[Chemical Formula 2-3]

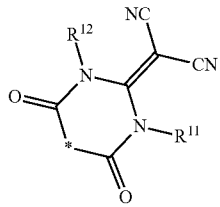

In Chemical Formula 2-1, Chemical Formula 2-2, and Chemical Formula 2-3, $R^{11}$ and $R^{12}$ are the same as $R^{11}$ and $R^{12}$, respectively, in Chemical Formula 1.

In the linker including the X-containing 5-membered ring, $R^1$ and $R^2$ may each independently exist or may combine with each other to provide a ring. When $R^1$ and $R^2$ are linked to each other (e.g., via a linker) to provide a ring, the linker may be represented by Chemical Formula 3-1 or Chemical Formula 3-2.

[Chemical Formula 3-1]

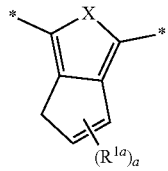

[Chemical Formula 3-2]

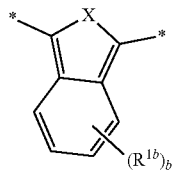

In Chemical Formula 3-1 and Chemical Formula 3-2, $R^{1a}$ and $R^{1b}$ is hydrogen, a C1 to C10 alkyl group, a C6 to C10 aryl group, a C2 to C10 heteroaryl group, or a halogen, and a and b are each independently an integer of 1 to 4.

In Chemical Formula 1, at least one of $Ar^1$ or $Ar^2$ may include a heteroatom selected from nitrogen (N), sulfur (S), and selenium (Se) at the $1^{st}$ position (e.g., a $1^{st}$ position of Chemical Formula 1). Herein, X, the oxygen (O) of a carbonyl group in an electron acceptor moiety, and at least one of $Ar^1$ or $Ar^2$ may increase the intramolecular interaction of a heteroatom at a position No. 1 and thus improve the absorption intensity at a particular wavelength.

In Chemical Formula 1, $Ar^1$ and $Ar^2$ may be a substituted or unsubstituted C6 to C30 aryl group, a substituted or unsubstituted C3 to C30 heteroaryl group, or a condensed ring thereof, or for example a substituted or unsubstituted C6 to C20 aryl group, a substituted or unsubstituted C3 to C20 heteroaryl group, or a condensed ring thereof.

In some example embodiments, the aryl group may be a phenyl group, a benzyl group, a naphthyl group, or an anthryl group, and the heteroaryl group may be a 2-pyrrolyl group, a 3-pyrrolyl group, a pyrazolyl group, an imidazolyl group, an oxazolyl group, an isoxazolyl group, a thiazolyl group, an isothiazolyl group, a pyridinyl group, a pyridazinyl group, a pyrimidinyl group, a pyrazinyl group, an indolyl group, a quinolinyl group, an isoquinolinyl group, a naphthyridinyl group, a cinnolinyl group, a quinazolinyl group, a phthalazinyl group, a benzotriazinyl group, a pyridopyrazinyl group, a pyridopyrimidinyl group, a pyridopyridazinyl group, a thienyl group, a benzothienyl group, a selenophenyl group, or a benzo selenophenyl group.

*—$N(Ar^1)(Ar^2)$ of Chemical Formula 1 may be represented by Chemical Formula 4-1.

[Chemical Formula 4-1]

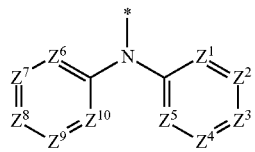

In Chemical Formula 4-1, $Z^1$ to $Z^{10}$ are each independently N or $CR^a$, wherein $R^a$ is hydrogen, a C1 to C6 alkyl group, a C1 to C10 haloalkyl group, —$SiH_3$, a C1 to C10 alkylsilyl group, —$NH_2$, a C1 to C10 alkylamine group, a C6 to C12 aryl group, a C3 to C12 heteroaryl group, a halogen, a cyano group, or a combination thereof, when $Z^1$ to $Z^{10}$ are $CR^a$, $R^a$'s may be present independently or two adjacent ones of $Z^1$ to $Z^{16}$ may be linked to each other to provide a 5-membered aromatic ring or a 6-membered aromatic ring, and is a linking point with Chemical Formula 1.

According to some example embodiments, in Chemical Formula 4-1, at least one of $Z^1$ to $Z^5$ and/or at least one of $Z^6$ to $Z^{16}$ may be N. According to some example embodiments, in Chemical Formula 4-1, at least two of $Z^1$ to $Z^5$ and/or at least two of $Z^6$ to $Z^{16}$ may be N.

Chemical Formula 4-1 may be represented by one of Chemical Formula 4-1a to Chemical Formula 4-11.

(4-1a)

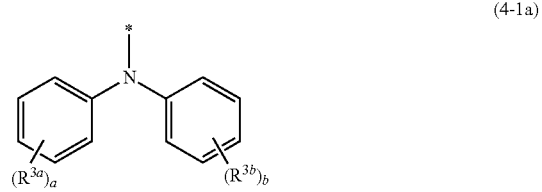

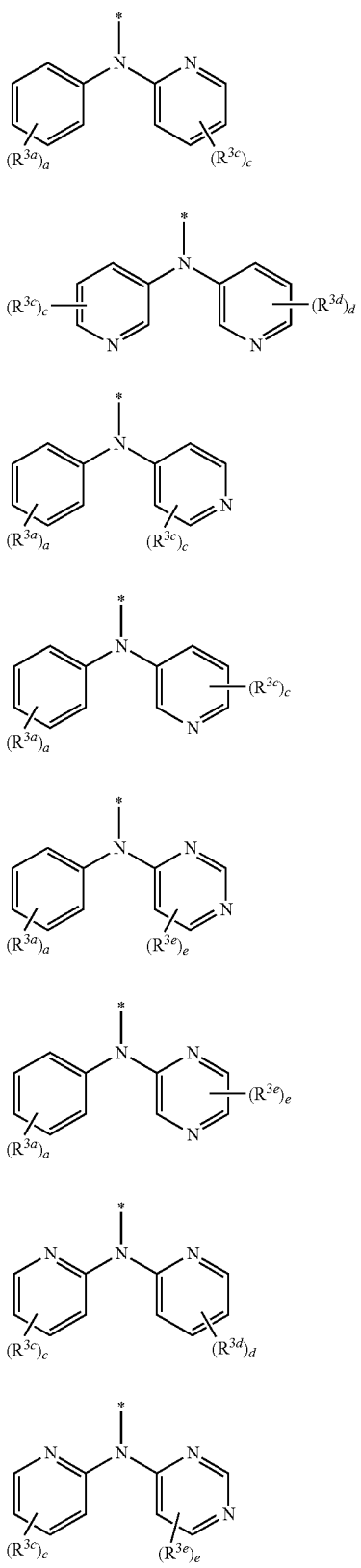
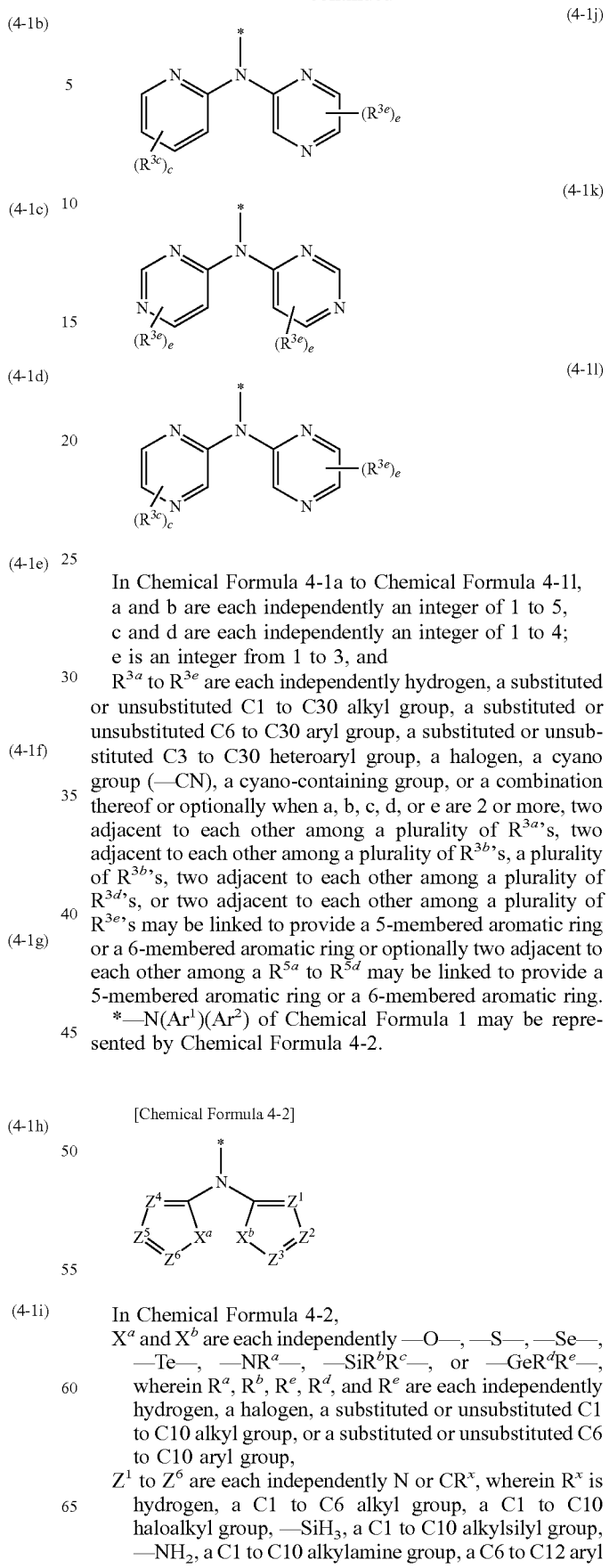

In Chemical Formula 4-1a to Chemical Formula 4-1l,
a and b are each independently an integer of 1 to 5,
c and d are each independently an integer of 1 to 4;
e is an integer from 1 to 3, and
$R^{3a}$ to $R^{3e}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally when a, b, c, d, or e are 2 or more, two adjacent to each other among a plurality of $R^{3a}$'s, two adjacent to each other among a plurality of $R^{3b}$'s, a plurality of $R^{3b}$'s, two adjacent to each other among a plurality of $R^{3d}$'s, or two adjacent to each other among a plurality of $R^{3e}$'s may be linked to provide a 5-membered aromatic ring or a 6-membered aromatic ring or optionally two adjacent to each other among a $R^{5a}$ to $R^{5d}$ may be linked to provide a 5-membered aromatic ring or a 6-membered aromatic ring.

*—N(Ar$^1$)(Ar$^2$) of Chemical Formula 1 may be represented by Chemical Formula 4-2.

[Chemical Formula 4-2]

In Chemical Formula 4-2,
$X^a$ and $X^b$ are each independently —O—, —S—, —Se—, —Te—, —NR$^a$—, —SiR$^b$R$^c$—, or —GeR$^d$R$^e$—, wherein R$^a$, R$^b$, R$^c$, R$^d$, and R$^e$ are each independently hydrogen, a halogen, a substituted or unsubstituted C1 to C10 alkyl group, or a substituted or unsubstituted C6 to C10 aryl group,
$Z^1$ to $Z^6$ are each independently N or CR$^x$, wherein R$^x$ is hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof, when $Z^1$ to $Z^6$ are $CR^x$, $R^x$'s may be present independently or two adjacent ones of $Z^1$ to $Z^6$ may be linked to each other to provide a 5-membered aromatic ring or a 6-membered aromatic ring, and

* is a linking point with Chemical Formula 1.

According to some example embodiments, in Chemical Formula 4-2, at least one of $Z^1$ to $Z^3$ and/or at least one of $Z^4$ to $Z^6$ may be N. According to some example embodiments, in Chemical Formula 4-2, at least two of $Z^1$ to $Z^3$ and/or at least two of $Z^4$ to $Z^6$ may be N.

When $Ar^1$ and $Ar^2$ of Chemical Formula 1 are linked to each other to form a condensed ring, *—$N(Ar^1)(Ar^2)$ may be represented by Chemical Formula 4-3.

[Chemical Formula 4-3]

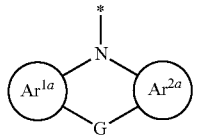

In Chemical Formula 4-3, $Ar^{1a}$ and $Ar^{2a}$ are each independently a substituted or unsubstituted 5-membered aromatic ring, a substituted or unsubstituted 6-membered aromatic ring, or a condensed ring of two or more, and G is —$(CR^dR^e)_n$—, —O—, —S—, —Se—, —Te—, —N=, —$NR^f$—, —$SiR^gR^h$—, —$SiR^{gg}R^{hh}$—, —$GeR^iR^j$—, —$GeR^{ii}R^{jj}$—, —$(C(R^m)=C(R^n))$—, —$(C(R^{mm})=C(R^{nn}))$—, or a single bond, wherein $R^d$, $R^e$, $R^f$, $R^g$, $R^h$, $R^i$, $R^j$, $R^m$, and $R^n$ are each independently hydrogen, a halogen, a substituted or unsubstituted C1 to C10 alkyl group, or a substituted or unsubstituted C6 to C10 aryl group, at least one pair of $R^{gg}$ and $R^{hh}$, $R^{ii}$ and $R^{jj}$, or $R^{mm}$ and $R^{nn}$ is linked to each other to provide a ring structure, and n of —$(CR^dR^e)_n$— is 1 or 2.

As in In Chemical Formula 4-3, $Ar^1$ and $Ar^2$ are linked by G to provide a single conjugation structure as a whole to improve the thermal stability of the compound. This conjugation structure may be formed by fusion of 3 to 4 5-membered or 6-membered aromatic rings, but is not limited thereto.

$Ar^{1a}$ and $Ar^{2a}$ may be a substituted or unsubstituted C6 to C30 arene group, a substituted or unsubstituted C3 to C30 heteroarene group, or a condensed ring thereof, or may be, for example, a substituted or unsubstituted a C6 to C20 arene group, a substituted or unsubstituted C3 to C20 heteroarene group, or a condensed ring thereof.

In some example embodiments, the arene group may be a benzene ring, a naphthalene ring, and an anthracene ring, and the heteroarene group may be selected from a pyrrole ring, a pyrazole ring, an imidazole ring, an oxazole ring, an isoxazole ring, a thiazole ring, an isothiazole ring, a pyridine ring, a pyridazine ring, a pyrimidine ring, a pyrazine ring, an indole ring, a quinoline ring, an isoquinoline ring, a naphthyridine ring, a cinnoline ring, a quinazoline ring, a phthalazine ring, a benzotriazine ring, a pyridopyrazine ring, a pyridopyrimidine ring, a pyridopyridazine ring, a thiophene ring, a benzothiophene ring, a selenophene ring, or a benzoselenophene ring.

Chemical Formula 4-3 may be represented by Chemical Formula 4-3a, Chemical Formula 4-3b, or Chemical Formula 4-3c.

[Chemical Formula 4-3a]

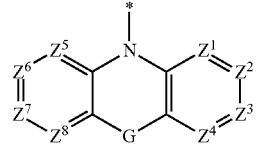

In Chemical Formula 4-3a,

G is the same as G in Chemical Formula 4-3, $Z^1$ to $Z^8$ are each independently N or $CR^x$, wherein $R^x$ is hydrogen, a C1 to C6 alkyl group, a C1 to C10 haloalkyl group, —$SiH_3$, a C1 to C10 alkylsilyl group, —$NH_2$, a C1 to C10 alkylamine group, a C6 to C12 aryl group, a C3 to C12 heteroaryl group, a halogen, a cyano group, or a combination thereof, when $Z^1$ to $Z^8$ are $CR^x$, $R^x$'s may be present independently or two adjacent ones of $Z^1$ to $Z^8$ may be linked to each other to provide a 5-membered aromatic ring or a 6-membered aromatic ring, and

* is a linking point with Chemical Formula 1.

According to some example embodiments, in Chemical Formula 4-3a, at least one of $Z^1$ to $Z^4$ and/or at least one of $Z^5$ to $Z^8$ may be N. According to some example embodiments, in Formula 4-3a, at least two of $Z^1$ to $Z^4$ and/or at least two of $Z^5$ to $Z^8$ may be N.

[Chemical Formula 4-3b]

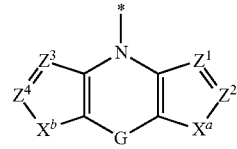

[Chemical Formula 4-3c]

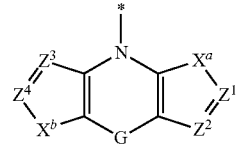

In Chemical Formula 4-3b and Chemical Formula 4-3c,

G is the same as G in Chemical Formula 4-3, $X^a$ and $X^b$ are each independently —O—, —S—, —Se—, —Te—, —$NR^p$—, —$SiR^qR^r$—, or —$GeR^sR^t$—, wherein $R^p$, $R^q$, $R^r$, $R^s$, and $R^t$ are each independently hydrogen, a halogen, a substituted or unsubstituted C1 to C10 alkyl group, or a substituted or unsubstituted C6 to C10 aryl group, $Z^1$ to $Z^4$ are each independently N or $CR^x$, wherein $R^x$ is hydrogen, a C1 to C6 alkyl group, a C1 to C10 haloalkyl group, —$SiH_3$, a C1 to C10 alkylsilyl group, —$NH_2$, a C1 to C10 alkylamine group, a C6 to C12 aryl group, a C3 to C12 heteroaryl group, a halogen, a cyano group, or a combination thereof, and when $Z^1$ to $Z^4$ are $CR^x$, $R^x$'s may be present independently or two adjacent ones of $Z^1$ to $Z^4$ may be linked to each other to provide a 5-membered aromatic ring or a 6-membered aromatic ring.

According to some example embodiments, in Chemical Formula 4-3b, at least one of $Z^1$ or $Z^2$ and/or at least one of $Z^3$ or $Z^4$ may be N. According to some example embodiments, in Chemical Formula 4-3b, $Z^1$ and $Z^2$ and/or $Z^3$ and $Z^4$ may be N.

According to some example embodiments, in Chemical Formula 4-3c, at least one of $Z^1$ or $Z^2$ and/or at least one of $Z^3$ or $Z^4$ may be N. According to some example embodiments, in Chemical Formula 4-3c, $Z^1$ and $Z^2$ and/or $Z^3$ and $Z^4$ may be N.

Chemical Formula 4-3a may be represented by one of Chemical Formula 4-3aa to Chemical Formula 4-3al.

[Chemical Formula 4-3aa to Chemical Formula 4-3al]

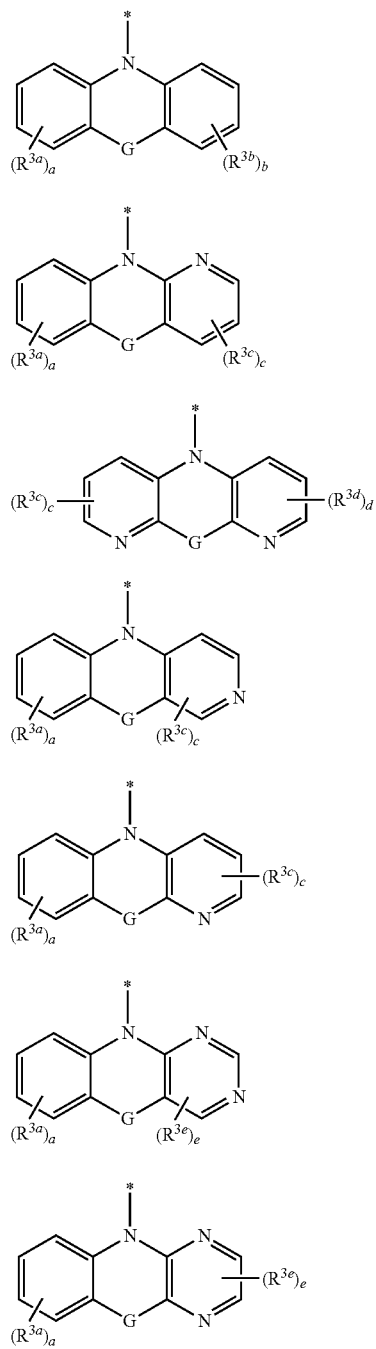
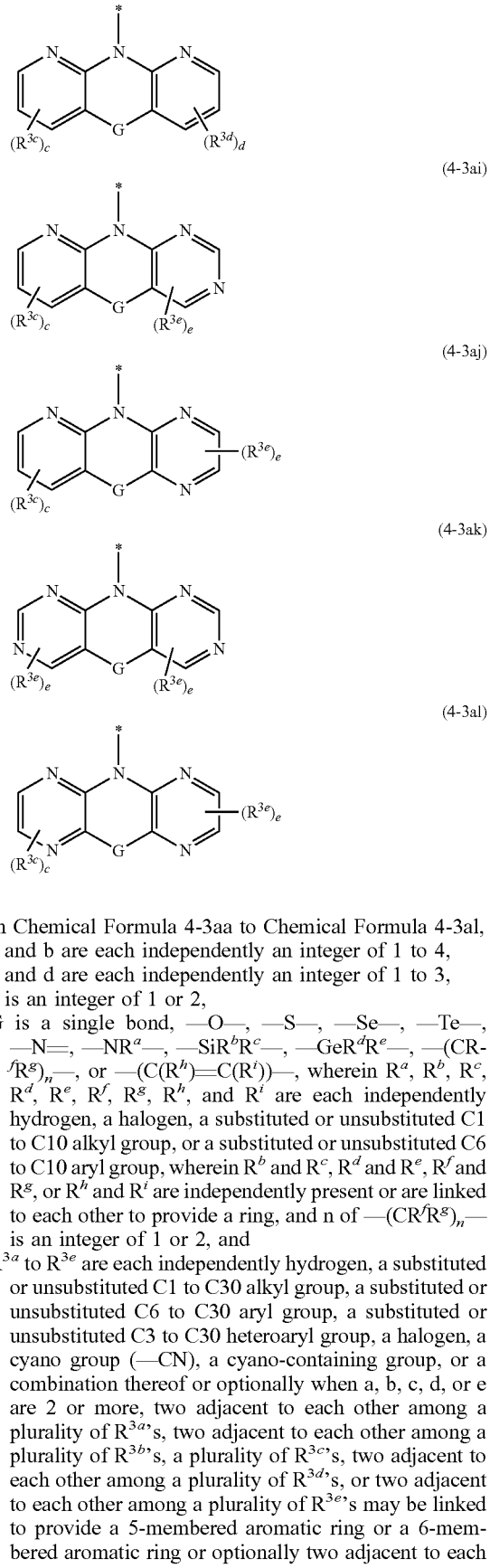

In Chemical Formula 4-3aa to Chemical Formula 4-3al,
a and b are each independently an integer of 1 to 4,
c and d are each independently an integer of 1 to 3,
e is an integer of 1 or 2,
G is a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ are each independently hydrogen, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or are linked to each other to provide a ring, and n of —(CR$^f$R$^g$)$_n$— is an integer of 1 or 2, and R$^{3a}$ to R$^{3e}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally when a, b, c, d, or e are 2 or more, two adjacent to each other among a plurality of R$^{3a}$'s, two adjacent to each other among a plurality of R$^{3b}$'s, a plurality of R$^{3c}$'s, two adjacent to each other among a plurality of R$^{3d}$'s, or two adjacent to each other among a plurality of R$^{3e}$'s may be linked to provide a 5-membered aromatic ring or a 6-membered aromatic ring or optionally two adjacent to each other among a $R^{5a}$ to $R^{5d}$ may be linked to provide a 5-membered aromatic ring or a 6-membered aromatic ring.

Chemical Formula 4-3aa may be represented by Chemical Formula 4-3aa-1.

[Chemical Formula 4-3aa-1]

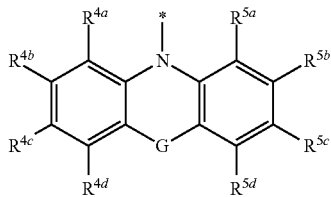

In Chemical Formula 4-3aa-1, $R^{4a}$ to $R^{4d}$ and $R^{5a}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent to each other among $R^{4a}$ to $R^{4d}$ may be linked to provide a 5-membered aromatic ring or a 6-membered aromatic ring or optionally two adjacent to each other among $R^{5a}$ to $R^{5d}$ may be linked to provide a 5-membered aromatic ring or a 6-membered aromatic ring, G is —($CR^dR^e$)$_n$—, —O—, —S—, —Se—, —Te—, —N═, —$NR^f$—, —$SiR^gR^h$—, —$SiR^{gg}R^{hh}$—, —$GeR^iR^j$—, —$GeR^{ii}R^{jj}$—, —(C($R^m$)═C($R^n$))—, —(C($R^{mm}$)═C($R^{nn}$))—, or a single bond, wherein $R^d$, $R^e$, $R^f$, $R^g$, $R^h$, $R^i$, $R^j$, $R^m$, and $R^n$ are each independently hydrogen, a halogen, a substituted or unsubstituted C1 to C10 alkyl group, or a substituted or unsubstituted C6 to C10 aryl group, at least one pair of $R^{gg}$ and $R^{hh}$, $R^{ii}$ and $R^{jj}$, or $R^{mm}$ and $R^{nn}$ is linked to each other to provide a ring structure, and n of —($CR^dR^e$)$_n$— is 1 or 2.

The ring structure formed by linking at least one pair of $R^{gg}$ and $R^{hh}$, $R^{ii}$ and $R^{jj}$, or $R^{mm}$ and $R^{nn}$ to each other may be a spiro structure or a fused ring, and may have a 5-membered or 6-membered ring structure. In addition, it may optionally include at least one heteroatom selected from N, O, S, Se, Te, P, and Si in the ring structure.

In Chemical Formula 4-3aa-1, when G is —$SiR^gR^h$—, —$GeR^iR^j$—, or —(C($R^m$)═C($R^n$))—, Chemical Formula 4-3aa-1 may be represented by Chemical Formula 4-3aa-11, Chemical Formula 4-3aa-12, or Chemical Formula 4-3aa-13.

[Chemical Formula 4-3aa-11]

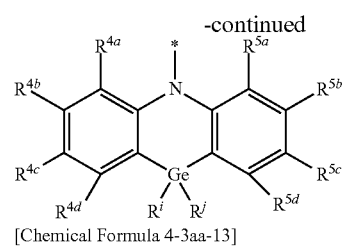

[Chemical Formula 4-3aa-12]

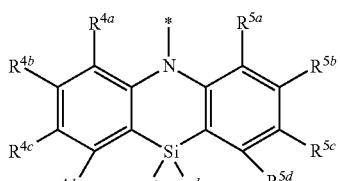

[Chemical Formula 4-3aa-13]

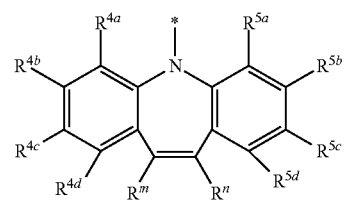

In Chemical Formula 4-3aa-11, Chemical Formula 4-3aa-12 or Chemical Formula 4-3aa-13, $R^{4a}$ to $R^{4d}$ and $R^{5a}$ to $R^{5d}$ are the same as $R^{4a}$ to $R^{4d}$ and $R^{5a}$ to $R^{5d}$, respectively, in Chemical Formula 4-3aa-1, and $R^g$, $R^h$, $R^i$, $R^j$, $R^m$, and $R^n$ are each independently hydrogen, a halogen, a substituted or unsubstituted C1 to C10 alkyl group, or a substituted or unsubstituted C6 to C10 aryl group.

In Chemical Formula 4-3aa-1, when G is —$SiR^{gg}R^{hh}$—, —$GeR^{ii}R^{jj}$, or —(C($R^{mm}$)═C($R^{nn}$))—, Chemical Formula 4-3aa-1 may be represented by Chemical Formula 4-3aa-14, Chemical Formula 4-3aa-15, or Chemical Formula 4-3aa-16.

[Chemical Formula 4-3aa-14]

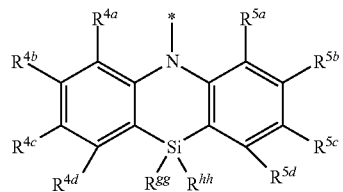

[Chemical Formula 4-3aa-15]

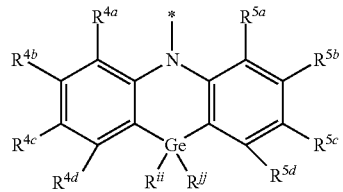

[Chemical Formula 4-3aa-16]

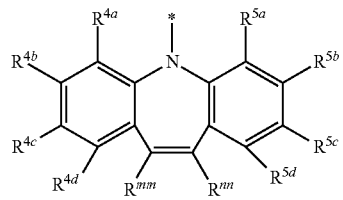

In Chemical Formula 4-3aa-14, Chemical Formula 4-3aa-15 or Chemical Formula 4-3aa-16, $R^{4a}$ to $R^{4d}$ and $R^{5a}$ to $R^{5d}$ are the same as $R^{4a}$ to $R^{4d}$ and $R^{5a}$ to $R^{5d}$, respectively, in Chemical Formula 4-3aa-1

$R^{gg}$, $R^{hh}$, $R^{ii}$, $R^{mm}$, and $R^{nn}$ are each independently a substituted or unsubstituted C1 to C10 alkyl group, or a substituted or unsubstituted C6 to C10 aryl group, or at least one pair of $R^{gg}$ and $R^{hh}$, $R^{ii}$ and $R^{jj}$, or $R^{mm}$ and $R^{nn}$ is linked to each other to provide a ring structure.

The ring structure formed by linking at least one pair of $R^{gg}$ and $R^{hh}$, $R^{ii}$ and $R^{jj}$, or $R^{mm}$ and $R^{nn}$ to each other may be a spiro structure or a fused ring, and may have a 5-membered or 6-membered ring structure. In addition, it may optionally include at least one heteroatom selected from N, O, S, Se, Te, P, and Si in the ring structure.

Although an example of the specific structure of Chemical Formula 4-3aa is provided above, examples of the specific structures of Chemical Formula 4-3ab to Chemical Formula 4-3al may also be provided in the same manner as Chemical Formula 4-3aa. That is, Chemical Formula 4-3ab may be represented by Chemical Formula 4-3ab-1, Chemical Formula 4-3ac may be represented by Chemical Formula 4-3ac-1, Chemical Formula 4-3ad may be represented by Chemical Formula 4-3ad-1, and Chemical Formula 4-3ae may be represented by Chemical Formula 4-3ae-1.

[Chemical Formula 4-3ab-1]

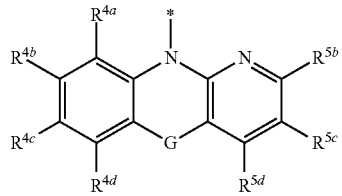

In Chemical Formula 4-3ab-1,

G is the same as G in Chemical Formula 4-3, $R^{4a}$ to $R^{4d}$ and $R^{5b}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent to each other among $R^{4a}$ to $R^{4d}$ may be linked to provide a 5-membered aromatic ring or a 6-membered aromatic ring or optionally two adjacent to each other among $R^{5b}$ to $R^{5d}$ may be linked to provide a 5-membered aromatic ring or a 6-membered aromatic ring.

[Chemical Formula 4-3ac-1]

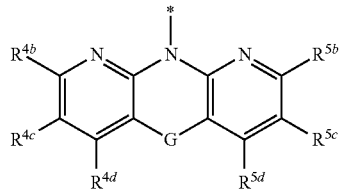

In Chemical Formula 4-3ac-1,

G is the same as G in Chemical Formula 4-3, $R^{4b}$ to $R^{4d}$ and $R^{5b}$ to $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent to each other among $R^{4b}$ to $R^{4d}$ may be linked to provide a 5-membered aromatic ring or a 6-membered aromatic ring or optionally two adjacent to each other among $R^{5b}$ to $R^{5d}$ may be linked to provide a 5-membered aromatic ring or a 6-membered aromatic ring.

[Chemical Formula 4-3ad-1]

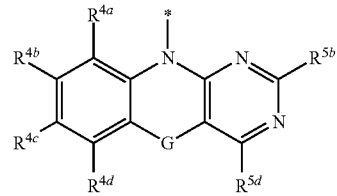

In Chemical Formula 4-3ad-1,

G is the same as G in Chemical Formula 4-3, and $R^{4a}$ to $R^{4d}$ and $R^{5b}$ and $R^{5d}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent to each other among $R^{4a}$ to $R^{4d}$ may be linked to provide a 5-membered aromatic ring or a 6-membered aromatic ring.

[Chemical Formula 4-3ae-1]

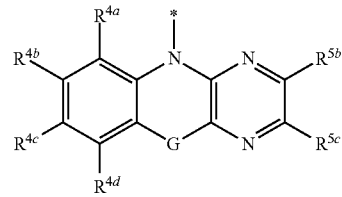

In Chemical Formula 4-3ae-1,

G is the same as G in Chemical Formula 4-3, and $R^{4a}$ to $R^{4d}$ and $R^{5b}$ and $R^{5c}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally two adjacent to each other among $R^{4a}$ to $R^{4d}$ may be linked to provide a 5-membered aromatic ring or a 6-membered aromatic ring or optionally two adjacent to each other among $R^{5b}$ and $R^{5c}$ may be linked to provide a 5-membered aromatic ring or a 6-membered aromatic ring.

$Ar^1$ and $Ar^2$ of Chemical Formula 1 may be linked to each other to provide a condensed ring, and $Ar^2$ and $R^1$ may be linked to each other to provide a condensed ring. In this case, Chemical Formula 1 may be represented by Chemical Formula 5.

[Chemical Formula 5]

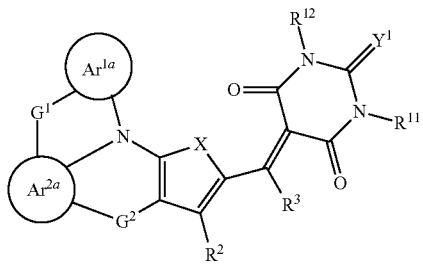

In Chemical Formula 5,

X, $R^2$, $R^3$, $Y^1$, $R^{11}$, and $R^{12}$ are the same as X, $R^2$, $R^3$, $Y^1$, $R^{11}$, and $R^{12}$, respectively, in Chemical Formula 1, $Ar^{1a}$ and $Ar^{2a}$ are each independently a substituted or unsubstituted 5-membered aromatic ring, a substituted or unsubstituted 6-membered aromatic ring, or a condensed ring of two or more, and $G^1$ and $G^2$ are each independently $-(CR^dR^e)_n-$, $-O-$, $-S-$, $-Se-$, $-Te-$, $-N=$, $-NR^f-$, $-SiR^gR^h-$, $-SiR^{gg}R^{hh}-$, $-GeR^iR^j-$, $-GeR^{ii}R^{jj}-$, $-(C(R^m)=C(R^n))-$, $-(C(R^{mm})=C(R^{nnn}))-$, or a single bond, wherein $R^d$, $R^e$, $R^f$, $R^g$, $R^h$, $R^i$, $R^j$, $R^m$, and $R^n$ are each independently hydrogen, a halogen, a substituted or unsubstituted C1 to C10 alkyl group, or a substituted or unsubstituted C6 to C10 aryl group, at least one pair of $R^{gg}$ and $R^{hh}$, $R^{ii}$ and $R^{jj}$, or $R^{mm}$ and $R^{nnn}$ is linked to each other to provide a ring structure, and n of $-(CR^dR^e)_n-$ is 1 or 2.

The compound of Chemical Formula 5 may be represented by Chemical Formula 5-1.

[Chemical Formula 5-1]

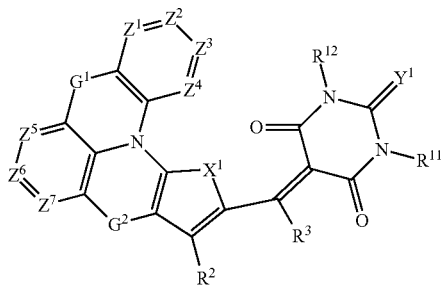

In Chemical Formula 5-1,

X, $R^2$, $R^3$, $Y^1$, $R^{11}$, and $R^{12}$ are the same as X, $R^2$, $R^3$, $Y^1$, $R^{11}$, and $R^{12}$, respectively, in Chemical Formula 1, $G^1$ and $G^2$ are the same as $G^1$ and $G^2$, respectively, in Chemical Formula 5, $Z^1$ to $Z^7$ are each independently N or $CR^k$, wherein $R^k$ is hydrogen, deuterium, a halogen, a cyano group, a cyano group, a nitro group, a hydroxyl group, an amine group, a substituted or unsubstituted C1 to C10 alkyl group, or a substituted or unsubstituted C1 to C10 alkoxy group or adjacent $R^k$'s are linked to provide a substituted or unsubstituted C6 to C30 arene group, a substituted or unsubstituted C3 to C30 heteroarene group, or a condensed ring thereof.

In Chemical Formula 5-1, $Z^4$ may be N or $CR^k$, wherein $R^k$ is a halogen, a cyano group, a C1 to C10 haloalkyl group, or a C1 to C10 cyanoalkyl group; or $Z^7$ may be N or $CR^k$, wherein $R^k$ is a halogen, a cyano group, a C1 to C10 haloalkyl group, or a C1 to C10 cyanoalkyl group, and $G^2$ is $-O-$, $-S-$, $-Se-$, $-Te-$, $-S(=O)-$, $-S(=O)_2-$, $-NR^{a1}-$, $-BR^{a2}-$, $-SiR^bR^c-$, $-GeR^dR^e-$, $-(CR^fR^g)_{n1}-$, $-(C(R^m)=C(R^n))-$, or $-(C(R^p)=N)-$, wherein $R^{a1}$, $R^{a2}$, $R^b$, $R^c$, $R^d$, $R^e$, $R^f$, $R^g$, $R^m$, $R^n$, and $R^p$ are each independently a halogen, a C1 to C20 haloalkyl group, or a C1 to C20 cyanoalkyl group, wherein n1 in $-(CR^fR^g)_{n1}-$ is 1 or 2.

In Chemical Formula 5-1, when $Z^1$ and $Z^5$ are $CR^k$, $G^1$ and at least one of $Z^1$ or $Z^5$ may be linked to each other to provide a fused ring.

The compound of Chemical Formula 5 may be represented by Chemical Formula 5-2.

[Chemical Formula 5-2]

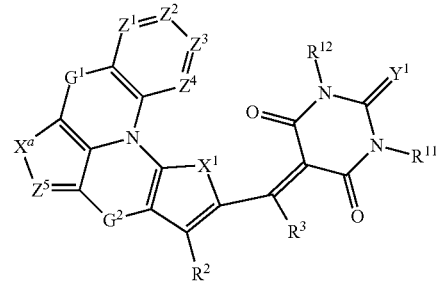

In Chemical Formula 5-2,

X, $R^2$, $R^3$, $Y^1$, $R^{11}$, and $R^{12}$ are the same as X, $R^2$, $R^3$, $Y^1$, $R^{11}$, and $R^{12}$, respectively, in Chemical Formula 1, $G^1$ and $G^2$ are the same as $G^1$ and $G^2$, respectively, in Chemical Formula 5, $Z^1$ to $Z^5$ are each independently N or $CR^k$, wherein $R^k$ is hydrogen, deuterium, a halogen, a cyano group, a nitro group, a hydroxyl group, an amine group, a substituted or unsubstituted C1 to C10 alkyl group or a substituted or unsubstituted C1 to C10 alkoxy group or adjacent $R^k$'s are linked to provide a substituted or unsubstituted C6 to C30 arene group, a substituted or unsubstituted C3 to C30 heteroarene group, or a condensed ring thereof, and $X^a$ is $-O-$, $-S-$, $-Se-$, $-Te-$, $-S(=O)-$, $-S(=O)_2-$, $-NR^{a1}-$, $-BR^{a2}-$, $-SiR^bR^c-$, $-SiR^{bb}R^{cc}-$, $-GeR^dR^e-$, $-GeR^{dd}R^{ee}-$, $-CR^fR^g-$, or $-CR^{ff}R^{gg}-$, wherein $R^{a1}$, $R^{a2}$, $R^b$, $R^c$, $R^d$, $R^e$, $R^f$, and $R^g$ are each independently hydrogen, deuterium, a halogen, a cyano group, a substituted or unsubstituted C1 to C20 alkyl group, a substituted or unsubstituted C1 to C20 alkoxy group, a substituted or unsubstituted C6 to C20 aryl group, a substituted or unsubstituted C6 to C20 aryloxy group, or a substituted or unsubstituted C3 to C20 heteroaryl group, and at least one pair of $R^{bb}$ and $R^{cc}$, $R^{dd}$ and $R^{ee}$, or $R^{ff}$ and $R^{gg}$ is linked to each other to provide a ring structure.

In Chemical Formula 5-2, $Z^4$ may be N or $CR^k$, wherein $R^k$ is a halogen, a cyano group, a C1 to C10 haloalkyl group, or a C1 to C10 cyanoalkyl group; or $Z^5$ may be N or $CR^k$, wherein $R^k$ is a halogen, a cyano group, a C1 to C10 haloalkyl group, or a C1 to C10 cyanoalkyl group and $G^2$ may be $-O-$, $-S-$, $-Se-$, $-Te-$, $-S(=O)-$, $-S(=O)_2-$, $-NR^{a1}-$, $-BR^{a2}-$, $-SiR^bR^c-$, $-GeR^dR^e-$, $-(CR^fR^g)_{n1}-$, $-(C(R^m)=C(R^n))-$, or $-(C(R^p)$ =N)—, wherein $R^{a1}$, $R^{a2}$, $R^b$, $R^c$, $R^d$, $R^e$, $R^f$, $R^g$, $R^m$, $R^n$, and $R^p$ may each independently be a halogen, a C1 to C20 haloalkyl group, or a C1 to C20 cyanoalkyl group, wherein n1 in —$(CR^fR^g)_{n1}$— is 1 or 2.

In Chemical Formula 5-2, $X^a$ (—$NR^{a1}$—, —$BR^{a2}$—, —$SiR^bR^c$—, —$GeR^dR^e$—, or —$CR^fR^g$—) and $G^1$ may be linked to each other to provide a fused ring.

The compound of Chemical Formula 5 may be represented by Chemical Formula 5-3.

[Chemical Formula 5-3]

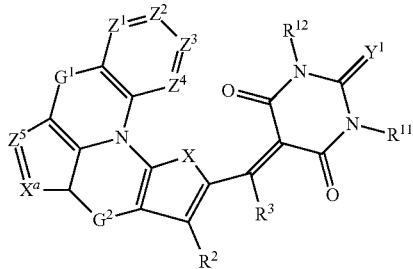

In Chemical Formula 5-3,

X, $R^2$, $R^3$, $Y^1$, $R^{11}$, and $R^{12}$ are the same as X, $R^2$, $R^3$, $Y^1$, $R^{11}$, and $R^{12}$, respectively, in Chemical Formula 1, $G^1$ and $G^2$ are the same as $G^1$ and $G^2$, respectively, in Chemical Formula 5, $Z^1$ to $Z^5$ are each independently N or $CR^k$, wherein $R^k$ is hydrogen, deuterium, a halogen, a cyano group, a nitro group, a hydroxyl group, an amine group, a substituted or unsubstituted C1 to C10 alkyl group or a substituted or unsubstituted C1 to C10 alkoxy group or adjacent $R^k$'s are linked to provide a substituted or unsubstituted C6 to C30 arene group, a substituted or unsubstituted C3 to C30 heteroarene group, or a condensed ring thereof, and $X^a$ is —O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$CR^fR^g$—, or —$CR^{ff}R^{gg}$—, wherein $R^{a1}$, $R^{a2}$, $R^b$, $R^c$, $R^d$, $R^e$, $R^f$, and $R^g$ are each independently hydrogen, deuterium, a halogen, a cyano group, a substituted or unsubstituted C1 to C20 alkyl group, a substituted or unsubstituted C1 to C20 alkoxy group, a substituted or unsubstituted C6 to C20 aryl group, a substituted or unsubstituted C6 to C20 aryloxy group, or a substituted or unsubstituted C3 to C20 heteroaryl group, and at least one pair of $R^{bb}$ and $R^{cc}$, $R^{dd}$ and $R^{ee}$, or $R^{ff}$ and $R^{gg}$ is linked to each other to provide a ring structure.

In Chemical Formula 5-3, $Z^4$ may be N or $CR^k$, wherein $R^k$ is a halogen, a cyano group, a C1 to C10 haloalkyl group, or a C1 to C10 cyanoalkyl group, or $X^a$ may be —O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, or —$CR^fR^g$—, wherein $R^{a1}$, $R^{a2}$, $R^b$, $R^c$, $R^d$, $R^e$, $R^f$, and $R^g$ are each independently a halogen, a C1 to C20 haloalkyl group, or a C1 to C20 cyanoalkyl group and $G^2$ may be —O—, —S—, —Se—, —Te—, —S(=O)—, —S(=O)$_2$—, —$NR^{a1}$—, —$BR^{a2}$—, —$SiR^bR^c$—, —$GeR^dR^e$—, —$(CR^fR^g)_{n1}$—, —$(C(R^m)=C(R^n))$—, or —$(C(R^p)$=N)—, wherein $R^{a1}$, $R^{a2}$, $R^b$, $R^c$, $R^d$, $R^e$, $R^f$, $R^g$, $R^m$, $R^n$, and $R^p$ are each independently a halogen, a C1 to C20 haloalkyl group, or a C1 to C20 cyanoalkyl group, wherein n1 in —$(CR^fR^g)_{n1}$— is 1 or 2.

In Chemical Formula 5-3, when $Z^5$ is $CR^k$, $Z^5$ and $G^2$ may be linked to each other and thus form a fused ring.

The compound of Chemical Formula 5 may be represented by Chemical Formula 5-4.

[Chemical Formula 5-4]

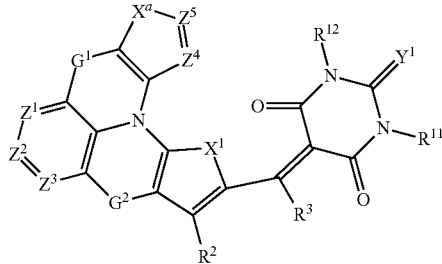

In Chemical Formula 5-4,

X, $R^2$, $R^3$, $Y^1$, $R^{11}$ and $R^{12}$ are the same as X, $R^2$, $R^3$, $Y^1$, $R^{11}$ and $R^{12}$, respectively, in Chemical Formula 1, $G^1$ and $G^2$ are the same as $G^1$ and $G^2$, respectively, in Chemical Formula 5, $Z^1$ to $Z^5$ are each independently N or $CR^k$, wherein $R^k$ is hydrogen, deuterium, a halogen, a cyano group, a nitro group, a hydroxyl group, an amine group, a substituted or unsubstituted C1 to C10 alkyl group or a substituted or unsubstituted C1 to C10 alkoxy group or adjacent $R^k$'s are linked to provide a substituted or unsubstituted C6 to C30 arene group, a substituted or unsubstituted C3 to C30 heteroarene group, or a condensed ring thereof, and $X^a$ is —O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$CR^fR^g$—, or —$CR^{ff}R^{gg}$—, wherein $R^{a1}$, $R^{a2}$, $R^b$, $R^c$, $R^d$, $R^e$, $R^f$, and $R^g$ are each independently hydrogen, deuterium, a halogen, a cyano group, a substituted or unsubstituted C1 to C20 alkyl group, a substituted or unsubstituted C1 to C20 alkoxy group, a substituted or unsubstituted C6 to C20 aryl group, a substituted or unsubstituted C6 to C20 aryloxy group or a substituted or unsubstituted C3 to C20 heteroaryl group, and at least one pair of $R^{bb}$ and $R^{cc}$, $R^{dd}$ and $R^{ee}$, or $R^{ff}$ and $R^{gg}$ is linked to each other to provide a ring structure.

In Chemical Formula 5-4, $Z^4$ may be N or $CR^k$, wherein $R^k$ is a halogen, a cyano group, a C1 to C10 haloalkyl group, or a C1 to C10 cyanoalkyl group; or $Z^3$ may be N or $CR^k$, wherein $R^k$ is a halogen, a cyano group, a C1 to C10 haloalkyl group, or a C1 to C10 cyanoalkyl group; $G^2$ may be —O—, —S—, —Se—, —Te—, —S(=O)—, —S(=O)$_2$—, —$NR^{a1}$—, —$BR^{a2}$—, —$SiR^bR^c$—, —$GeR^dR^e$—, —$(CR^fR^g)_{n1}$—, —$(C(R^m)=C(R^n))$—, or —$(C(R^p)$=N)— (wherein $R^{a1}$, $R^{a2}$, $R^b$, $R^c$, $R^d$, $R^e$, $R^f$, $R^g$, $R^m$, $R^n$, and $R^p$ may be independently halogen, a C1 to C20 haloalkyl group, or a C1 to C20 cyanoalkyl group), wherein n1 in —$(CR^fR^g)_{n1}$— is 1 or 2.

In Chemical Formula 5-4, when $Z^1$ is $CR^k$, $Z^1$ and $G^1$ may be linked to each other and thus form a fused ring.

The compound of Chemical Formula 5 may be represented by Chemical Formula 5-5.

[Chemical Formula 5-5]

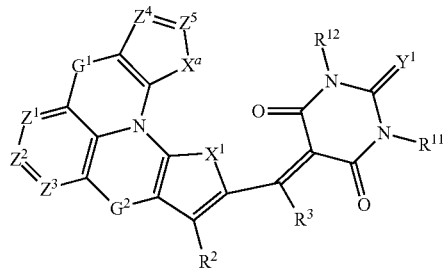

In Chemical Formula 5-5,

X, $R^2$, $R^3$, $Y^1$, $R^{11}$ and $R^{12}$ are the same as X, $R^2$, $R^3$, $Y^1$, $R^{11}$ and $R^{12}$, respectively, in Chemical Formula 1, $G^1$ and $G^2$ are the same as $G^1$ and $G^2$, respectively, in Chemical Formula 5, $Z^1$ to $Z^5$ are each independently N or $CR^k$, wherein $R^k$ is hydrogen, deuterium, a halogen, a cyano group, a nitro group, a hydroxyl group, an amine group, a substituted or unsubstituted C1 to C10 alkyl group or a substituted or unsubstituted C1 to C10 alkoxy group or adjacent $R^k$'s are linked to provide a substituted or unsubstituted C6 to C30 arene group, a substituted or unsubstituted C3 to C30 heteroarene group, or a condensed ring thereof, and $X^a$ is —O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$CR^fR^g$—, or —$CR^{ff}R^{gg}$—, wherein $R^{a1}$, $R^{a2}$, $R^b$, $R^c$, $R^d$, $R^e$, $R^f$, and $R^g$ are each independently hydrogen, deuterium, a halogen, a cyano group, a substituted or unsubstituted C1 to C20 alkyl group, a substituted or unsubstituted C1 to C20 alkoxy group, a substituted or unsubstituted C6 to C20 aryl group, a substituted or unsubstituted C6 to C20 aryloxy group, or a substituted or unsubstituted C3 to C20 heteroaryl group, and at least one pair of $R^{bb}$ and $R^{cc}$, $R^{dd}$ and $R^{ee}$, or $R^{ff}$ and $R^{gg}$ is linked to each other to provide a ring structure.

In Chemical Formula 5-3, $X^a$ may be —O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, or —$CR^fR^g$—, wherein $R^{a1}$, $R^{a2}$, $R^b$, $R^c$, $R^d$, $R^e$, $R^f$, and $R^g$ are each independently a halogen, a C1 to C20 haloalkyl group, or a C1 to C20 cyanoalkyl group, or $Z^3$ may be N or $CR^k$, wherein $R^k$ is a halogen, a cyano group, a C1 to C10 haloalkyl group, or a C1 to C10 cyanoalkyl group and $G^2$ may be —O—, —S—, —Se—, —Te—, —S(=O)—, —S(=O)$_2$—, —$NR^{a1}$—, —$BR^{a2}$—, —$SiR^bR^c$—, —$GeR^dR^e$—, —$(CR^fR^g)_{n1}$—, —$(C(R^m)=C(R^n))$—, or —$(C(R^p)=N)$—, wherein $R^{a1}$, $R^{a2}$, $R^b$, $R^c$, $R^d$, $R^e$, $R^f$, $R^g$, $R^m$, $R^n$, and $R^p$ are each independently a halogen, a C1 to C20 haloalkyl group, or a C1 to C20 cyanoalkyl group, wherein n1 in —$(CR^fR^g)_{n1}$— is 1 or 2.

In Chemical Formula 5-5, when $Z^1$ and $Z^4$ are $CR^k$, $G^1$ and one of $Z^1$ or $Z^4$ may be linked to each other to provide a fused ring.

The fused ring may be a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 heterocycloalkene group, or a condensed ring thereof.

In X of Chemical Formula 1 and $G^1$ and $G^2$ of Chemical Formula 5, the ring structure may be a spiro structure or a fused ring structure.

The spiro structure may include a moiety represented by Chemical Formula 6.

[Chemical Formula 6]

 (1)

 (2)

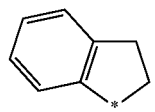 (3)

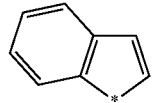 (4)

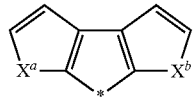 (5)

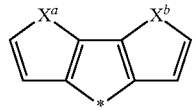 (6)

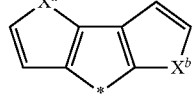 (7)

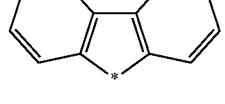 (8)

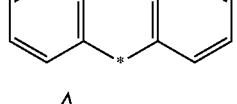 (9)

 (10)

In Chemical Formula 6, $X^a$ and $X^b$ are each independently —O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, or —$GeR^{dd}R^{ee}$—, wherein $R^{a1}$, $R^{a2}$, $R^b$, $R^c$, $R^d$, and $R^e$ are each independently hydrogen, deuterium, a halogen, a cyano group, a substituted or unsubstituted C1 to C20 alkyl group, a substituted or unsubstituted C1 to C20 alkoxy group, a substituted or unsubstituted C6 to C20 aryl group, a substituted or unsubstituted C6 to C20 aryloxy group or a substituted or unsubstituted C3 to C20 heteroaryl group, and at least one pair of $R^{bb}$ and $R^{cc}$ or $R^{dd}$ and $R^{ee}$ may be linked to each other to provide a ring structure, $L^a$ is —O—, —S—, —Se—, —Te—, —$NR^{a1}$—, —$SiR^bR^c$—, —$GeR^dR^e$—, —$(CR^fR^g)_{n1}$—, —$(C(R^p)=N)$—, or single bond, wherein $R^{a1}$, $R^{a2}$, $R^b$, $R^c$, $R^d$, $R^e$, $R^f$, $R^g$, and $R^p$ are each independently hydrogen, deuterium, a halogen, a cyano group, a substituted or unsubstituted C1 to C20 alkyl group, a substituted or unsubstituted C1 to C20 alkoxy group, a substituted or unsubstituted C6 to C20 aryl group or a substituted or unsubstituted C6 to C20 aryloxy group, wherein n1 in —$(CR^fR^g)_{n1}$— is 1 or 2, and hydrogen in each ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group.

In Chemical Formula (6), CH present in the aromatic ring of the moieties (3), (4), (5), (6) and (7) may be replaced by N.

Specific examples of the compound of Chemical Formula 1 may include, but are not limited to, compounds of Groups 1 to 3.

[Group 1]

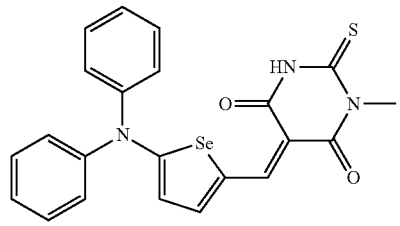
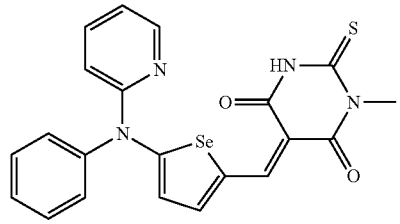
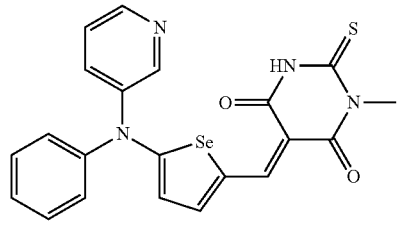
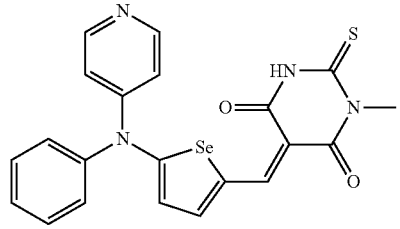

-continued

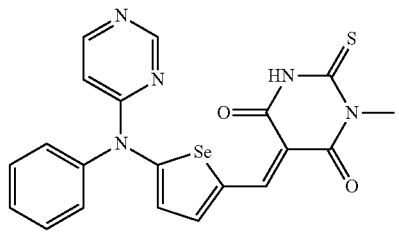
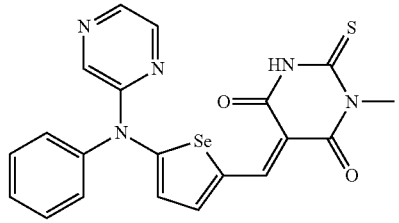
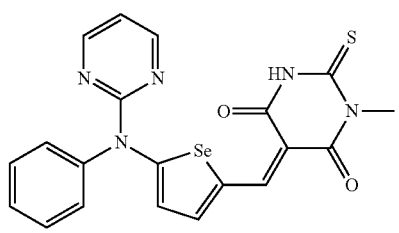
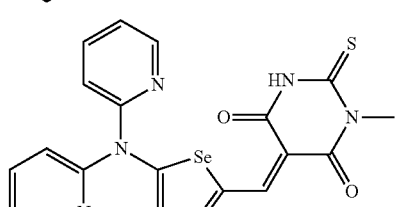
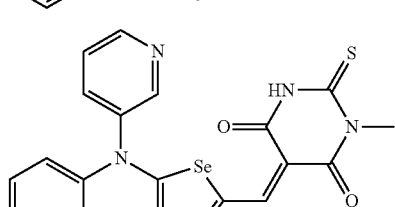
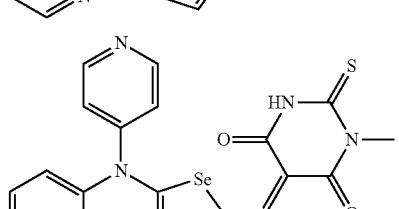
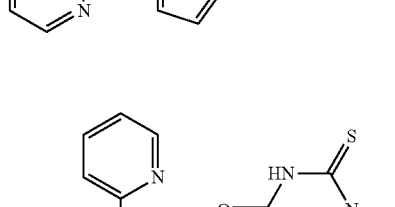

-continued

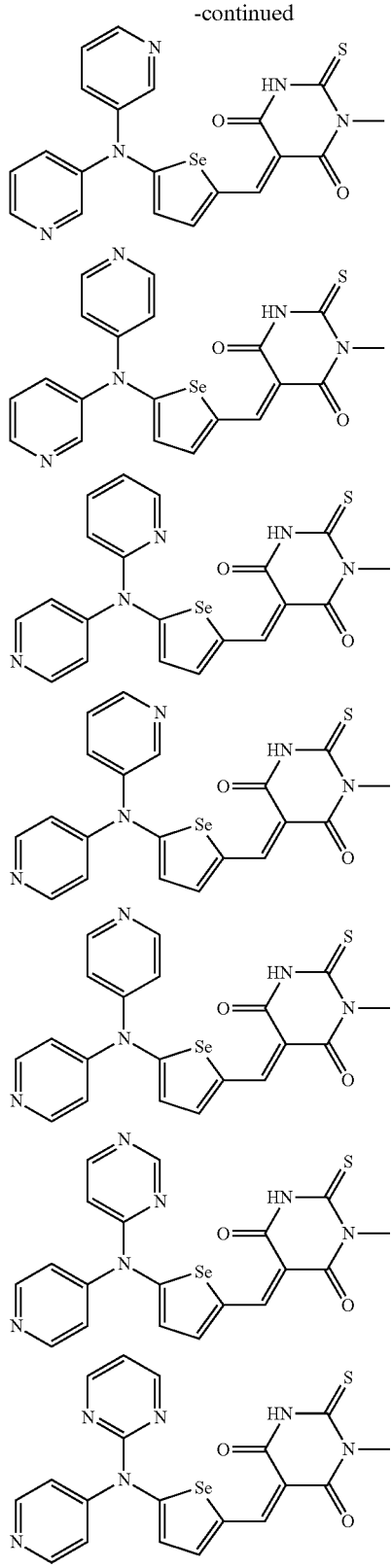

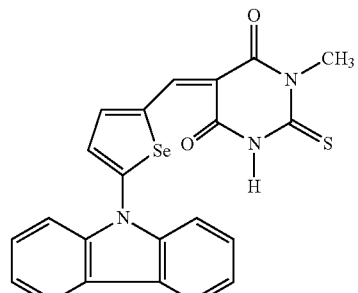
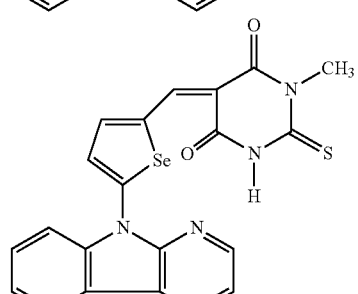
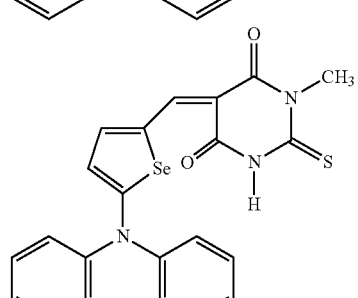
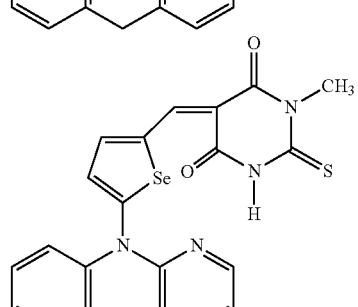
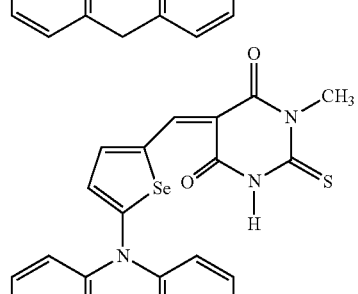
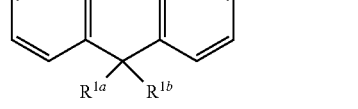

In Group 1,
hydrogen present in each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, I), a cyano group (—CN), a cyano-containing group, and combinations thereof.

[Group 2]

-continued
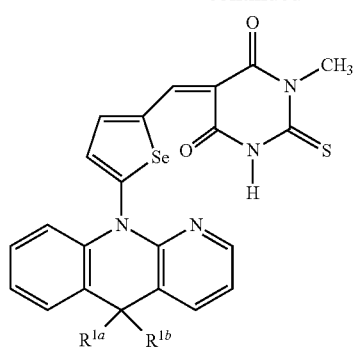
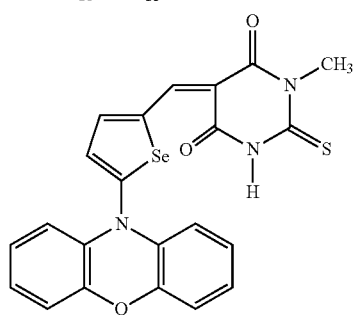
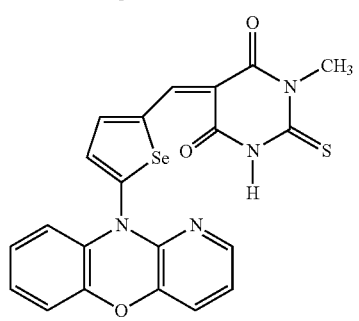
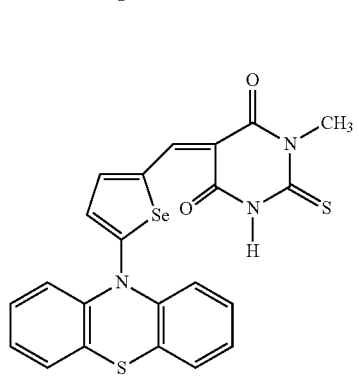
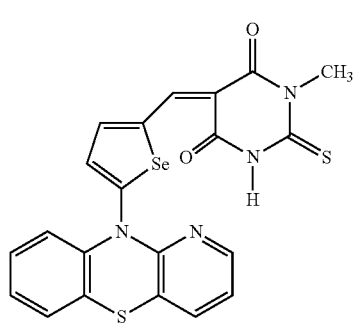
-continued
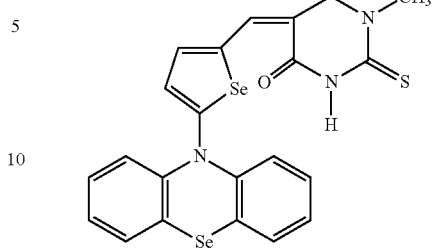
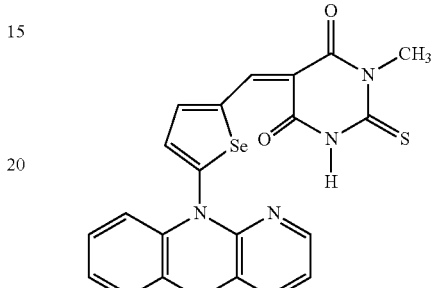
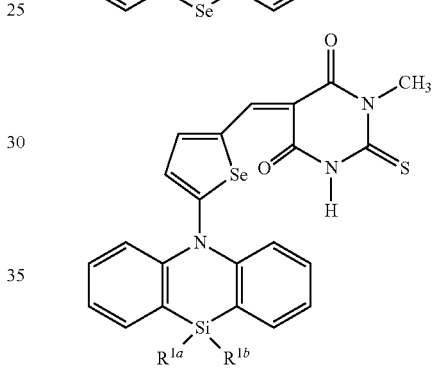
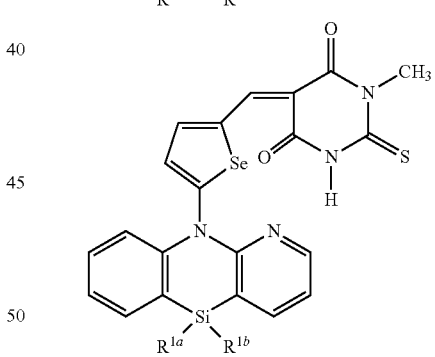

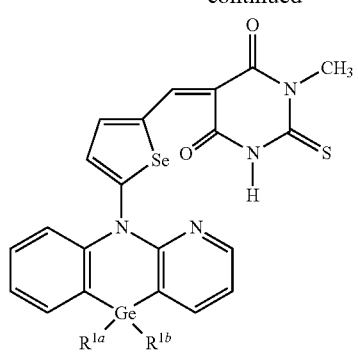
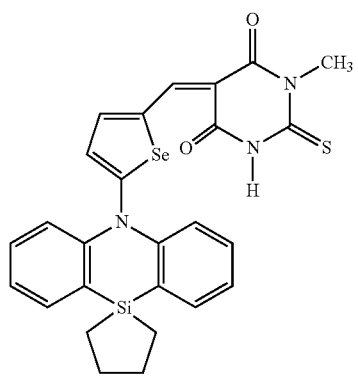
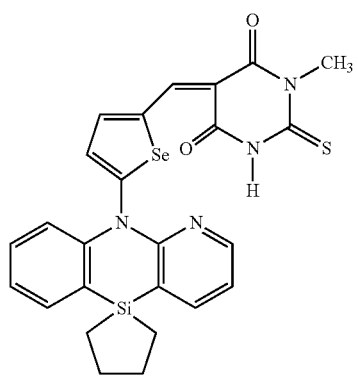
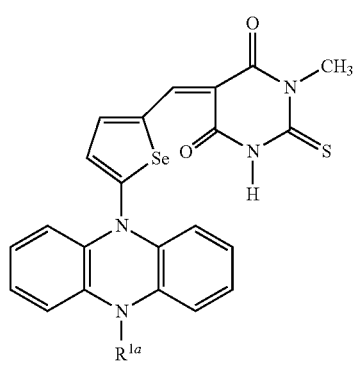

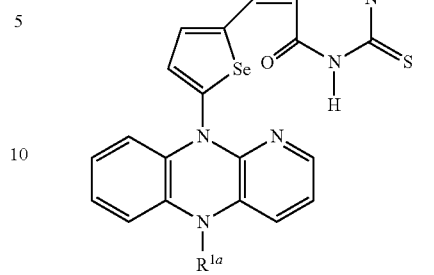
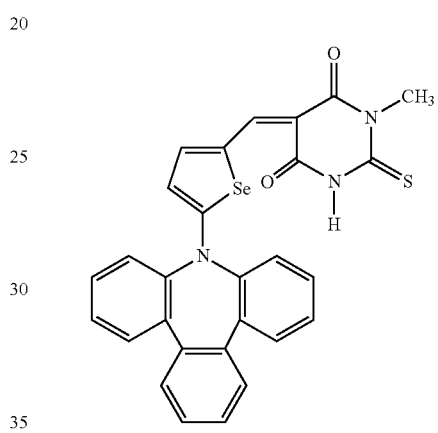
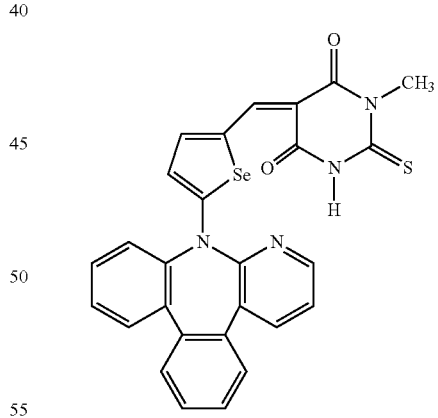

In Group 2,
hydrogen present in each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, I), a cyano group (—CN), a cyano-containing group, and combinations thereof and $R^{1a}$ and $R^{1b}$ may each independently be a C1 to C6 alkyl group, a phenyl group, or a naphthyl group.

[Group 3]
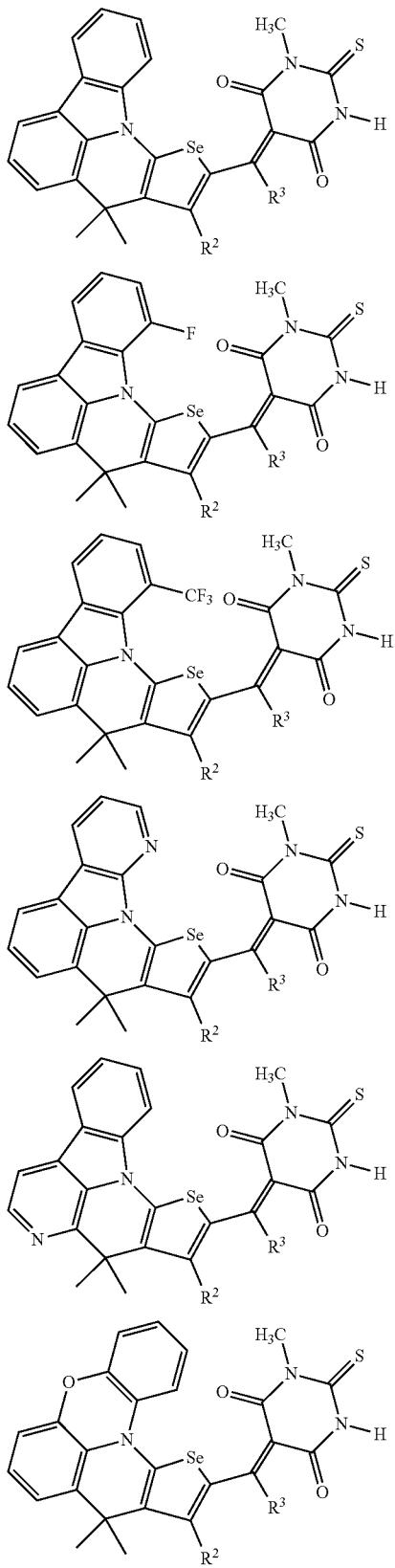
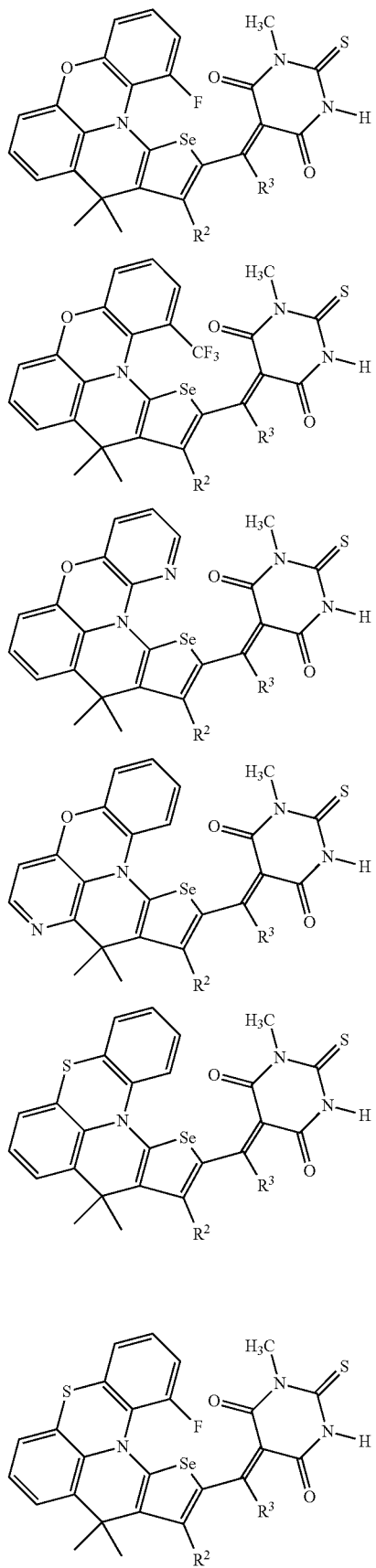

-continued
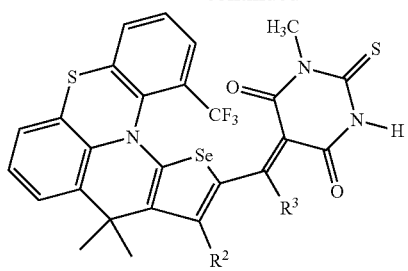
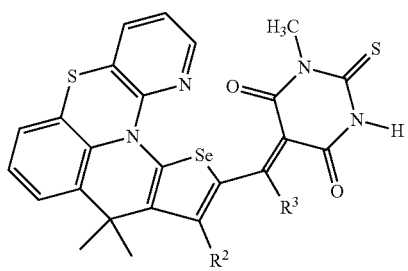
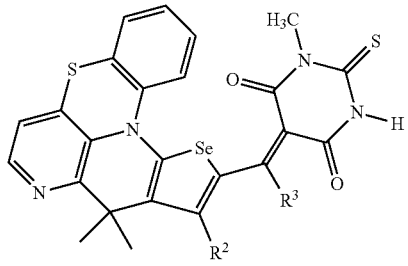
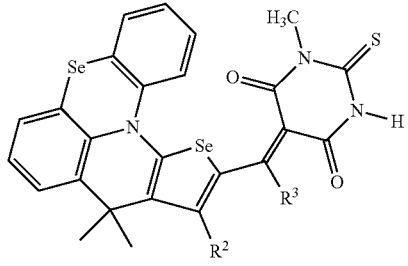
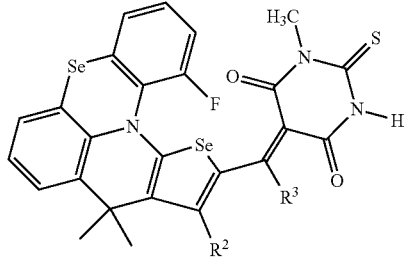
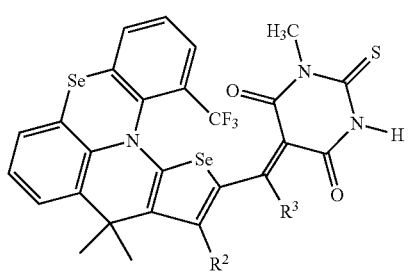
-continued
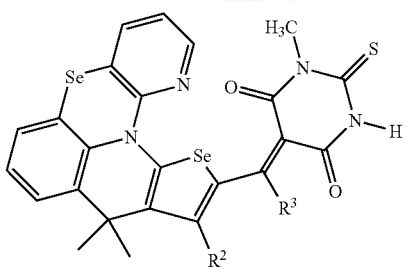
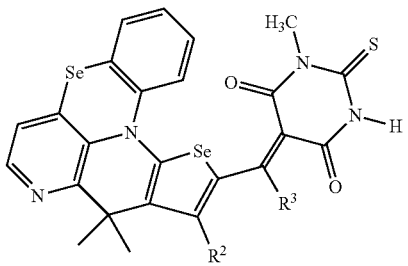
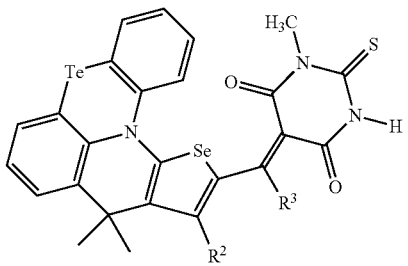
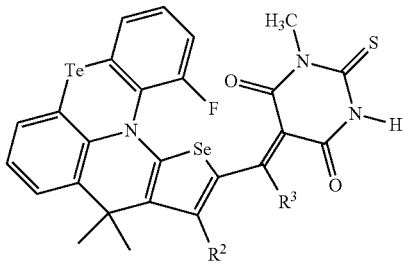
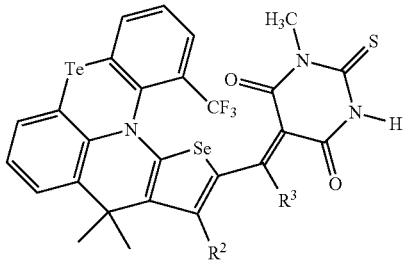
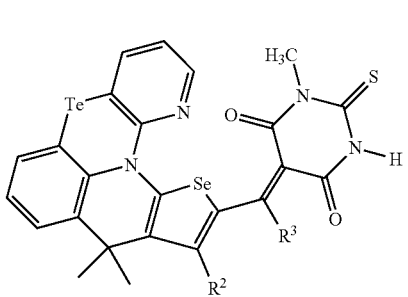

-continued

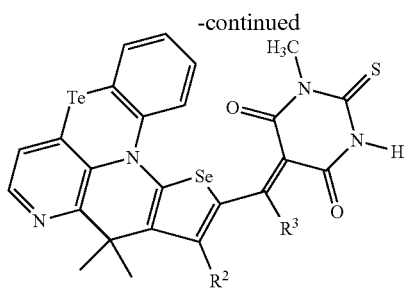

In Group 3,
hydrogen present in each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, I), a cyano group (—CN), a cyano-containing group, and combinations thereof, and
$R^2$ and $R^3$ are each independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof.

In Groups 1 to 3, examples of the compounds in which X of Chemical Formula 1 is Se are provided, but example compounds having other substituents (S, Te, O, S(=O), S(=O)$_2$, NR$^a$, or SiR$^b$R$^c$) are also provided in the same manner.

In Group 3, examples of the compounds in which $G^2$ of Chemical Formula 5 is —(CCH$_3$CH$_3$)— are provided, but examples of compounds having other substituents may also be provided in the same manner.

In Groups 1 to 3, —ND (wherein D is deuterium) may be present instead of —NH of 1-methyl-2-thioxodihydropyrimidine-4,6(1H,5H)-dione.

—NR'$^{11}$ (wherein R'$^{11}$ is an ethyl group, a propyl group or a butyl group) instead of —NCH$_3$ of 1-methyl-2-thioxodihydropyrimidine-4,6(1H,5H)-dione in Groups 1 to 3 may be present.

In Groups 1 to 3, the methyl group of 1-methyl-2-thioxodihydropyrimidine-4,6(1H,5H)-dione is present at the 1st position, but hydrogen may be present at the 1st position and a methyl group may be present at the 3$^{rd}$ position.

The compound is a compound configured to selectively absorb light in a green wavelength region, and may have a maximum absorption wavelength ($\lambda_{max}$) in a wavelength region of about 500 nm to about 600 nm, for example greater than or equal to about 530 nm, greater than or equal to about 535 nm, or greater than or equal to about 540 nm and less than or equal to about 590 nm or less than or equal to about 580 nm.

The compound may exhibit a light absorption curve having a full width at half maximum (FWHM) of about 50 nm to about 120 nm, for example about 50 nm to about 110 nm. Herein, the FWHM is a width of a wavelength corresponding to half of a maximum absorption point. As used herein, when specific definition is not otherwise provided, it may be defined by absorbance measured by UV-Vis spectroscopy. When the full width at half maximum (FWHM) is within the range, selectivity in a green wavelength region may be increased. The thin film may be a thin film deposited under a vacuum condition.

The compound may be formed into a thin film by vapor deposition. The deposition method may provide a uniform thin film and have small inclusion possibility of impurities into the thin film, but when the compound has a lower melting point than a temperature for the deposition, a product decomposed from the compound may be deposited and thus performance of a device may be deteriorated. Accordingly, the compound desirably has a higher melting point than the deposition temperature. In this respect, the compound has a melting point higher than the deposition temperature. Because a difference between the melting point and the deposition temperature may be for example greater than or equal to about 10° C., greater than or equal to about 15° C., the compound may be desirably used in the deposition process.

In more detail, the donor-acceptor type material represented by Chemical Formula 1 may be thermally decomposed at the melting point ($T_m$) of the material because the melting point ($T_m$) is similar to the decomposition temperature ($T_d$). If the temperature (sublimation temperature, deposition temperature, $T_s$) at which a film is formed by vacuum deposition is higher than $T_m$, decomposition occurs more preferentially than sublimation (deposition), and thus a normal device cannot be manufactured. Because it is impossible to produce a stable image sensor with such materials, $T_m$ is required to be higher than $T_s$. In some example embodiments, ($T_m$-$T_s$) may be in the range of ($T_m$-$T_s$)≥10° C. and for example ($T_m$-$T_s$)≥15° C.

In addition, a micro lens array (MLA) needs to be formed to concentrate light after manufacturing an organic photoelectric device during manufacture of an image sensor. Formation of this micro lens array requires a relatively high temperature (greater than or equal to about 160° C., for example greater than or equal to about 170° C., greater than or equal to about 180° C., or greater than or equal to about 190° C.). The performance of the photoelectric devices (e.g., organic photoelectric devices) is required not to be deteriorated in these heat-treatment processes. The performance deterioration of the organic photoelectric device during the heat treatment of MLA may be caused not by chemical decomposition of an organic material but its morphology change. The morphology change is in general caused, when a material starts a thermal vibration due to a heat treatment, but a material having a firm molecule structure may not have the thermal vibration and be prevented from the deterioration by the heat treatment. The compound may be suppressed from the thermal vibration of molecules due to a conjugation structure (particularly, G$^1$-containing linkage structure of Chemical Formula 5) in the donor moiety and thus may be stably maintained during the MLA heat treatment and secure process stability.

The compound may be a p-type semiconductor compound.

Since the compound works as a p-type semiconductor, the compound may be appropriately used, as long as it has a higher LUMO level than an n-type semiconductor. For example, when the compound is mixed with an n-type material such as fullerene, the compound desirably has a higher LUMO level than 4.2 eV than the fullerene having a LUMO level of 4.2 eV. As for the appropriate HOMO-LUMO level of the compound, when the compound has a HOMO level ranging from about 5.2 eV to about 5.8 eV, and an energy bandgap ranging from about 1.4 eV to about 2.6 eV, the LUMO level of the compound is in a range of about 3.8 eV to about 3.2 eV. The compound having a HOMO level, an LUMO level, and an energy bandgap within the ranges may be used as a p-type semiconductor compound effectively absorbing light in a green wavelength region, and thus has high external quantum efficiency (EQE) and resultantly improves photoelectric conversion efficiency.

In some example embodiments, in view of a thin film formation, a stably depositable compound is desirable and thus the compound has a molecular weight of about 300 g/mol to about 1500 g/mol. However, even though the compound has a molecular weight out of the range, a depositable compound may be used without limitation. In addition, when the compound is formed to form a thin film using a coating process, a compound that is dissolved in a solvent and coated may be used without limitation.

Hereinafter, a photoelectric device including the compound according to some example embodiments is described with reference to drawings.

FIG. 1 is a cross-sectional view showing a photoelectric device according to some example embodiments.

Referring to FIG. 1, a photoelectric device 100 according to some example embodiments, including the example embodiments shown in FIG. 1 includes a first electrode 10 and a second electrode 20, and an active layer 30 between the first electrode 10 and the second electrode 20.

One of the first electrode 10 or the second electrode 20 is an anode and the other is a cathode. At least one of the first electrode 10 or the second electrode 20 may be a light-transmitting electrode, and the light-transmitting electrode may be made of, for example, a transparent conductor such as indium tin oxide (ITO) or indium zinc oxide (IZO), or a metal thin layer of a thin single layer or multilayer. When one of the first electrode 10 or the second electrode 20 is a non-light-transmitting electrode, it may be made of, for example, an opaque conductor such as aluminum (Al).

The active layer 30 includes a p-type semiconductor and an n-type semiconductor to form a pn junction and absorbs external light to generate excitons and then separates the generated excitons into holes and electrons.

The active layer 30 includes the compound represented by Chemical Formula 1. The compound may act as a p-type semiconductor compound in the active layer 30.

The compound is a compound configured to selectively absorb light in a green wavelength region, and the active layer 30 including the compound may have a maximum absorption wavelength ($\lambda_{max}$) in a wavelength region of greater than or equal to about 500 nm and less than or equal to about 600 nm, for example greater than or equal to about 530 nm, greater than or equal to about 535 nm, or greater than or equal to about 540 nm and less than or equal to about 590 nm or less than or equal to about 580 nm.

The active layer 30 may exhibit a light absorption curve having a relatively narrow full width at half maximum (FWHM) of about 50 nm to about 130 nm, for example about 50 nm to about 120 nm. Accordingly, the active layer 30 has high selectivity for light in a green wavelength region.

The active layer 30 may have an absorption coefficient of greater than or equal to about $8.5 \times 10^4$ cm$^{-1}$, for example about $8.7 \times 10^4$ cm$^{-1}$ to about $10 \times 10^4$ cm$^{-1}$ when the active layer 30 includes in a volume ratio of about 0.9:1 to about 1.1:1, for example about 1:1.

The active layer 30 may further include an n-type semiconductor compound for forming pn junction.

The n-type semiconductor compound may be sub-phthalocyanine or a sub-phthalocyanine derivative, fullerene or a fullerene derivative, thiophene or a thiophene derivative, or a combination thereof.

The fullerene may include C60, C70, C76, C78, C80, C82, C84, C90, C96, C240, C540, a mixture thereof, a fullerene nanotube, and the like. The fullerene derivative may refer to compounds of these fullerenes having a substituent thereof. The fullerene derivative may include a substituent such as an alkyl group (e.g., C1 to C30 alkyl group), an aryl group (e.g., C6 to C30 aryl group), a heterocyclic group (e.g., C3 to C30 cycloalkyl group), and the like. Examples of the aryl groups and heterocyclic groups may be a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, a quinazoline ring, an isoquinoline ring, a carbazole ring, a phenanthridine ring, an acridine ring, a phenanthroline ring, a thianthrene ring, a chromene ring, an xanthene ring, a phenoxazine ring, a phenoxathin ring, a phenothiazine ring, or a phenazine ring.

The sub-phthalocyanine or the sub-phthalocyanine derivative may be represented by Chemical Formula 7.

[Chemical Formula 7]

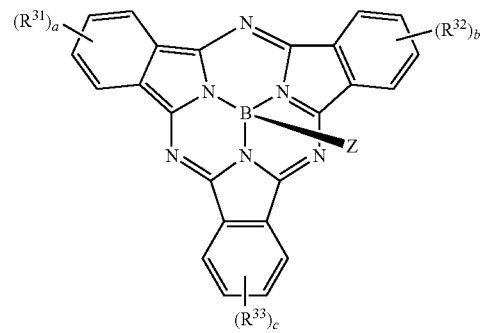

In Chemical Formula 7,

R$^{31}$ to R$^{33}$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a halogen-containing group, or a combination thereof, a, b, and c are integers of 1 to 3, and Z is a monovalent substituent.

For example, Z may be a halogen or a halogen-containing group, for example F, Cl, an F-containing group, or a Cl-containing group.

The halogen refers to F, Cl, Br, or I and the halogen-containing group refers to an alkyl group (C1 to C30 alkyl group) where at least one hydrogen of the alkyl group is replaced by F, Cl, Br, or I.

The thiophene derivative may be for example represented by Chemical Formula 8 or Chemical Formula 9, but is not limited thereto.

[Chemical Formula 8]

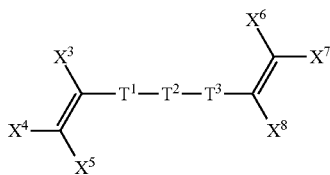

[Chemical Formula 9]

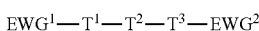

In Chemical Formulas 8 and 9, $T^1$, $T^2$, and $T^3$ are aromatic rings including substituted or unsubstituted thiophene moieties, $T^1$, $T^2$, and $T^3$ are independently present or are fused to each other, $X^3$ to $X^8$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a cyano group, or a combination thereof, and $EWG^1$ and $EWG^2$ are independently electron withdrawing groups.

For example, in Chemical Formula 8, at least one of $X^3$ to $X^8$ may be an electron withdrawing group, for example a cyano-containing group.

The active layer 30 may further include a second p-type semiconductor compound configured to selectively absorb green light. The second p-type semiconductor compound may be a compound represented by Chemical Formula 10.

[Chemical Formula 10]

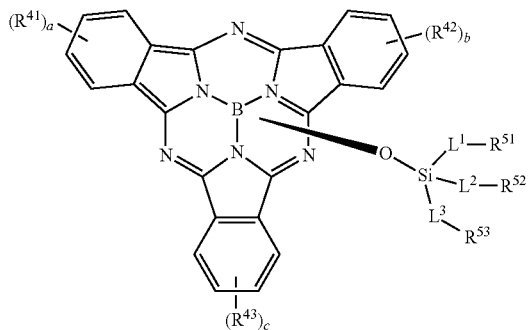

In Chemical Formula 10, $R^{41}$ to $R^{43}$ are each independently hydrogen, a substituted or unsubstituted C1 to C30 aliphatic hydrocarbon group, a substituted or unsubstituted C6 to C30 aromatic hydrocarbon group, a substituted or unsubstituted C1 to C30 aliphatic heterocyclic group, a substituted or unsubstituted C2 to C30 aromatic heterocyclic group, a substituted or unsubstituted C1 to C30 alkoxy group, a substituted or unsubstituted C6 to C30 aryloxy group, a thiol group, a substituted or unsubstituted C1 to C30 alkylthio group, a substituted or unsubstituted C6 to C30 arylthio group, a cyano group, a cyano-containing group, a halogen, a halogen-containing group, a substituted or unsubstituted sulfonyl group (e.g., a substituted or unsubstituted C0 to C30 aminosulfonyl group, a substituted or unsubstituted C1 to C30 alkylsulfonyl group or a substituted or unsubstituted C6 to C30 arylsulfonyl group), or a combination thereof, or two adjacent groups of $R^{41}$ to $R^{43}$ are linked to each other to provide a fused ring, $L^1$ to $L^3$ are each independently a single bond, a substituted or unsubstituted C1 to C30 alkylene group, a substituted or unsubstituted C6 to C30 arylene group, divalent a substituted or unsubstituted C3 to C30 heterocyclic group, or a combination thereof, $R^{51}$ to $R^{53}$ are each independently a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group (e.g., a substituted or unsubstituted C1 to C30 alkylamine group or a substituted or unsubstituted C6 to C30 arylamine group), a substituted or unsubstituted silyl group, or a combination thereof, and a to c are each independently an integer ranging from 0 to 4.

The second p-type semiconductor compound configured to selectively absorb green light may be included in an amount of about 500 to about 1500 parts by weight based on 100 parts by weight of the compound represented by Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the compound of Chemical Formula 1 and the n-type semiconductor compound in a ratio of about 1:100 to about 100:1. The compound of Chemical Formula 1 and the n-type semiconductor compound may be included in a ratio ranging from about 1:50 to about 50:1 within the range, specifically, about 1:10 to about 10:1, and more specifically, about 1:1. When the compound of Chemical Formula 1 and the n-type semiconductor compound have a composition ratio within the range, an exciton may be effectively produced, and a pn junction may be effectively formed.

The p-type layer may include the semiconductor compound of Chemical Formula 1, and the n-type layer may include the n-type semiconductor compound.

The active layer 30 may have a thickness of about 1 nm to about 500 nm and specifically, about 5 nm to about 300 nm. When the active layer 30 has a thickness within the range, the active layer may effectively absorb light, effectively separate holes from electrons, and deliver them, thereby effectively improving photoelectric conversion efficiency. A desirable thickness of the active layer 30 may be, for example, determined by an absorption coefficient of the active layer 30, and may be, for example, a thickness being capable of absorbing light of at least about 70% or more, for example about 80% or more, and for another example about 90% or more.

In the photoelectric device 100, when light enters from the first electrode 10 and/or second electrode 20, and when the active layer 30 absorbs light in a predetermined wavelength region, excitons may be produced from the inside. The excitons are separated into holes and electrons in the active layer 30, and the separated holes are transported to an anode that is one of the first electrode 10 or the second electrode 20 and the separated electrons are transported to the cathode that is the other of the first electrode 10 and the second electrode 20 so as to flow a current in the photoelectric device.

Hereinafter, a photoelectric device according to some example embodiments is described with reference to FIG. 2.

Figure 2:
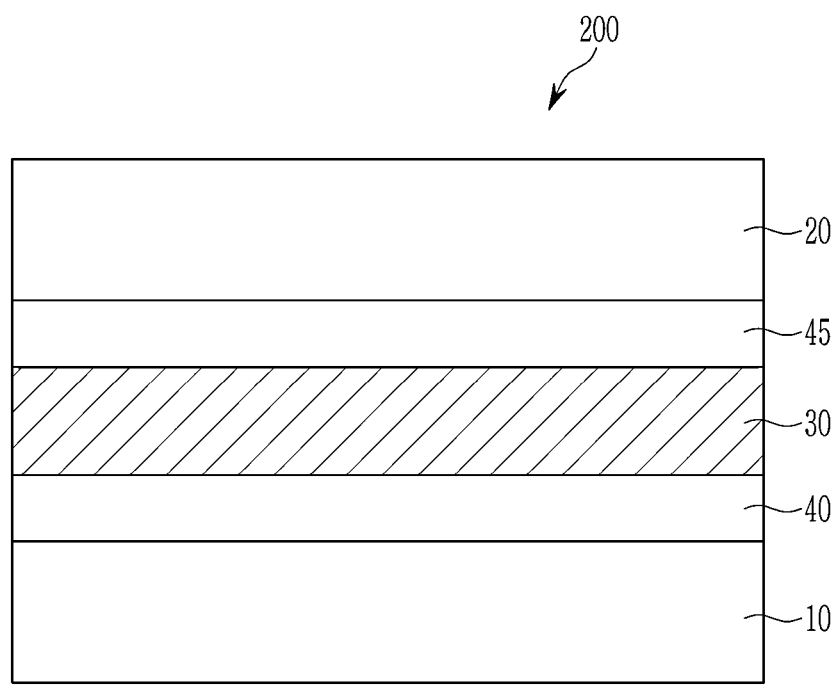
FIG. 2 is a cross-sectional view showing a photoelectric device according to some example embodiments.

FIG. 2 is a cross-sectional view showing a photoelectric device according to some example embodiments.

Referring to FIG. 2, a photoelectric device 200 according to some example embodiments, including the example embodiments shown in FIG. 2 includes a first electrode 10 and a second electrode 20 facing each other, and an active layer 30 between the first electrode 10 and the second electrode 20, like some example embodiments, including the example embodiments shown in FIG. 1.

However, the photoelectric device 200 according to some example embodiments, including the example embodiments shown in FIG. 2 further includes charge auxiliary layers 40 and 45 between the first electrode 10 and the active layer 30, and the second electrode 20 and the active layer 30, unlike some example embodiments, including the example embodiments shown in FIG. 1. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for preventing electron transport, an electron injection layer (EIL) for facilitating electron injection, an electron transport layer (ETL) for facilitating electron transport, and a hole blocking layer (HBL) for preventing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include one selected from, for example, poly(3,4-ethylenedioxythiophene):poly(styrenesulfonate) (PE DOT: PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl ($\alpha$-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PE DOT: PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl ($\alpha$-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 or 45 may be omitted.

The photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
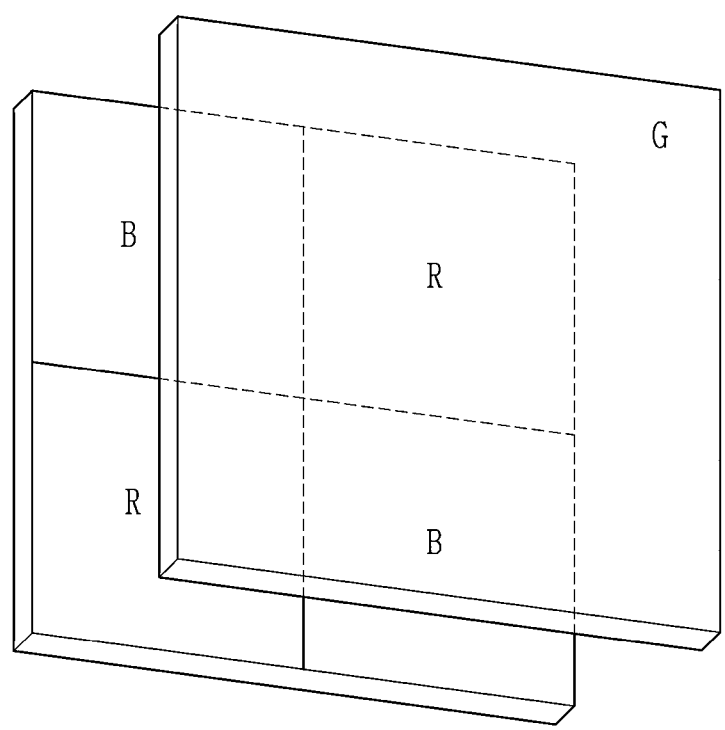
FIG. 3 is a schematic top plan view showing an organic CMOS image sensor according to some example embodiments.
Figure 4:
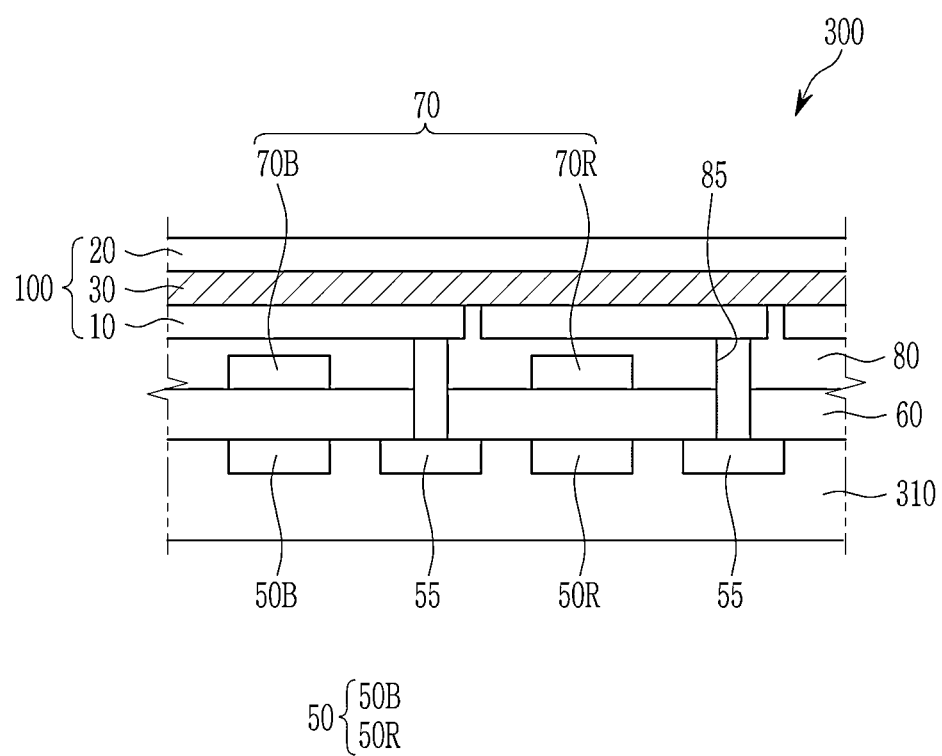
FIG. 4 is a cross-sectional view showing the organic CMOS image sensor of FIG. 3.

FIG. 3 is a schematic top plan view showing an organic CMOS image sensor according to some example embodiments, and FIG. 4 is a cross-sectional view showing the organic CMOS image sensor of FIG. 3.

Referring to FIGS. 3 and 4, an organic CMOS image sensor 300 according to some example embodiments, including the example embodiments shown in FIGS. 3 and 4 includes a semiconductor substrate 310 integrated with photo-sensing device 50, which may include photo-sensing devices 50B and 50R, a transmission transistor (not shown), a charge storage 55, a lower insulation layer 60, a color filter layer 70, an upper insulation layer 80, and a photoelectric device 100.

The semiconductor substrate 310 may be a silicon substrate, and is integrated with the photo-sensing device 50, the transmission transistor (not shown), and the charge storage 55. The photo-sensing devices 50R and 50B may be photodiodes.

The photo-sensing devices 50B and 50R, the transmission transistor, and/or the charge storage 55 may be integrated in each pixel, and as shown in the drawing, the photo-sensing devices 50B and 50R may be respectively included in a blue pixel and a red pixel and the charge storage 55 may be included in a green pixel.

The photo-sensing devices 50B and 50R sense light, the information sensed by the photo-sensing devices may be transferred by the transmission transistor, the charge storage 55 is electrically connected to the photoelectric device 100, and the information of the charge storage 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 310. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70B formed in the blue pixel and selectively transmitting blue light and a red filter 70R formed in the red pixel and selectively transmitting red light. In some example embodiments, a cyan filter and a yellow filter may be disposed instead of the blue filter 70B and red filter 70R. In some example embodiments, including the example embodiments shown in FIGS. 3 and 4, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The aforementioned photoelectric device 100 is formed on the upper insulation layer 80. The photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs and/or senses light in a green wavelength region and replaces a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

As described above, the photoelectric devices configured to selectively absorb light in a green wavelength region are stacked and thereby a size of an image sensor may be decreased and a down-sized image sensor may be realized.

As described above, the compound represented by the Chemical Formula 1 may be used as a semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

In some example embodiments, in FIG. 4, additional color filters may be further disposed on the photoelectric device 100. The additional color filters may include a blue filter 70B and a red filter 70R or a cyan filter and a yellow filter.

Figure 5:
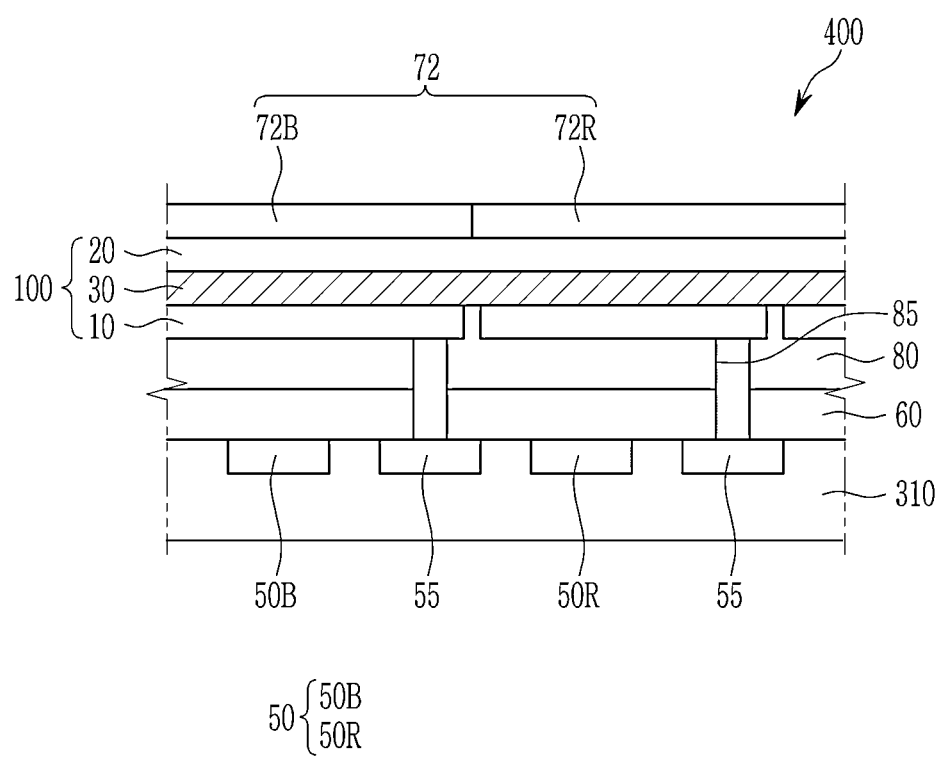
FIG. 5 is a schematic cross-sectional view showing an organic CMOS image sensor according to some example embodiments.

The organic CMOS image sensor with the color filters disposed on the photoelectric device is shown in FIG. 5. FIG. 5 is a schematic cross-sectional view showing an organic CMOS image sensor according to some example embodiments. Referring to FIG. 5, an organic CMOS image sensor 400 has the same structure as FIG. 4 except that a color filter layer 72 including the blue filter 72B and the red filter 72R is disposed on the photoelectric device 100. Instead of the blue filter 72B and the red filter 72R, a cyan filter and a yellow filter may be disposed respectively.

In FIGS. 4 and 5, the photoelectric device 100 of FIG. 1 is included, but it is not limited thereto, and thus the photoelectric device 200 of FIG. 2 may be applied in the same manner.

Figure 6:
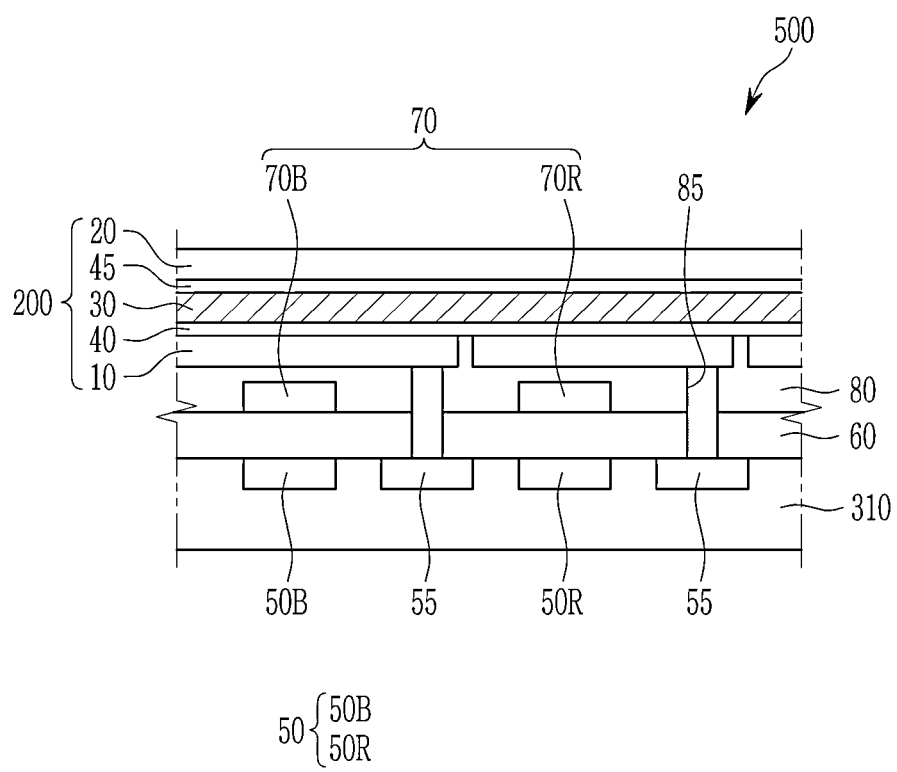
FIG. 6 is a schematic cross-sectional view showing an organic CMOS image sensor according to some example embodiments.

FIG. 6 is a cross-sectional view showing an organic CMOS image sensor 500 to which the photoelectric device 200 is applied.

Referring to FIG. 6, the organic CMOS image sensor 500 includes a semiconductor substrate 310 integrated with photo-sensing devices 50B and 50R, a transmission transistor (not shown), a charge storage 55, an insulation layer 80, and a photoelectric device 200, like some example embodiments, including the example embodiments shown in FIG. 4.

However, the organic CMOS image sensor 500 according to some example embodiments, including the example embodiments shown in FIG. 6, includes the photoelectric device 200, unlike some example embodiments, including the example embodiments shown in FIG. 4, which include the photoelectric device 100.

Figure 7:
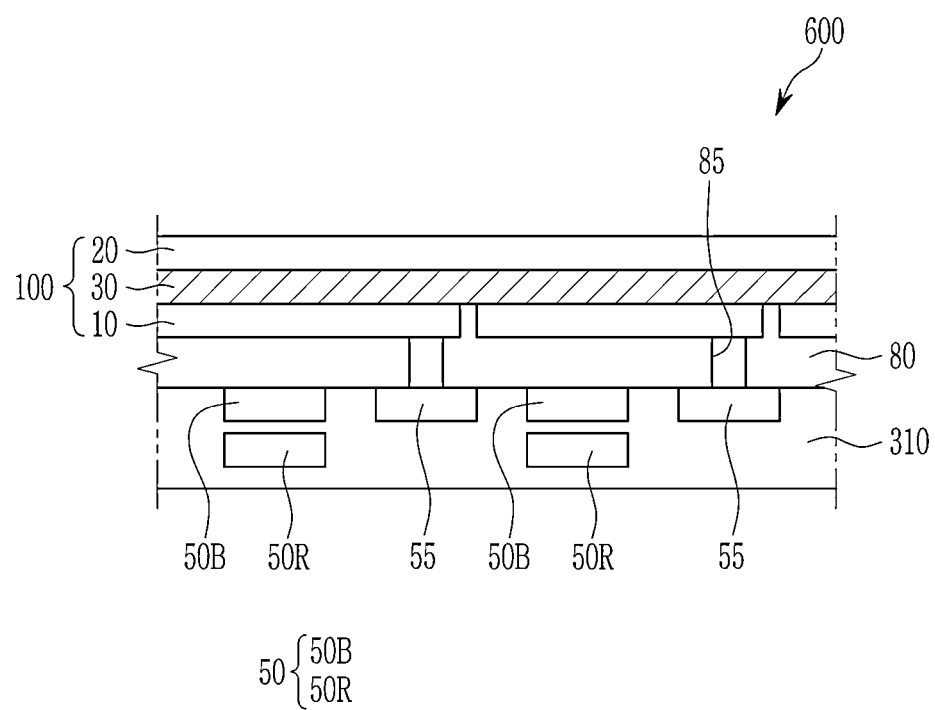
FIG. 7 is a schematic view showing an organic CMOS image sensor according to some example embodiments.

FIG. 7 is a schematic view showing an organic CMOS image sensor according to some example embodiments.

Referring to FIG. 7, the organic CMOS image sensor 600 includes a semiconductor substrate 310 integrated with photo-sensing devices 50B and 50R, a transmission transistor (not shown), a charge storage 55, an insulation layer 80, and a photoelectric device 100, like some example embodiments, including the example embodiments shown in FIG. 5.

However, the organic CMOS image sensor 600 according to some example embodiments, including the example embodiments shown in FIG. 7 includes the blue photo-sensing device 50B and the red photo-sensing device 50R that are stacked and does not include a color filter layer 70, unlike some example embodiments, including the example embodiments shown in FIG. 5. The blue photo-sensing device 50B and the red photo-sensing device 50R are electrically connected with the charge storage 55, and the information of the charge storage 55 may be transferred by the transmission transistor (not shown). The blue photo-sensing device 50B and the red photo-sensing device 50R may selectively absorb light in each wavelength region depending on a stack depth.

As described above, the photoelectric devices configured to selectively absorb light in a green wavelength region are stacked and the red photo-sensing device and the blue photo-sensing device are stacked, and thereby a size of an image sensor may be decreased and a down-sized image sensor may be realized. As described above, the photoelectric device 100 has improved green wavelength selectivity, and crosstalk caused by unnecessary absorption of light in a wavelength region except green may be decreased while increasing sensitivity.

In FIG. 7, the photoelectric device 100 of FIG. 1 is included, but it is not limited thereto, and thus the photoelectric device 200 of FIG. 2 may be applied in the same manner.

Figure 8:
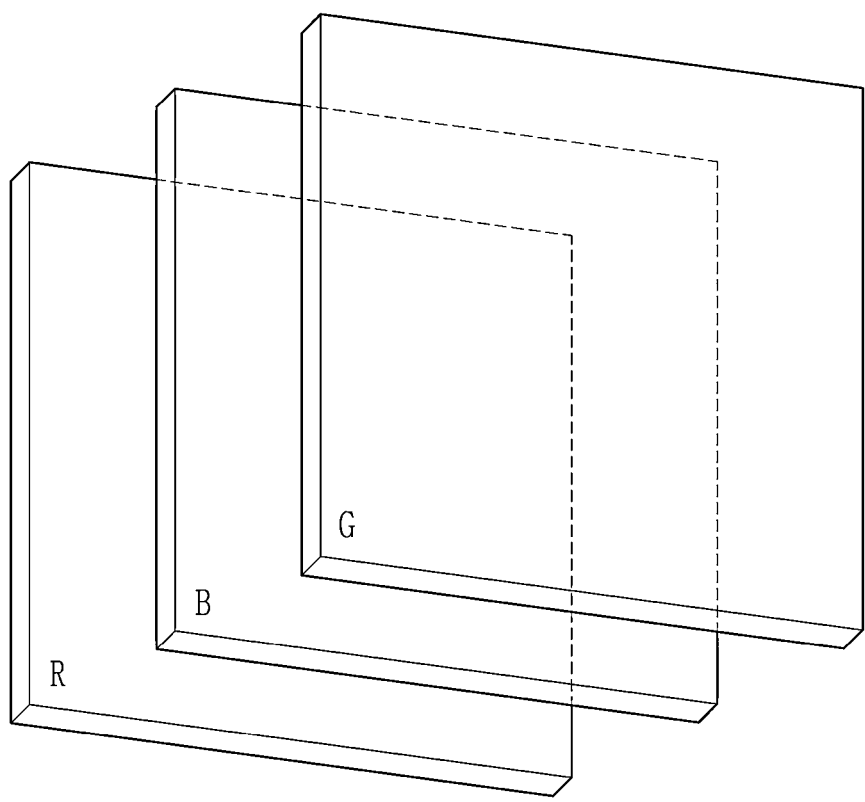
FIG. 8 is a schematic view showing an organic CMOS image sensor according to some example embodiments.

FIG. 8 is a schematic view showing an organic CMOS image sensor according to some example embodiments.

Referring to FIG. 8, the organic CMOS image sensor according to some example embodiments, including the example embodiments shown in FIG. 8 includes a green photoelectric device (G) configured to selectively absorb light in a green wavelength region, a blue photoelectric device (B) configured to selectively absorb light in a blue wavelength region, and a red photoelectric device configured to selectively absorb light in a red wavelength region that are stacked.

In the drawing, the green photoelectric device, the blue photoelectric device, and the red photoelectric device are sequentially stacked, but the stack order may be changed without limitation.

The green photoelectric device may be the aforementioned photoelectric device 100 or photoelectric device 200, the blue photoelectric device may include electrodes facing each other and an active layer interposed therebetween and including an organic material configured to selectively absorb light in a blue wavelength region, and the red photoelectric device may include electrodes facing each other and an active layer interposed therebetween and including an organic material configured to selectively absorb light in a red wavelength region.

As described above, the green photoelectric device (G) configured to selectively absorb light in a green wavelength region, the blue photoelectric device (B) configured to selectively absorb light in a blue wavelength region, and the red photoelectric device (R) configured to selectively absorb light in a red wavelength region are stacked, and thereby a size of an image sensor may be decreased and a down-sized image sensor may be realized.

The image sensor absorbs light in an appropriate wavelength region and may show all improved sensitivity (YSNR10) and color reproducibility (ΔE*ab) despite a stacked structure.

Herein, the YSNR10 indicates sensitivity of the image sensor, which is measured in a method described in Juha Alakarhu's "Image Sensors and Image Quality in Mobile Phones" printed in 2007 International Image Sensor Workshop (Ogunquit Maine, USA) but minimum illuminance expressed by lux at a ratio of 10 between signal and noise. Accordingly, the smaller the YSNR10 is, the higher sensitivity is.

On the other hand, the color reproducibility (ΔE*ab) shows a difference from standard colors in an X-Rite chart, and the ΔE*ab is defined as a distance between two points on a L*a*b* color space by CIE (Commission International de L'Eclairage) in 1976. For example, the color difference may be calculated according to Equation 1.

$$\Delta E = \sqrt{(\Delta L^*)^2 + (\Delta a^*)^2 + (\Delta b^*)^2} \quad \text{[Equation 1]}$$

In Equation 1,

ΔL* denotes a change of a color coordinate L* compared with the color coordinate L* at room temperature (about 20° C. to about 25° C.), Δa* denotes a change of a color coordinate a* compared with the color coordinate a* at room temperature, and Δb* denotes a change of a color coordinate b* compared with the color coordinate b* at room temperature.

In order to manufacture an image sensor having high sensitivity and high color reproducibility, YSNR10≤100 lux at ΔE*ab≤3, and herein, the compound may realize YSNR10≤100 lux of sensitivity and color reproducibility at ΔE*ab≤3.

The image sensor may be applied to various electronic devices, for example, a mobile phone, a digital camera, and the like but is not limited thereto.

Figure 9:
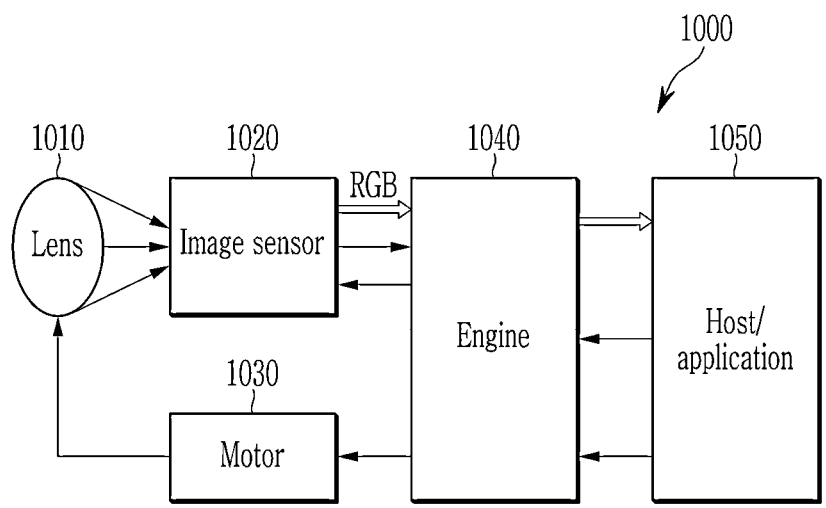
FIG. 9 is a block diagram of a digital camera including an image sensor according to some example embodiments.

FIG. 9 is a block diagram of a digital camera including an image sensor according to some example embodiments.

Referring to FIG. 9, a digital camera 1000 includes a lens 1010, an image sensor 1020, a motor 1030, and an engine 1040. The image sensor 1020 may be one of image sensors according to some example embodiments, including the example embodiments shown in FIGS. 3 to 8.

The lens 1010 concentrates incident light on the image sensor 1020. The image sensor 1020 generates RGB data for received light through the lens 1010.

In some example embodiments, the image sensor 1020 may interface with the engine 1040.

The motor 1030 may adjust the focus of the lens 1010 or perform shuttering in response to a control signal received from the engine 1040. The engine 1040 may control the image sensor 1020 and the motor 1030.

The engine 1040 may be connected to a host/application 1050.

Figure 10:
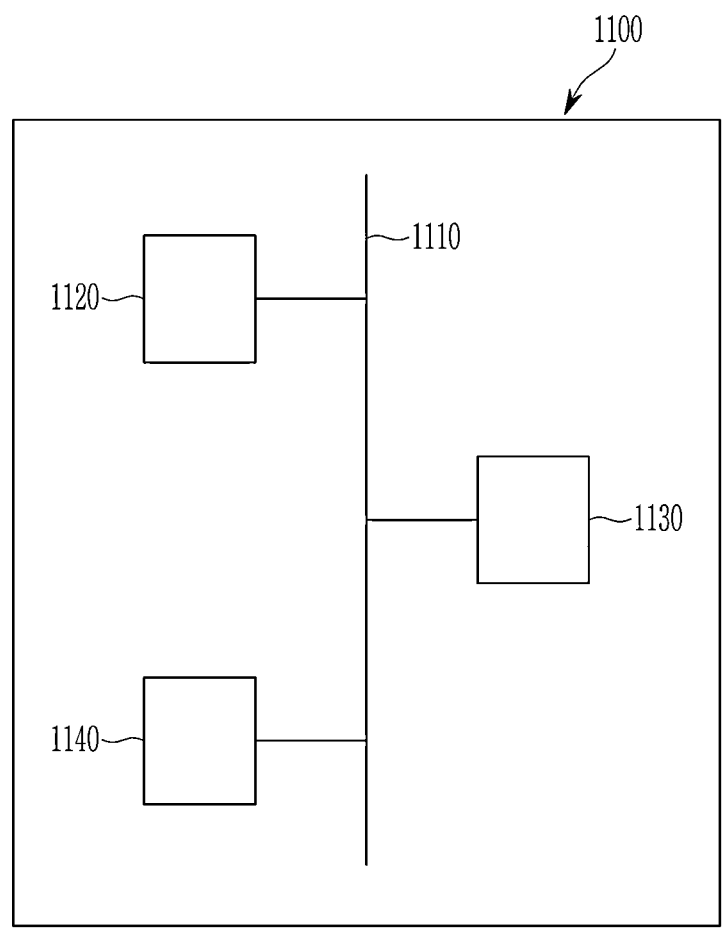
FIG. 10 is a schematic diagram showing an electronic device according to some example embodiments.

FIG. 10 is a schematic diagram showing an electronic device according to some example embodiments.

Referring to FIG. 10, an electronic device 1100 may include a processor 1120, a memory 1130, and an image sensor 1140 that are electrically coupled together via a bus 1110.

The image sensor 1140 may be an image sensor and/or an organic sensor according to any of the example embodiments. The memory 1130, which may be a non-transitory computer readable medium and may store a program of instructions. The memory 1130 may be a nonvolatile memory, such as a flash memory, a phase-change random access memory (PRAM), a magneto-resistive RAM (MRAM), a resistive RAM (ReRAM), or a ferro-electric RAM (FRAM), or a volatile memory, such as a static RAM (SRAM), a dynamic RAM (DRAM), or a synchronous DRAM (SDRAM). The processor 1120 may execute the stored program of instructions to perform one or more functions. For example, the processor 1120 may be configured to process electrical signals generated by the image sensor 1140. The processor 1120 may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc. The processor 1120 may be configured to generate an output (e.g., an image to be displayed on a display interface) based on such processing.

One or more of the processor 1120, memory 1130, motor 1030, engine 1040, or host/application 1050 may be included in, include, and/or implement one or more instances of processing circuitry such as hardware including logic circuits, a hardware/software combination such as a processor executing software; or a combination thereof. In some example embodiments, said one or more instances of processing circuitry may include, but are not limited to, a central processing unit (CPU), an application processor (AP), an arithmetic logic unit (ALU), a graphic processing unit (GPU), a digital signal processor, a microcomputer, a field programmable gate array (FPGA), a System-on-Chip (SoC) a programmable logic unit, a microprocessor, or an application-specific integrated circuit (ASIC), etc. In some example embodiments, any of the memories, memory units, or the like as described herein may include a non-transitory computer readable storage device, for example a solid state drive (SSD), storing a program of instructions, and the one or more instances of processing circuitry may be configured to execute the program of instructions to implement the functionality of some or all of any of the processor 1120, memory 1130, motor 1030, engine 1040, or host/application 1050, or the like according to any of the example embodiments as described herein.

Hereinafter, some example embodiments are illustrated in more detail with reference to examples. However, these examples are non-limiting, and inventive concepts are not limited thereto.

Synthesis Example 1: Synthesis of Compound Represented by Chemical Formula 1-1

[Chemical Formula 1-1]

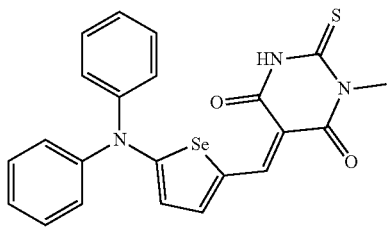

[Reaction Scheme 1-1]

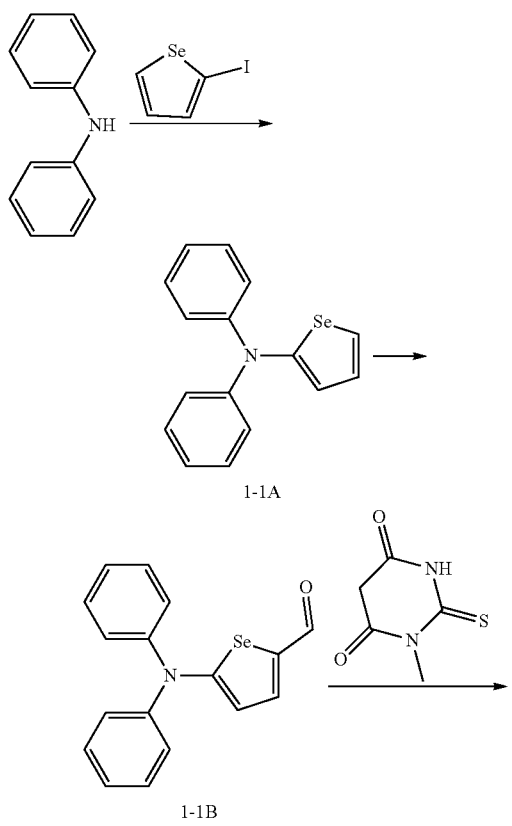

(i) Synthesis of Compound 1-1A 9.48 g (36.9 mmol) of 2-iodoselenophene and 5.68 g (33.5 mmol) of diphenylamine are heated under reflux in 150 ml of anhydrous toluene under the presence of 5 mol % of bis(dibenzylideneacetone)palladium (0), Pd(dba)$_2$), 5 mol % of tri-tert-butylphosphine (P(tBu)$_3$), and 9.67 g (100.6 mmol) of sodium tert-butoxide (NaOtBu) for 2 hours. A product obtained therefrom is separated and purified through silica gel column chromatography (in a volume ratio of toluene:hexane=1:4), obtaining 8.0 g (Yield: 80%) of Compound 1-1A (N,N-diphenylselenophen-2-amine).

(ii) Synthesis of Compound 1-1B 1.46 ml of phosphoryl chloride is added dropwise to 3.56 ml of N,N-dimethylformamide at −15° C. and then, stirred at room temperature (24° C.) for 2 hours. The obtained resultant is slowly added dropwise to a mixture of 200 ml of dichloromethane and 3.11 g of Compound 1-1A at −15° C. and then, stirred at room temperature (24° C.) for 30 minutes and concentrated under a reduced pressure. Subsequently, 100 ml of water is added thereto, and an aqueous sodium hydroxide solution is added thereto until pH becomes 14 and then, stirred at room temperature (24° C.) for 2 hours. Then, an organic layer extracted therefrom with dichloromethane is washed with an aqueous sodium chloride solution and dried with anhydrous magnesium sulfate. The obtained product is separated and purified through silica gel column chromatography (in a volume ratio of hexane:ethylacetate=4:1), obtaining 2.50 g (Yield: 83%) of Compound 1-1B (5-(diphenylamino)selenophene-2-carbaldehyde).

(iii) Synthesis of Compound Represented by Chemical Formula 1-1

2.50 g (7.50 mmol) of Compound 1-1B is suspended in ethanol, 1.42 g (9.00 mmol) of 1-methyl-2-thioxodihydropyrimidine-4,6(1H,5H)-dione is added thereto and then, reacted at 50° C. for 2 hours, obtaining 2.7 g (Yield: 77%) of a compound represented by Chemical Formula 1-1. The obtained compound is purified through sublimation up to purity of 99.9%.

$^1$H-NMR (500 MHz, Methylene Chloride-d$_2$): δ 8.97 (s, 1H), 8.77 (s, 1H), 8.28 (s, 2H), 7.84 (d, 2H) 7.44-7.40 (m, 8H), 7.38-7.33 (m, 12H), 6.50 (d, 2H), 3.57 (s, 3H), 3.51 (s, 3H).

Synthesis Example 2: Synthesis of Compound Represented by Chemical Formula 1-2

[Chemical Formula 1-2]

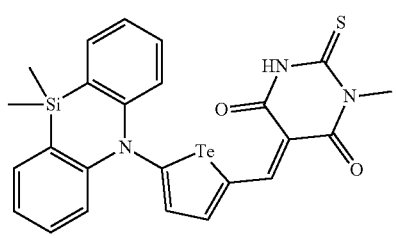

[Reaction Scheme 1-2]

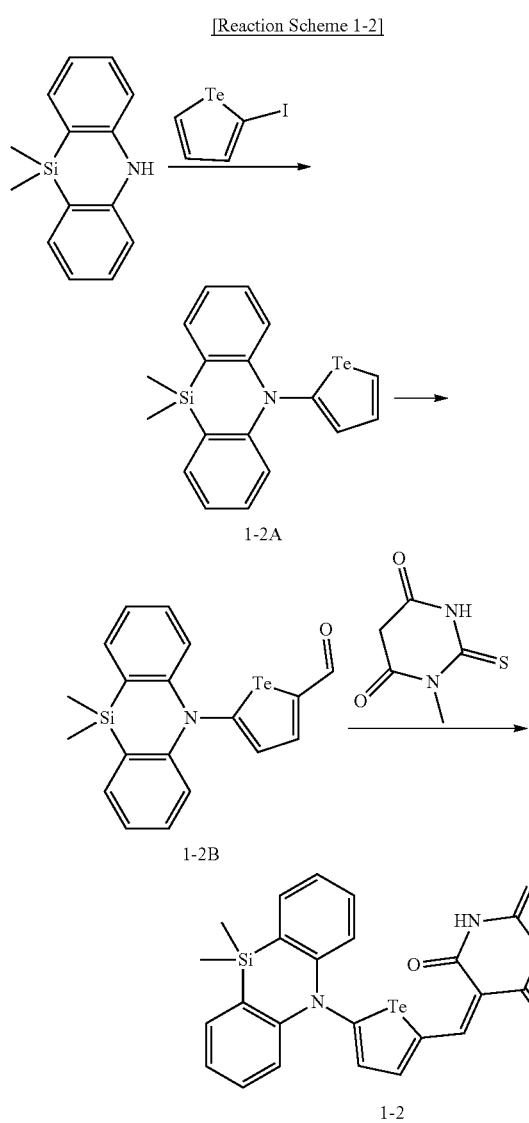

(i) Synthesis of Compound 1-2A 8.34 g (27.3 mmol) of 2-iodotelurophene and 5.59 g (24.8 mmol) of diphenylamine are heated under reflux in 150 ml of anhydrous toluene under the presence of 5 mol % of Pd(dba)2, 5 mol % of P(tBu)3, and 7.15 g (74.4 mmol) of NaOtBu for 2 hours. The obtained product is separated and purified through silica gel column chromatography (in a volume ratio of toluene:hexane=1:4), obtaining 8.0 g (Yield: 80%) of Compound 1-2A (10,10-dimethyl-5-(tellurophen-2-yl)-5,10-dihydrodibenzo[b,e][1,4]azasiline).

(ii) Synthesis of Compound 1-2B 1.11 ml of phosphoryl chloride is added dropwise to 3.19 ml of N,N-dimethylformamide at −15° C. and then, stirred at room temperature (24° C.) for 2 hours. The resultant is slowly added to a mixture of 200 ml of dichloromethane and 3.19 g of Compound 1-2A at −15° C. and then, stirred at room temperature (24° C.) for 30 minutes and concentrated under a reduced pressure. Subsequently, 100 ml of water is added thereto, and an aqueous sodium hydroxide solution is added thereto until pH becomes 14 and then, stirred at room temperature (24° C.) for 2 hours. Then, an organic layer extracted by dichloromethane is washed with an aqueous sodium chloride solution and then, dried with anhydrous magnesium sulfate. The obtained product is separated and purified through silica gel column chromatography (in a volume ratio of hexane:ethylacetate=4:1), obtaining 2.20 g (Yield: 73%) of Compound 1-2B (5-(10,10-dimethyldibenzo[b,e][1,4]azasilin-5(10H)-yl)tellurophene-2-carbaldehyde).

(iii) Synthesis of Compound Represented by Chemical Formula 1-2

2.00 g (4.64 mmol) of Compound 1-2B is suspended in ethanol, and 0.89 g (5.57 mmol) of 1-methyl-2-thioxodihydropyrimidine-4,6(1H,5H)-dione is added thereto and then, reacted at 50° C. for 2 hours, obtaining 2.2 g (Yield: 83%) of a compound represented by Chemical Formula 1-2. The obtained compound is purified through sublimation up to purity of 99.9%.

$^1$H-NMR (500 MHz, Methylene Chloride-d$_2$): δ 8.95 (s, 1H), 8.77 (s, 1H), 8.29 (s, 2H), 8.17 (d, 2H) 7.7 (d, 4H), 7.63 (d, 4H), 7.46 (t, 4H), 7.36 (t, 4H), 6.85 (d, 2H), 3.56 (s, 3H), 3.51 (s, 3H), 0.36 (s, 12H).

Synthesis Example 3: Synthesis of Compound Represented by Chemical Formula 1-3

[Chemical Formula 1-3]

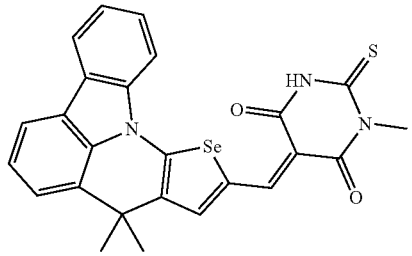

[Reaction Scheme 1-3]

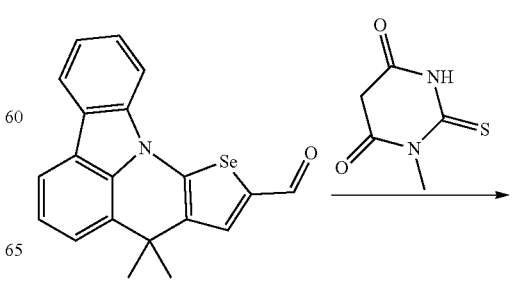

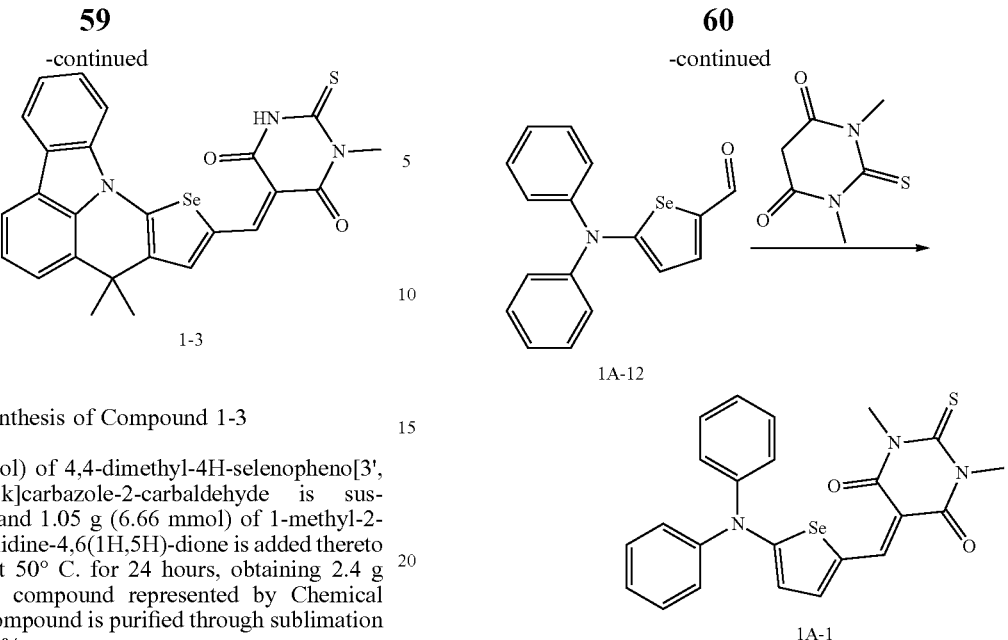

(i) Synthesis of Compound 1-3

2.00 g (5.55 mmol) of 4,4-dimethyl-4H-selenopheno[3',2':5,6]pyrido[3,2,1-jk]carbazole-2-carbaldehyde is suspended in ethanol, and 1.05 g (6.66 mmol) of 1-methyl-2-thioxodihydropyrimidine-4,6(1H,5H)-dione is added thereto and then, reacted at 50° C. for 24 hours, obtaining 2.4 g (Yield: 86%) of a compound represented by Chemical Formula 1-3. The compound is purified through sublimation up to purity of 99.9%.

$^1$H-NMR (500 MHz, Methylene Chloride-d$_2$): δ 8.95 (s, 1H), 8.77 (s, 1H), 8.65 (s, 2H), 8.18 (s, 2H) 8.06 (d, 2H), 7.92 (d, 2H), 7.83 (d, 2H), 7.62 (d, 2H), 7.44 (t, 2H), 7.36 (m, 6H), 3.76 (s, 3H), 3.71 (s, 3H), 1.68 (s, 12H).

Reference Synthesis Example 1A-1: Synthesis of Compound Represented by Chemical Formula 1A-1

[Chemical Formula 1A-1]

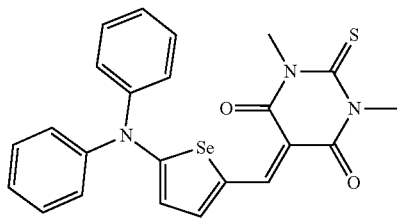

[Reaction Scheme 1A-1]

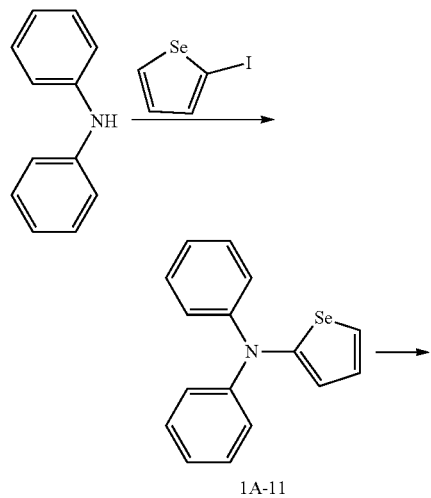

(i) Synthesis of Compound 1A-11

9.48 g (36.9 mmol) of 2-iodoselenophene and 5.68 g (33.5 mmol) of diphenylamine are heated under reflux in 150 ml of anhydrous toluene under the presence of 5 mol % of Pd(dba)2, 5 mol % of P(tBu)3, and 9.67 g (100.6 mmol) of NaOtBu for 2 hours. The obtained product is separated and purified through silica gel column chromatography (in a volume ratio of toluene:hexane=1:4), obtaining 8.0 g (Yield: 80%) of Compound 1A-11 (N,N-diphenylselenophen-2-amine).

(ii) Synthesis of Compound 1A-12

1.46 ml of phosphoryl chloride is added dropwise to 3.56 ml of N,N-dimethylformamide at −15° C. and then, stirred at room temperature (24° C.) for 2 hours. The resultant is slowly added to a mixture of 200 ml of dichloromethane and 3.11 g of Compound 1A-11 at −15° C. and then, stirred at room temperature (24° C.) for 30 minutes and concentrated under a reduced pressure. Subsequently, 100 ml of water is added thereto, and an aqueous sodium hydroxide solution is added thereto until pH becomes 14 and then, stirred at room temperature (24° C.) for 2 hours. Then, an organic layer extracted by dichloromethane is washed with an aqueous sodium chloride solution and then, dried with anhydrous magnesium sulfate. The obtained product is separated and purified through silica gel column chromatography (in a volume ratio of hexane:ethylacetate=4:1), obtaining 2.50 g (Yield: 83%) of Compound 1A-12 (5-(diphenylamino)selenophene-2-carbaldehyde).

(iii) Synthesis of Compound Represented by Chemical Formula 1A-1

2.0 g (6.24 mmol) of Compound 1A-12 is suspended in ethanol, and 1.18 g (6.87 mmol) of 1,3-dimethyl-2-thioxodihydropyrimidine-4,6(1H,5H)-dione is added thereto and then, reacted at 50° C. for 2 hours, obtaining 2.5 g (Yield: 83%) of a compound represented by Chemical Formula 1A-1. The obtained compound is purified through sublimation up to purity of 99.9%.

¹H-NMR (500 MHz, Methylene Chloride-d₂): δ 8.36 (s, 1H), 7.84 (d, 2H), 7.44-7.41 (m, 4H), 7.37-7.33 (m, 6H) 6.50 (d, 1H), 3.64 (s, 3H), 3.58 (s, 3H).

Reference Synthesis Example 1A-2: Synthesis of Compound Represented by Chemical Formula 1A-2

[Chemical Formula 1A-2]

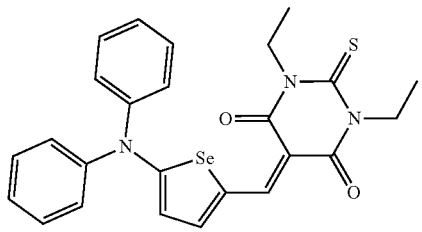

[Reaction Scheme 1A-2]

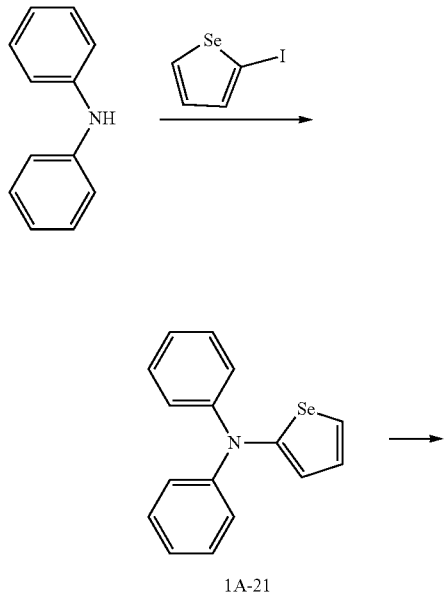

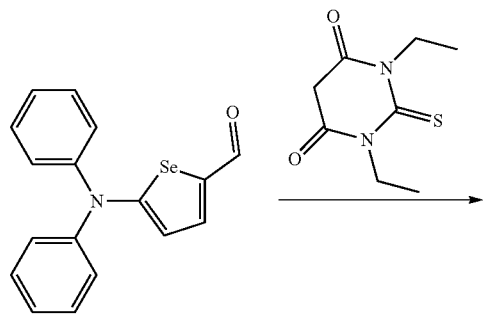

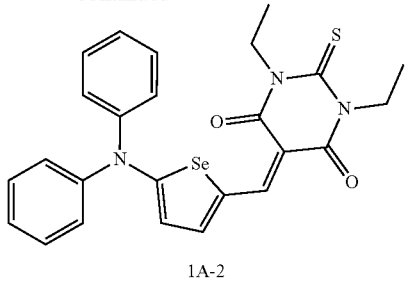

1A-2

(i) Synthesis of Compound 1A-21

9.48 g (36.9 mmol) of 2-iodoselenophene and 5.68 g (33.5 mmol) of diphenylamine are heated under reflux in 150 ml of anhydrous toluene under the presence of 5 mol % of Pd(dba)₂, 5 mol % of P(tBu)₃, and 9.67 g (100.6 mmol) of NaOtBu for 2 hours. The obtained product is separated and purified through silica gel column chromatography (in a volume ratio of toluene:hexane=1:4), obtaining 8.0 g (Yield: 80%) of Compound 1A-21 (N,N-diphenylselenophen-2-amine).

(ii) Synthesis of Compound 1A-22

1.46 ml of phosphoryl chloride is added dropwise to 3.56 ml of N,N-dimethylformamide at −15° C. and then, stirred at room temperature (24° C.) for 2 hours. The resultant is slowly added dropwise to a mixture of 200 ml of dichloromethane and 3.11 g of Compound 1A-21 at −15° C. and then, stirred at room temperature (24° C.) for 30 minutes and concentrated under a reduced pressure. Subsequently, 100 ml of water is added thereto, and an aqueous sodium hydroxide solution is added thereto until pH becomes 14 and then, stirred at room temperature (24° C.) for 2 hours. Then, an organic layer extracted with dichloromethane is washed with an aqueous sodium chloride solution and dried with anhydrous magnesium sulfate. The obtained product is separated and purified through silica gel column chromatography (in a volume ratio of hexane:ethylacetate=4:1), obtaining 2.50 g (Yield: 83%) of Compound 1A-22 (5-(diphenylamino)selenophene-2-carbaldehyde).

(iii) Synthesis of Compound Represented by Chemical Formula 1A-2

1.93 g (5.9 mmol) of Compound 1A-22 is suspended in ethanol, and 1.30 g (6.50 mmol) of 1,3-diethyl-2-thioxodihydropyrimidine-4,6(1H,5H)-dione is added thereto and then, reacted at 50° C. for 2 hours, obtaining 2.3 g (Yield: 77%) of a compound represented by Chemical Formula 1A-2. The obtained compound is purified through sublimation up to purity of 99.9%.

¹H-NMR (500 MHz, Methylene Chloride-d₂): δ 8.36 (s, 1H), 7.84 (d, 1H), 7.44-7.41 (m, 4H), 7.37-7.33 (m, 6H) 6.50 (d, 1H), 4.45 (q, 2H), 4.36 (q, 2H) 3.64 (s, 3H), 3.58 (s, 3H).

Reference Synthesis Example 1B: Synthesis of Compound Represented by Chemical Formula 1B

[Chemical Formula 1B]

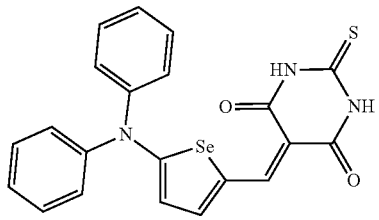

[Reaction Scheme 1B]

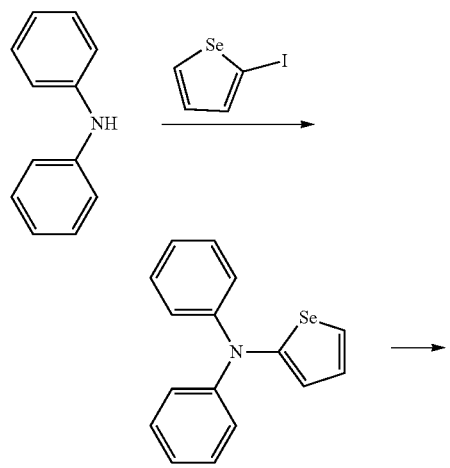

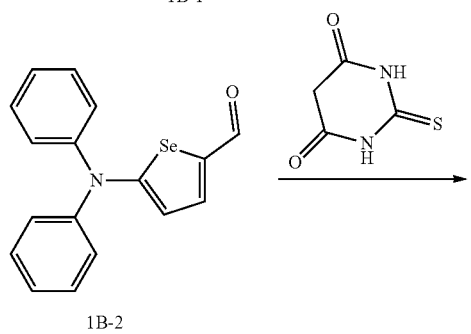

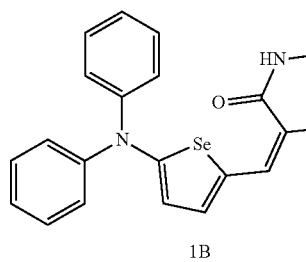

(i) Synthesis of Compound 1B-1

9.48 g (36.9 mmol) of 2-iodoselenophene and 5.68 g (33.5 mmol) of diphenylamine are heated under reflux in 150 ml of anhydrous toluene under the presence of 5 mol % of Pd(dba)$_2$, 5 mol % of P(tBu)$_3$, and 9.67 g (100.6 mmol) of NaOtBu for 2 hours. The obtained product is separated and purified through silica gel column chromatography (in a volume ratio of toluene:hexane=1:4), obtaining 8.0 g (Yield: 80%) of Compound 1B-1 (N,N-diphenylselenophen-2-amine).

(ii) Synthesis of Compound 1B-2

1.46 ml of phosphoryl chloride is added dropwise to 3.56 ml of N,N-dimethylformamide at −15° C. and then, stirred at room temperature (24° C.) for 2 hours. The resultant is slowly added dropwise to a mixture of 200 ml of dichloromethane and 3.11 g of Compound 1B-1 at −15° C. and then, stirred at room temperature (24° C.) for 30 minutes and concentrated under a reduced pressure. Then, 100 ml of water is added thereto, and an aqueous sodium hydroxide solution is added thereto until pH becomes 14 and then, stirred at room temperature (24° C.) for 2 hours. Subsequently, an organic layer extracted by dichloromethane is washed with an aqueous sodium chloride solution and dried with anhydrous magnesium sulfate. The obtained product is separated and purified through silica gel column chromatography (in a volume ratio of hexane:ethylacetate=4:1), obtaining 2.50 g (Yield: 83%) of Compound 1B-2 (5-(diphenylamino)selenophene-2-carbaldehyde).

(iii) Synthesis of Compound Represented by Chemical Formula 1B 2.16 g (6.63 mmol) of Compound 1B-2 is suspended in ethanol, and 1.05 g (7.29 mmol) of 2-thioxodihydropyrimidine-4,6(1H,5H)-dione is added thereto and then, reacted at 50° C. for 2 hours, obtaining 2.4 g (Yield: 80%) of a compound represented by Chemical Formula 1B. The obtained compound is purified through sublimation up to purity of 99.9%.

$^1$H-NMR (500 MHz, Methylene Chloride-d$_2$): δ 8.95 (s, 1H), 8.77 (s, 1H), 8.36 (s, 1H), 7.84 (d, 1H), 7.44-7.41 (m, 4H), 7.37-7.33 (m, 6H) 6.50 (d, 1H).

Reference Synthesis Example 2A: Synthesis of Compound Represented by Chemical Formula 2A

[Chemical Formula 2A]

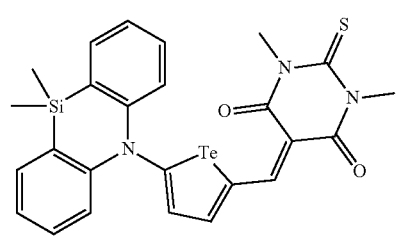

[Reaction Scheme 2A]

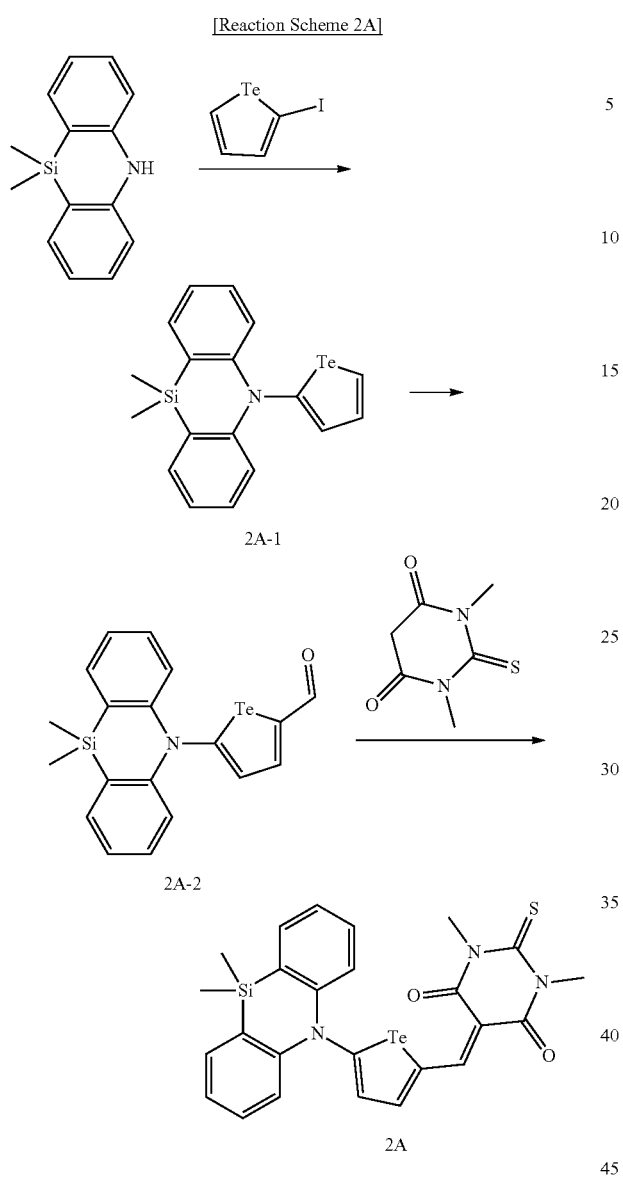

2A-1

2A-2

2A (i) Synthesis of Compound 2A-1

8.34 g (27.3 mmol) of 2-iodotellurophene and 5.59 g (24.8 mmol) of diphenylamine are heated under reflux in 150 ml of anhydrous toluene under the presence of 5 mol % of Pd(dba)$_2$, 5 mol % of P(tBu)$_3$, and 7.15 g (74.4 mmol) of NaOtBu for 2 hours. The obtained product is separated and purified through silica gel column chromatography (in a volume ratio of toluene:hexane=1:4), obtaining 8.0 g (Yield: 80%) of Compound 2A-1 (10,10-dimethyl-5-(tellurophen-2-yl)-5,10-dihydrodibenzo[b,e][1,4]azasiline).

(ii) Synthesis of Compound 2A-2

1.11 ml of phosphoryl chloride is added dropwise to 3.19 ml of N,N-dimethylformamide at −15° C. and then, stirred at room temperature (24° C.) for 2 hours. The resultant is slowly added dropwise to a mixture of 200 ml of dichloromethane and 3.19 g of Compound 2A-1 at −15° C. and then, stirred at room temperature (24° C.) for 30 minutes and concentrated under a reduced pressure. Subsequently, 100 ml of water is added thereto, and an aqueous sodium hydroxide solution is added thereto until pH becomes 14 and then, stirred at room temperature (24° C.) for 2 hours. Then, an organic layer extracted with dichloromethane is washed with an aqueous sodium chloride solution and dried with anhydrous magnesium sulfate. The obtained product is separated and purified through silica gel column chromatography (in a volume ratio of hexane:ethylacetate=4:1), obtaining 2.20 g (Yield: 73%) of Compound 2A-2 (5-(10,10-dimethyldibenzo[b,e][1,4]azasilin-5(10H)-yl)tellurophene-2-carbaldehyde).

(iii) Synthesis of Compound Represented by Chemical Formula 2A 2.21 g (5.13 mmol) of Compound 2A-2 is suspended in ethanol, and 0.97 g (5.64 mmol) of 1,3-dimethyl-2-thioxo-dihydropyrimidine-4,6(1H,5H)-dione is added thereto and then, reacted at 50° C. for 2 hours, obtaining 2.4 g (Yield: 80%) of a compound represented by Chemical Formula 2A. The obtained compound is purified through sublimation up to purity of 99.9%.

$^1$H-NMR (500 MHz, Methylene Chloride-d$_2$): δ 8.49 (s, 1H), 8.25 (d, 2H) 7.8 (d, 2H), 7.70 (d, 2H), 7.55 (t, 2H), 7.44 (t, 2H), 6.94 (d, 1H), 3.71 (s, 3H), 3.66 (s, 3H), 0.44 (s, 6H).

Reference Synthesis Example 2B: Synthesis of Compound Represented by Chemical Formula 2B

[Chemical Formula 2B]

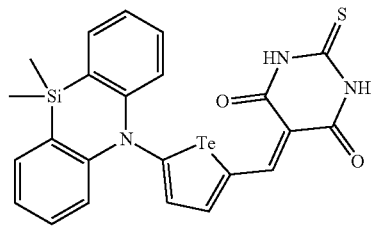

[Reaction Scheme 2B]

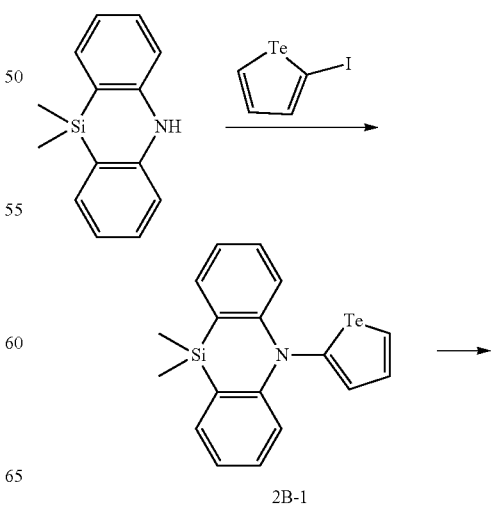

2B-1

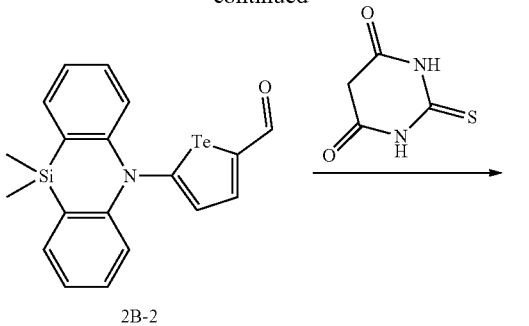

2B-2

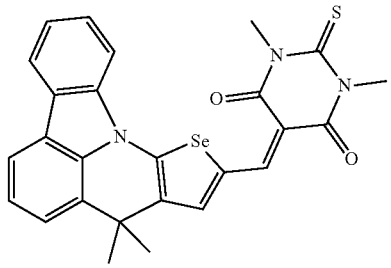

2B (i) Synthesis of Compound 2B-1

8.34 g (27.3 mmol) of 2-iodotellurophene and 5.59 g (24.8 mmol) of diphenylamine are heated under reflux in 150 ml of anhydrous toluene under the presence of 5 mol % of Pd(dba)$_2$, 5 mol % of P(tBu)$_3$, and 7.15 g (74.4 mmol) of NaOtBu for 2 hours. The product is separated and purified through silica gel column chromatography (in a volume ratio of toluene:hexane=1:4), obtaining 8.0 g (Yield: 80%) of Compound 2B-1 (10,10-dimethyl-5-(tellurophen-2-yl)-5,10-dihydrodibenzo[b,e][1,4]azasiline).

(ii) Synthesis of Compound 2B-2

1.11 ml of phosphoryl chloride is added dropwise to 3.19 ml of N,N-dimethylformamide at −15° C. and then, stirred at room temperature (24° C.) for 2 hours. The resultant is slowly added dropwise to a mixture of 200 ml of dichloromethane and 3.19 g of Compound 2B-1 at −15° C. and then, stirred at room temperature (24° C.) for 30 minutes and concentrated under a reduced pressure. Subsequently, 100 ml of water is added thereto, and an aqueous sodium hydroxide solution is added thereto until pH becomes 14 and then, stirred at room temperature (24° C.) for 2 hours. Then, an organic layer extracted with dichloromethane is washed with an aqueous sodium chloride solution and dried with anhydrous magnesium sulfate. The obtained product is separated and purified through silica gel column chromatography (in a volume ratio of hexane:ethyl acetate=4:1), obtaining 2.20 g (Yield 73%) of Compound 2B-2 (5-(10,10-dimethyldibenzo[b,e][1,4]azasilin-5(10H)-yl)tellurophene-2-carbaldehyde).

(iii) Synthesis of Compound Represented by Chemical Formula 2B 2.21 g (5.13 mmol) of Compound 2B-2 is suspended in ethanol, 0.81 g (5.64 mmol) of 2-thioxodihydropyrimidine-4,6(1H,5H)-dione is added thereto and then, reacted at 50° C. for 2 hours, obtaining 2.1 g (Yield: 70%) of a compound represented by Chemical Formula 2B. The obtained compound is purified through sublimation up to purity of 99.9%.

$^1$H-NMR (500 MHz, Methylene Chloride-d$_2$): δ 8.95 (s, 1H), 8.77 (s, 1H), 8.49 (s, 1H), 8.25 (d, 2H) 7.8 (d, 2H), 7.70 (d, 2H), 7.55 (t, 2H), 7.44 (t, 2H), 6.94 (d, 1H), 0.44 (s, 6H).

Reference Synthesis Example 3A: Synthesis of Compound Represented by Chemical Formula 3A

[Chemical Formula 3A]

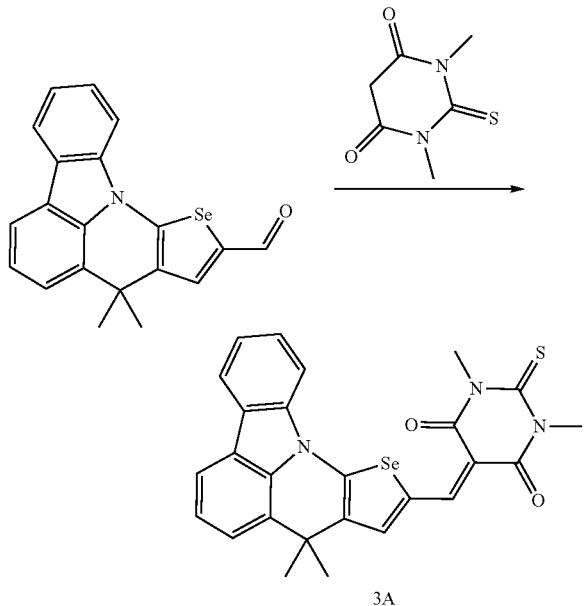

3A

[Reaction Scheme 3A]

(i) Synthesis of Compound 3A 2.11 g (5.79 mmol) of 4,4-dimethyl-4H-selenopheno[3',2': 5,6]pyrido[3,2,1-jk]carbazole-2-carbaldehyde is suspended in ethanol, and 1.10 g (6.36 mmol) of 1,3-dimethyl-2-thioxodihydropyrimidine-4,6(1H,5H)-dione is added thereto and then, reacted at 50° C. for 24 hours, obtaining 2.2 g (Yield: 73%) of a compound represented by Chemical Formula 3A. The obtained compound is purified through sublimation up to purity of 99.9%.

$^1$H-NMR (500 MHz, Methylene Chloride-d$_2$): δ 8.65 (s, 1H), 8.18 (s, 1H) 8.06 (d, 1H), 7.92 (d, 1H), 7.83 (d, 1H), 7.62 (d, 1H), 7.44 (t, 1H), 7.36 (m, 3H), 3.76 (s, 3H), 3.71 (s, 3H), 1.68 (s, 6H).

Reference Synthesis Example 3B: Synthesis of Compound Represented by Chemical Formula 3B

[Chemical Formula 3B]

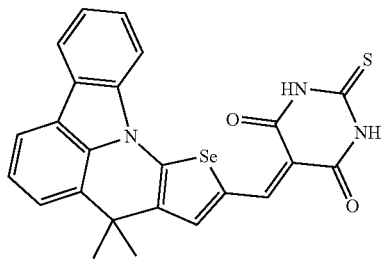

[Reaction Scheme 3B]

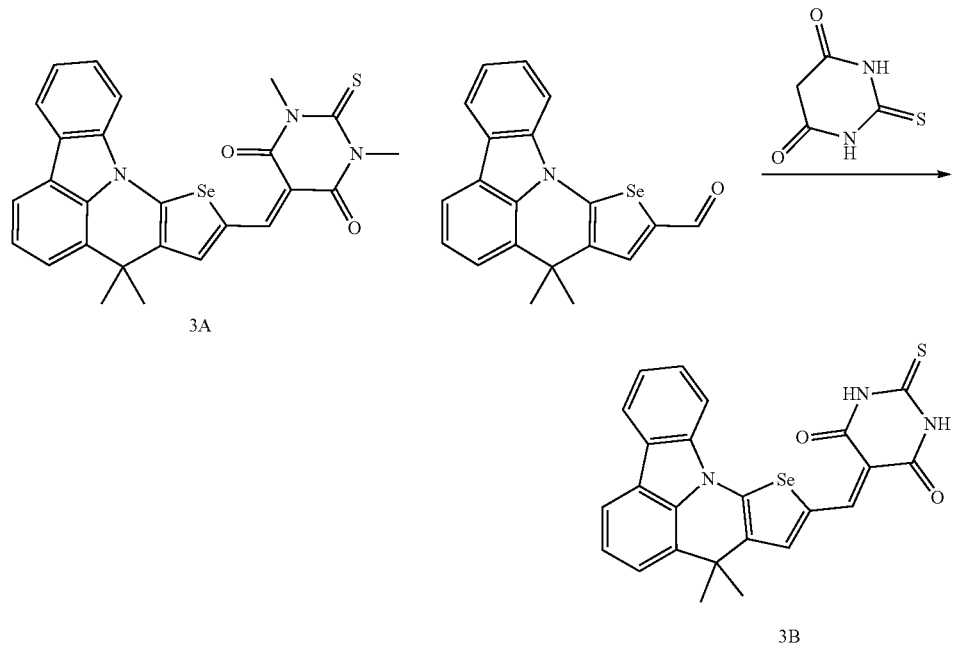

(i) Synthesis of Compound 3B 2.23 g (6.12 mmol) of 4,4-dimethyl-4H-selenopheno[3',2': 5,6]pyrido[3,2,1-jk]carbazole-2-carbaldehyde is suspended in ethanol, and 0.97 g (6.73 mmol) of 1,3-dimethyl-2-thioxodihydropyrimidine-4,6(1H,5H)-dione is added thereto and then, reacted at 50° C. for 24 hours, obtaining 2.0 g (Yield: 67%) of a compound represented by Chemical Formula 3B. The obtained compound is purified through sublimation up to purity of 99.9%.

$^1$H-NMR (500 MHz, Methylene Chloride-$d_2$): δ 8.65 (s, 1H), 8.18 (s, 1H) 8.06 (d, 1H), 7.92 (d, 1H), 7.83 (d, 1H), 7.62 (d, 1H), 7.44 (t, 1H), 7.36 (m, 3H), 1.68 (s, 6H).

Evaluation 1: Energy Level of Compounds According to Synthesis Examples 1 to 3 and Reference Synthesis Examples 1A-1 to 3B Each compound according to Synthesis Examples 1 to 3 and Reference Synthesis Examples 1A to 3B and C60 (N-type semiconductor) are codeposited in a volume ratio of 1:1 to form thin films, and each thin film is measured with respect to HOMO by using an AC-3 photoelectron spectrophotometer (RIKEN KEIKI), and LUMO thereof is calculated by using a bandgap obtained through Cary 5000 UV spectroscopy (Varian Medical Systems, Inc.). The results of Synthesis Examples 1 to 3 are shown in Table 1.

TABLE 1

| Compounds | HOMO (eV) | LUMO (eV) |
| --- | --- | --- |
| Synthesis Example 1 | −5.64 | −2.69 |
| Synthesis Example 2 | −5.62 | −2.69 |
| Synthesis Example 3 | −5.79 | −3.00 |

Referring to Table 1, energy levels of the compounds according to Synthesis Examples 1 to 3 exhibit that the compounds are appropriate as a p type semiconductor.

Evaluation 2: Thermal Stability of Compounds

The compounds according to Synthesis Examples 1 to 3 are evaluated with respect to thermal stability by measuring a temperature ($Ts_{10}$, a deposition temperature) where 10 wt % thereof is decomposed at 10 Pa. In addition, a melting point (Tm) thereof is measured under a normal pressure condition in a differential thermal analysis (DTA) method (a temperature increase rate: 10° C./min). The results are shown in Table 2.

TABLE 2

| Synthesis Example | Tm (° C.) | Ts10 (10 wt %, 10 Pa) (° C.) | ΔT (Tm-Ts$_{10}$) (° C.) |
| --- | --- | --- | --- |
| Synthesis Example 1 | 257 | 230 | 27 |
| Synthesis Example 2 | 328 | 248 | 80 |
| Synthesis Example 3 | 389 | 270 | 119 |

When a compound has a lower melting point than a deposition temperature during the vacuum deposition, the compound may be decomposed and simultaneously gasified and thus fails in being formed into a film. Accordingly, the melting point of a compound may desirably be higher than the deposition temperature. Referring to Table 2, the compounds according to Synthesis Examples 1 to 3 exhibit a higher melting point than a deposition temperature by greater than or equal to 27° C. Accordingly, the compounds according to Synthesis Examples 1 to 5 have a large difference between the melting point and the deposition temperature and thus may secure process stability.

Example 1: Manufacture of Photoelectric Device

An about 150 nm-thick anode is formed by sputtering ITO on a glass substrate, and a 100 nm-thick active layer is formed thereon by codepositing a compound represented by Chemical Formula 1-1 according to Synthesis Example 1 (p-type semiconductor compound) and C60 (n-type semiconductor compound) in a volume ratio of 1:1. Subsequently, a 10 nm-thick molybdenum oxide (MoO$_x$, 0<x≤3) thin film is formed thereon as a charge auxiliary layer. On the molybdenum oxide thin film, a 7 nm-thick cathode is formed by sputtering ITO, manufacturing an organic photoelectric device.

Examples 2 and 3: Manufacture of Photoelectric Device

Photoelectric devices according to Examples 2 and 3 are manufactured according to the same method as Example 1 except that the compounds according to Synthesis Examples 2 and 3 are used respectively instead of the compound according to Synthesis Example 1.

Reference Examples 1A-1 to 3B: Manufacture of Photoelectric Device

Photoelectric devices according to Reference Examples 1A-1 to 3B are manufactured according to the same method as Example 1 except that the compounds according to Reference Synthesis Example 1A-1 to 3B are used respectively instead of the compound according to Synthesis Example 1.

Evaluation 3: Light Absorption Characteristics of Photoelectric Device

Light absorption characteristics (maximum absorption wavelength and absorption coefficient) in an ultraviolet (UV)-visible (UV-Vis) region of each photoelectric device according to Examples 1 to 3 and Reference Examples 1A-1 to 3B are evaluated using Cary 5000 UV Spectroscopy (Varian Medical Systems). The results are shown in Table 3.

TABLE 3

| Nos. | $\lambda_{max}$ (nm) | Abs. coeff. ($10^4$ cm$^{-1}$) |
| --- | --- | --- |
| Example 1 | 530 | 9.06 |
| Example 2 | 540 | 8.92 |
| Example 3 | 560 | 8.97 |
| Reference Example 1A-1 | 530 | 6.23 |
| Reference Example 1A-2 | 529 | 5.55 |
| Reference Example 1B | 530 | 6.09 |
| Reference Example 2A | 540 | 8.07 |
| Reference Example 2B | 540 | 7.81 |
| Reference Example 3A | 554 | 7.39 |
| Reference Example 3B | 554 | 7.05 |

Referring to Table 3, the photoelectric devices of Examples 1 to 3 respectively including the compounds according to Synthesis Examples 1 to 3 exhibit excellent absorption characteristics in a green wavelength region and a high absorption coefficient (absorption intensity), compared with the photoelectric devices of Reference Examples 1A-1 to 3B.

Evaluation 4: Quantum Efficiency of Photoelectric Device

The photoelectric devices of Examples 1 to 3 and Reference Examples 1B, 2B, and 3B are evaluated with respect to external quantum efficiency (EQE). The external quantum efficiency is measured by using an IPCE measurement system (McScience Inc., Korea). After calibrating the equipment with an Si photodiode (Hamamatsu Photonics K.K., Japan), the photoelectric devices according to Examples 1 to 3 and Reference Examples 1B, 2B, and 3B are mounted thereon and measured with respect to the external quantum efficiency in a wavelength region ranging from about 350 nm to 750 nm.

The external quantum efficiency (EQE) measured by the IPCE measuring apparatus indicates the amount of charges formed by the amount of externally incident light, and internal quantum efficiency (IQE) is obtained as the amount of converted charges relative to the amount of light absorbed in an active layer of the device by measuring a ratio of the amount of light absorbed in an absorption layer based on the amount of the entire incident light with UV-vis and multiplying the ratio by the EQE after removing reflected or transmitted light, when the incident light of the device is reflected or transmitted without being absorbed before being absorbed in the absorption layer.

The external quantum efficiency (EQE) and internal quantum efficiency (IQE) of the organic photoelectric devices Examples 1 to 3 and Reference Examples 1B, 2B, and 3B are measured at 3 V, and the results are shown in Table 4.

TABLE 4

|  | EQE (%) | IQE (%) |
| --- | --- | --- |
| Example 1 | 54 | 84 |
| Example 2 | 71 | 87 |
| Example 3 | 75 | 91 |
| Reference Example 1B | 13 | 17 |
| Reference Example 2B | 17 | 15 |
| Reference Example 3B | 15 | 15 |

Referring to Table 4, the photoelectric devices of Examples 1 to 3 respectively including the compounds of Synthesis Examples 1 to 3 exhibit excellent external quantum efficiency (EQE) and internal quantum efficiency (IQE), compared with the photoelectric devices of Reference Examples 1B, 2B, and 3B.

Evaluation 5: Evaluation of Remaining Charges and Dark Current of Photoelectric Device The photoelectric devices of Examples 1 to 3 and Reference Examples 1A-1 to 3B are evaluated with respect to remaining charges and a dark current. The remaining charges are charges which are photoelectrically converted but not processed into signals in one frame and remain and thus are read again in the next frame, and an amount of the remaining charges in the next frame is measured. The amount of the remaining charges is measured by irradiating light in a green wavelength (532 nm) region where photoelectric conversion may occur for predetermined time and turning it off and then, integrating a current, which is measured by a unit of $10^{-6}$ seconds with an Oscilloscope equipment, with time. The amount of the remaining charges is evaluated with reference to light of 5000 lux by an h+/μm² unit.

The dark current is measured by using the IPCE measurement system (McScience Inc., Korea). After calibrating the equipment with the Si photodiode (Hamamatsu Photonics K.K., Japan), the photoelectric devices according to Examples 1 to 3 and Reference Examples 1A-1 to 3B are mounted on the equipment and measured with respect to the dark current in a wavelength region ranging from about 350 nm to 750 nm.

The remaining charges and dark current results of photoelectric devices Examples 1 to 3 and Reference Examples 1A-1, 1B, 2B, and 3B are shown in Table 5.

TABLE 5

| Nos. | Remaining charge (h+/μm²) | Dark current (h+/s/μm²) |
|---|---|---|
| Example 1 | 168 | 3 |
| Example 2 | 177 | 8 |
| Example 3 | 37 | 7 |
| Reference Example 1A-1 | 531 | 3641 |
| Reference Example 1B | 751 | 76000 |
| Reference Example 2B | 804 | 4865 |
| Reference Example 3B | 305 | 54500 |

Referring to Table 5, the photoelectric devices of Examples 1 to 3 exhibit lower remaining charges and dark currents than the photoelectric devices of Reference Examples 1A-1, 1B, 2B, and 3B.

While this disclosure has been described in connection with what is presently considered to be practical example embodiments, it is to be understood that the inventive concepts are not limited to such example embodiments. On the contrary, the scope of the inventive concepts is intended to cover various modifications and equivalent arrangements included within the spirit and scope of the appended claims.

<Description of Symbols>

10: first electrode
20: second electrode
30: active layer
40, 45: charge auxiliary layer
50B, 50R: photo-sensing device
55: charge storage
60: lower insulation layer
70, 72: color filter layer
70B, 72B: blue filter
70R, 72R: red filter
85: through-hole
80: upper insulation layer <Description of Symbols>

100, 200: photoelectric device
300, 400, 500: organic CMOS image sensor
310: semiconductor substrate

What is claimed is:

1. A compound represented by Chemical Formula 1:

[Chemical Formula 1]

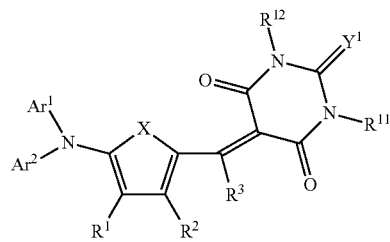

wherein, in Chemical Formula 1, $Ar^1$ and $Ar^2$ are each independently a substituted or unsubstituted 5-membered aromatic ring, a substituted or unsubstituted 6-membered aromatic ring, or a condensed ring of two or more, wherein $Ar^1$ and $Ar^2$ are each independently present or linked with each other to provide a first condensed ring, X is S, Se, Te, O, S(=O), S(=O)$_2$, NR$^a$, or SiR$^b$R$^c$, wherein R$^a$, R$^b$, and R$^c$ are each independently hydrogen or a substituted or unsubstituted C1 to C10 alkyl group, $R^1$ to $R^3$ are each independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, or a combination thereof, wherein $R^1$ and $R^2$ are each independently present or linked with each other to provide a ring, $Y^1$ is O, S, Se, Te, or C(R$^e$) (CN), wherein R$^e$ is hydrogen, a cyano group (—CN), or a C1 to C10 alkyl group, and $R^{11}$ and $R^{12}$ are each independently hydrogen, deuterium, a C1 to C10 alkyl group, or a C6 to C10 aryl group, wherein one of $R^{11}$ or $R^{12}$ is hydrogen or deuterium, and another one of $R^{11}$ or $R^{12}$ is a C1 to C10 alkyl group or a C6 to C10 aryl group, wherein $Ar^2$ and $R^1$ are each independently present, or $Ar^2$ and $R^1$ are linked with each other to provide a second condensed ring and $Ar^1$ and $Ar^2$ are linked with each other to provide the first condensed ring.

2. The compound of claim 1, wherein Chemical Formula 1 includes a cyclic group represented by Chemical Formula 2, and the cyclic group represented by Chemical Formula 2 is a cyclic group represented by Chemical Formula 2-1, Chemical Formula 2-2, or Chemical Formula 2-3:

[Chemical Formula 2]

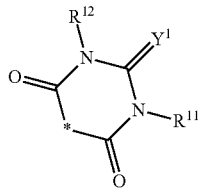

wherein, in Chemical Formula 2,
$Y^1$, $R^{11}$, and $R^{12}$ are the same as $Y^1$, $R^{11}$, and $R^{12}$, respectively, in Chemical Formula 1,

[Chemical Formula 2-1]

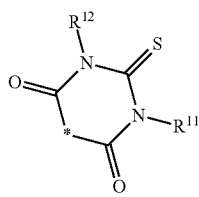

[Chemical Formula 2-2]

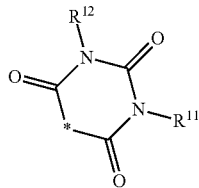

[Chemical Formula 2-3]

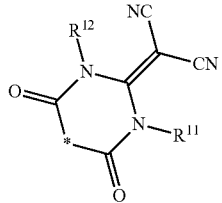

wherein, in Chemical Formula 2-1, Chemical Formula 2-2, and Chemical Formula 2-3,
$R^{11}$ and $R^{12}$ are the same as $R^{11}$ and $R^{12}$, respectively, in Chemical Formula 1.

3. The compound of claim 1, wherein in Chemical Formula 1, X is included in an X-containing 5-membered ring and $R^1$ and $R^2$ are linked to each other to provide an additional ring, and a portion of Chemical Formula 1 defined by the X-containing 5-membered ring and the additional ring is represented by Chemical Formula 3-1 or Chemical Formula 3-2:

[Chemical Formula 3-1]

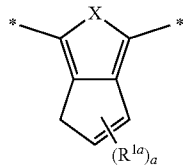

[Chemical Formula 3-2]

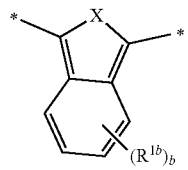

wherein, in Chemical Formula 3-1 and Chemical Formula 3-2,
X is S, Se, Te, O, S(=O), S(=O)$_2$, NR$^a$, or SiR$^b$R$^c$, wherein R$^a$, R$^b$, and R$^c$ are each independently hydrogen or a substituted or unsubstituted C1 to C10 alkyl group,
$R^{1a}$ and $R^{1b}$ is hydrogen, a C1 to C10 alkyl group, a C6 to C10 aryl group, a C2 to C10 heteroaryl group, or a halogen, and a and b are each independently an integer of 1 to 4.

4. The compound of claim 1, wherein in Chemical Formula 1, at least one of Ar$^1$ or Ar$^2$ comprises a heteroatom selected from nitrogen (N), sulfur(S), and selenium (Se) at a 1$^{st}$ position of Chemical Formula 1.

5. The compound of claim 1, wherein *—N(Ar$^1$) (Ar$^2$) of Chemical Formula 1 is represented by Chemical Formula 4-1:

[Chemical Formula 4-1]

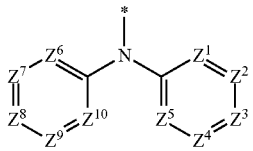

wherein, in Chemical Formula 4-1,
$Z^1$ to $Z^{10}$ are each independently N or CR$^a$, wherein R$^a$ is hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof,
when $Z^1$ to $Z^{10}$ are CR$^a$, R$^a$'s are present independently or two adjacent ones of $Z^1$ to $Z^{10}$ are linked to each other to provide a 5-membered aromatic ring or a 6-membered aromatic ring, and
* is a linking point with Chemical Formula 1.

6. The compound of claim 1, wherein *—N(Ar$^1$) (Ar$^2$) of Chemical Formula 1 is represented by Chemical Formula 4-2:

[Chemical Formula 4-2]

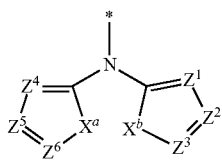

wherein, in Chemical Formula 4-2,
X$^a$ and X$^b$ are each independently —O—, —S—, —Se—, —Te—, —NR$^a$—, —SiR$^b$R$^c$—, or —GeR$^d$R$^e$—, wherein R$^a$, R$^b$, R$^c$, R$^d$, and R$^e$ are each independently hydrogen, a halogen, a substituted or unsubstituted C1 to C10 alkyl group, or a substituted or unsubstituted C6 to C10 aryl group, $Z^1$ to $Z^6$ are each independently N or $CR^x$, wherein $R^x$ is hydrogen, a C1 to C6 alkyl group, a C1 to C10 haloalkyl group, $-SiH_3$, a C1 to C10 alkylsilyl group, $-NH_2$, a C1 to C10 alkylamine group, a C6 to C12 aryl group, a C3 to C12 heteroaryl group, a halogen, a cyano group, or a combination thereof, when $Z^1$ to $Z^6$ are $CR^x$, $R^x$'s are present independently or two adjacent ones of $Z^1$ to $Z^6$ may be linked to each other to provide a 5-membered aromatic ring or a 6-membered aromatic ring, and

* is a linking point with Chemical Formula 1.

7. The compound of claim 1, wherein $Ar^1$ and $Ar^2$ of Chemical Formula 1 are linked to each other to form the first condensed ring, and *—$N(Ar^1)(Ar^2)$ is represented by Chemical Formula 4-3:

[Chemical Formula 4-3]

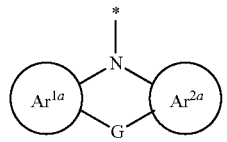

wherein, in Chemical Formula 4-3, $Ar^{1a}$ and $Ar^{2a}$ are each independently a substituted or unsubstituted 5-membered aromatic ring, a substituted or unsubstituted 6-membered aromatic ring, or a condensed ring of two or more, and G is $-(CR^dR^e)_n-$, $-O-$, $-S-$, $-Se-$, $-Te-$, $-N=$, $-NR^f-$, $-SiR^gR^h-$, $-SiR^{gg}R^{hh}-$, $-GeR^iR^j-$, $-GeR^{ii}R^{jj}-$, $-(C(R^m)=C(R^n))-$, $-(C(R^{mm})=C(R^{nn}))-$, or a single bond, wherein $R^d$, $R^e$, $R^f$, $R^g$, $R^h$, $R^i$, $R^j$, $R^m$, and $R^n$ are each independently hydrogen, a halogen, a substituted or unsubstituted C1 to C10 alkyl group, or a substituted or unsubstituted C6 to C10 aryl group, $R^{gg}$ and $R^{hh}$ are linked to each other to provide a first ring structure, $R^{ii}$ and $R^{jj}$ are linked to each other to provide a second ring structure, $R^{mm}$ and $R^{nn}$ are linked to each other to provide a third ring structure, and n of $-(CR^dR^e)_n-$ is 1 or 2.

8. The compound of claim 7, wherein Chemical Formula 4-3 is represented by Chemical Formula 4-3a, Chemical Formula 4-3b, or Chemical Formula 4-3c:

[Chemical Formula 4-3a]

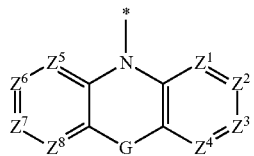

wherein, in Chemical Formula 4-3a,

G is the same as G in Chemical Formula 4-3, $Z^1$ to $Z^8$ are each independently N or $CR^x$, wherein $R^x$ is hydrogen, a C1 to C6 alkyl group, a C1 to C10 haloalkyl group, $-SiH_3$, a C1 to C10 alkylsilyl group, $-NH_2$, a C1 to C10 alkylamine group, a C6 to C12 aryl group, a C3 to C12 heteroaryl group, a halogen, a cyano group, or a combination thereof, when $Z^1$ to $Z^8$ are $CR^x$, $R^x$'s are present independently or two adjacent ones of $Z^1$ to $Z^8$ are linked to each other to provide a 5-membered aromatic ring or a 6-membered aromatic ring, and

* is a linking point with Chemical Formula 1,

[Chemical Formula 4-3b]

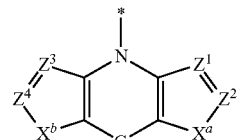

[Chemical Formula 4-3c]

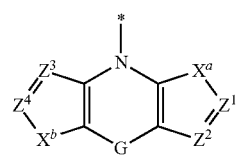

wherein, in Chemical Formula 4-3b and Chemical Formula 4-3c,

G is the same as G in Chemical Formula 4-3, $X^a$ and $X^b$ are each independently $-O-$, $-S-$, $-Se-$, $-Te-$, $-NR^p-$, $-SiR^qR^r-$, or $-GeR^sR^t-$, wherein $R^p$, $R^q$, $R^r$, $R^s$, and $R^t$ are each independently hydrogen, a halogen, a substituted or unsubstituted C1 to C10 alkyl group, or a substituted or unsubstituted C6 to C10 aryl group, $Z^1$ to $Z^4$ are each independently N or $CR^x$, wherein $R^x$ is hydrogen, a C1 to C6 alkyl group, a C1 to C10 haloalkyl group, $-SiH_3$, a C1 to C10 alkylsilyl group, $-NH_2$, a C1 to C10 alkylamine group, a C6 to C12 aryl group, a C3 to C12 heteroaryl group, a halogen, a cyano group, or a combination thereof, and when $Z^1$ to $Z^4$ are $CR^x$, $R^x$'s are present independently or two adjacent ones of $Z^1$ to $Z^4$ are linked to each other to provide a 5-membered aromatic ring or a 6-membered aromatic ring.

9. The compound of claim 8, wherein Chemical Formula 4-3a is represented by one of Chemical Formula 4-3aa to Chemical Formula 4-3al:

(4-3aa)

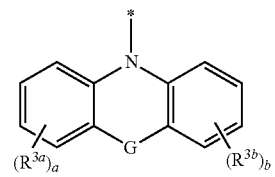

(4-3ab)

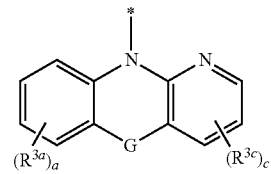

-continued (4-3ac)
(4-3ad)
(4-3ae)
(4-3af)
(4-3ag)
(4-3ah)
(4-3ai)
(4-3aj)

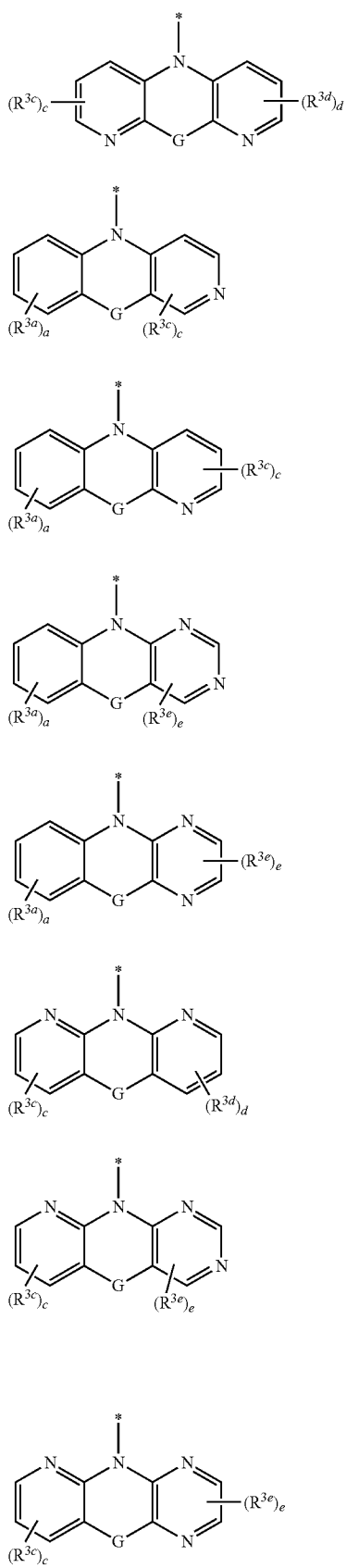

-continued (4-3ak)
(4-3al)

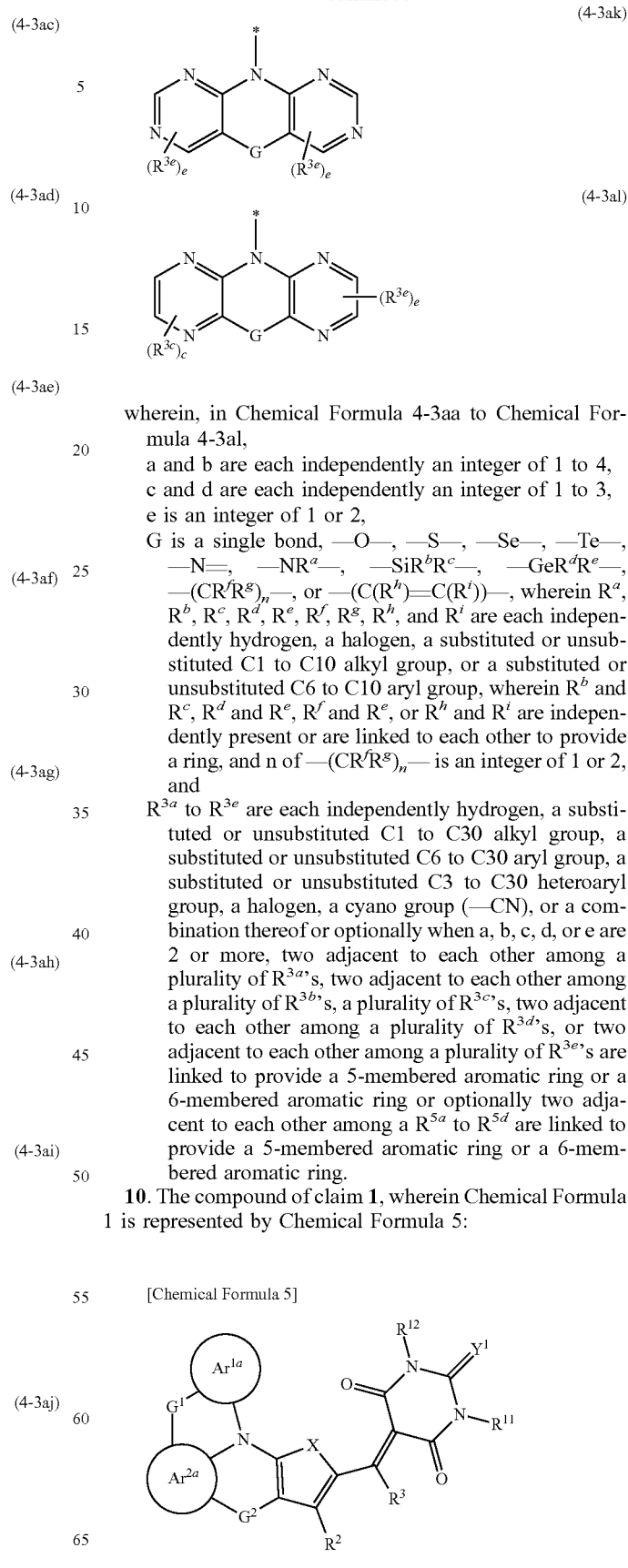

wherein, in Chemical Formula 4-3aa to Chemical Formula 4-3al,
a and b are each independently an integer of 1 to 4,
c and d are each independently an integer of 1 to 3,
e is an integer of 1 or 2,
G is a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ are each independently hydrogen, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or are linked to each other to provide a ring, and n of —(CR$^f$R$^g$)$_n$— is an integer of 1 or 2, and
R$^{3a}$ to R$^{3e}$ are each independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), or a combination thereof or optionally when a, b, c, d, or e are 2 or more, two adjacent to each other among a plurality of R$^{3a}$'s, two adjacent to each other among a plurality of R$^{3b}$'s, a plurality of R$^{3c}$'s, two adjacent to each other among a plurality of R$^{3d}$'s, or two adjacent to each other among a plurality of R$^{3e}$'s are linked to provide a 5-membered aromatic ring or a 6-membered aromatic ring or optionally two adjacent to each other among a R$^{5a}$ to R$^{5d}$ are linked to provide a 5-membered aromatic ring or a 6-membered aromatic ring.

10. The compound of claim 1, wherein Chemical Formula 1 is represented by Chemical Formula 5:

[Chemical Formula 5]

wherein, in Chemical Formula 5,
   X, $R^2$, $R^3$, $Y^1$, $R^{11}$, and $R^{12}$ are the same as X, $R^2$, $R^3$, $Y_1$, $R^{11}$, and $R^{12}$, respectively, in Chemical Formula 1,
   $Ar^{1a}$ and $Ar^{2a}$ are each independently a substituted or unsubstituted 5-membered aromatic ring, a substituted or unsubstituted 6-membered aromatic ring, or a condensed ring of two or more, and
   $G^1$ and $G^2$ are each independently —$(CR^dR^e)_n$—, —O—, —S—, —Se—, —Te—, —N═, —$NR^f$—, —$SiR^gR^h$—, —$SiR^{gg}R^{hh}$—, —$GeR^iR^j$—, —$GeR^{ii}R^{ij}$—, —$(C(R^m)═C(R^n))$—, —$(C(R^{mm})═C(R^{nn}))$—, or a single bond, wherein $R^d$, $R^e$, $R^f$, $R^g$, $R^h$, $R^i$, $R^j$, $R^m$, and $R^n$ are each independently hydrogen, a halogen, a substituted or unsubstituted C1 to C10 alkyl group, or a substituted or unsubstituted C6 to C10 aryl group, $R^{gg}$ and $R^{hh}$ are linked to each other to provide a first ring structure, $R^{ii}$ and $R^{ij}$ are linked to each other to provide a second ring structure, $R^{mm}$ and $R^{nn}$ are linked to each other to provide a third ring structure, and n of —$(CR^dR^e)_n$— is 1 or 2.

11. The compound of claim 1, wherein the compound has a maximum absorption wavelength ($\Delta_{max}$) in a wavelength region of greater than or equal to about 500 nm and less than or equal to about 600 nm, in a thin film state.

12. The compound of claim 1, wherein the compound is configured to exhibit a light absorption curve having a full width at half maximum (FWHM) of about 50 nm to about 120 nm, in a thin film state.

13. A photoelectric device, comprising:
   a first electrode and a second electrode facing each other, and
   an active layer between the first electrode and the second electrode
   wherein the active layer comprises the compound of claim 1.

14. An image sensor comprising the photoelectric device of claim 13.

15. The image sensor of claim 14, wherein
   the image sensor comprises a semiconductor substrate integrated with a plurality of first photo-sensing devices configured to sense light in a blue wavelength region and a plurality of second photo-sensing devices configured to sense light in a red wavelength region, and
   the photoelectric device is on the semiconductor substrate and is configured to selectively sense light in a green wavelength region.

16. The image sensor of claim 15, further comprising a color filter layer comprising a blue filter configured to selectively transmit light in the blue wavelength region and a red filter configured to selectively transmit light in the red wavelength region.

17. The image sensor of claim 15, wherein the plurality of first photo-sensing devices and the plurality of second photo-sensing devices are stacked in a vertical direction in the semiconductor substrate.

18. The image sensor of claim 14, wherein
   the photoelectric device is a green photoelectric device configured to selectively absorb light in a green wavelength region,
   the image sensor includes the green photoelectric device, a blue photoelectric device configured to selectively absorb light in a blue wavelength region, and a red photoelectric device configured to selectively absorb light in a red wavelength region, and
   where the green photoelectric device, the blue photoelectric device, and the red photoelectric device are stacked.

19. An electronic device comprising the image sensor of claim 14.

* * * * *